United States Patent
Komori et al.

(10) Patent No.: US 8,003,699 B2
(45) Date of Patent: *Aug. 23, 2011

(54) AMIDE COMPOUND AND USE THEREOF FOR CONTROLLING PLANT DISEASES

(75) Inventors: Takashi Komori, Tokyo (JP); Mayumi Kubota, Toyonaka (JP); Yuichi Matsuzaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/451,115

(22) PCT Filed: Apr. 25, 2008

(86) PCT No.: PCT/JP2008/058033
§ 371 (c)(1),
(2), (4) Date: Oct. 27, 2009

(87) PCT Pub. No.: WO2008/136389
PCT Pub. Date: Nov. 13, 2008

(65) Prior Publication Data
US 2010/0105647 A1 Apr. 29, 2010

(30) Foreign Application Priority Data
Apr. 27, 2007 (JP) .................. 2007-118648

(51) Int. Cl.
*A01N 37/18* (2006.01)
*C07C 235/46* (2006.01)
*C07C 235/48* (2006.01)
*C07C 235/50* (2006.01)
*C07C 235/54* (2006.01)

(52) U.S. Cl. ........ 514/622; 514/546; 560/250; 564/176; 564/155

(58) Field of Classification Search ......... 562/512, 562/588; 564/171, 184
See application file for complete search history.

(56) References Cited

U.S. PATENT DOCUMENTS

| | | | |
|---|---|---|---|
| 4,946,865 | A | 8/1990 | Takahashi et al. |
| 2004/0049065 | A1 | 3/2004 | Craig et al. |
| 2004/0248739 | A1 | 12/2004 | Schaetzer et al. |
| 2008/0319080 | A1 | 12/2008 | Komori |
| 2009/0131531 | A1 | 5/2009 | Komori |
| 2010/0048701 | A1 * | 2/2010 | Komori et al. ............... 514/543 |

FOREIGN PATENT DOCUMENTS

| | | | |
|---|---|---|---|
| EP | 1295868 | * | 3/2003 |
| EP | 1 770 085 | A1 | 4/2007 |
| JP | 63-154601 | | 6/1988 |
| JP | 2004-074537 | | 3/2004 |
| WO | 03/104206 | | 12/2003 |
| WO | 2004/002981 | | 1/2004 |
| WO | 2007/049728 | | 5/2007 |
| WO | 2007/049729 | | 5/2007 |
| WO | 2008/136385 | | 11/2008 |
| WO | 2008/136387 | | 11/2008 |
| WO | 2008/136388 | | 11/2008 |
| WO | 2009/004978 | | 1/2009 |
| WO | 2009/011305 | | 1/2009 |

OTHER PUBLICATIONS

Patini, et al., Chem. Rev, 1996, 96, 3147-3176, esp. p. 3149.*
Supplementary European Search Report issued Mar. 24, 2010 in European Application No. 08752107.6.
Par J. Vacher et al., "Quelques aspects de l'activite pharmacodynamique de derives de l'acide 3,5-dimethoxy-4-hydroxy-benzoique", Med. Pharmacol. 12(1), 49-55 (1965), with Translation of Table II.
International Search Report issued Jul. 15, 2008 in International (PCT) Application No. PCT/JP2008/058033.
Abstract of JP 2007-145816, published Jun. 14, 2007.
Abstract of JP 2007-145817, published Jun. 14, 2007.
Abstract of JP 63-027450, published Feb. 5, 1988.
European Office Action issued Mar. 17, 2011 in corresponding European Application No. 08 752 107.6.

* cited by examiner

*Primary Examiner* — Joseph Kosack
*Assistant Examiner* — Matthew P Coughlin
(74) *Attorney, Agent, or Firm* — Wenderoth, Lind & Ponack, L.L.P.

(57) ABSTRACT

Disclosed is an amide compound represented by the following formula (1). (1) (In the formula, $X^1$ represents a fluorine atom or a methoxy group; $X^2$ represents a hydrogen atom, a halogen atom, a $C_1$-$C_4$ alkyl group or the like; Z represents an oxygen atom or a sulfur atom; and A represents an $A^1$-$CR^6R^7R^8$ group, an $A^2$-$Cy^1$ group or an $A^3$-$Cy^2$ group, wherein $A^1$ represents a $CH_2$ group or the like, $A^2$ represents a single bond, a $CH_2$ group or the like, $Cy^1$ represents a $C_3$-$C_6$ cycloalkyl group substituted with a $C_1$-$C_6$ alkoxy group or the like, $Cy^2$ represents a $C_3$-$C_6$ cycloalkyl group which may be substituted with at least one halogen atom or the like, $R^6$ and $R^7$ independently represent a $C_1$-$C_4$ alkyl group, and $R^8$ represents a halogen atom, a hydroxyl group or the like.) The amide compound has excellent plant disease controlling activity.

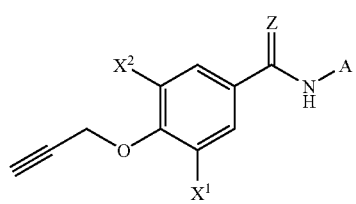

(1)

15 Claims, No Drawings

AMIDE COMPOUND AND USE THEREOF FOR CONTROLLING PLANT DISEASES

TECHNICAL FIELD

The present invention relates to an amide compound and use thereof for controlling plant diseases.

BACKGROUND ART

Heretofore, chemicals for controlling plant diseases have been developed, and compounds having plant disease controlling activity have been found and are served for practical use.

DISCLOSURE OF THE INVENTION

Problem to be Solved by the Invention

An object of the present invention is to provide a compound having excellent plant disease controlling activity.

Means for Solving the Problem

The present inventors have intensively studied so as to find a compound having excellent plant disease controlling activity. As a result, they have found that an amide compound represented by the following formula (1) has excellent plant disease controlling activity, and thus the present invention has been completed.

That is, the present invention provides an amide compound represented by the formula (1):

[Chemical Formula 1]

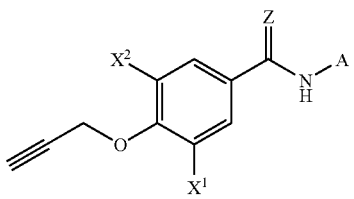

(1)

which is, hereinafter referred to as the present compound, wherein $X^1$ represents a fluorine atom or a methoxy group, $X^2$ represents a hydrogen atom, a halogen atom, a $C_1$-$C_4$ alkyl group, a $C_2$-$C_4$ alkenyl group, a $C_2$-$C_4$ alkynyl group, a $C_1$-$C_4$ haloalkyl group, a $C_1$-$C_4$ alkoxy group, a $C_1$-$C_4$ alkylthio group, a hydroxy $C_1$-$C_4$ alkyl group, a nitro group, a cyano group, a formyl group, a $NR^1R^2$ group, a $CO_2R^3$ group, a $CONR^4R^5$ group, or a phenyl group optionally substituted with at least one group selected from the group consisting of a methyl group, a halogen atom, a cyano group and a nitro group, Z represents an oxygen atom or a sulfur atom, A represents a group represented by $A^1$-$CR^6R^7R^8$, $A^2$-$Cy^1$ or $A^3$-$Cy^2$, $A^1$ represents a $CH_2$ group, a $CH(CH_3)$ group, a $C(CH_3)_2$ group or a $CH(CH_2CH_3)$ group, $A^2$ represents a single bond, a $CH_2$ group, a $CH(CH_3)$ group, a $C(CH_3)_2$ group or a $CH(CH_2CH_3)$ group, $A^3$ represents a methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group, $Cy^1$ represents a $C_3$-$C_6$ cycloalkyl group substituted with at least one group selected from the following group [a-1], a $C_3$-$C_6$ cycloalkenyl group optionally substituted with at least one group selected from the following group [a-1], a $C_3$-$C_6$ cycloalkyl group optionally substituted with at least one group selected from the following group [a-1], and one of whose ring-forming methylenes is replaced with a carbonyl group, or a $C_3$-$C_6$ hydroxyiminocycloalkyl group optionally substituted with at least one group selected from the following group [a-1], $Cy^2$ represents a $C_3$-$C_6$ cycloalkyl group optionally substituted with at least one group selected from the following group [a-2], a $C_3$-$C_6$ cycloalkenyl group optionally substituted with at least one group selected from the following group [a-2], a $C_3$-$C_6$ cycloalkyl group optionally substituted with at least one group selected from the following group [a-2], and one of whose ring-forming methylenes is replaced with a carbonyl group, or a $C_3$-$C_6$ hydroxyiminocycloalkyl group optionally substituted with at least one group selected from the following group [a-2], $R^1$ and $R^2$ represent independently a hydrogen atom, a $C_1$-$C_4$ alkyl group, a $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^3$ represents a $C_1$-$C_4$ alkyl group, a $C_3$-$C_4$ alkenyl group or a $C_3$-$C_4$ alkynyl group, $R^4$ represents a hydrogen atom, a $C_1$-$C_4$ alkyl group, $C_3$-$C_4$ alkenyl group, a $C_3$-$C_4$ alkynyl group, a $C_2$-$C_4$ haloalkyl group, a $C_2$-$C_5$ alkylcarbonyl group, a $C_2$-$C_5$ alkoxycarbonyl group or a $C_1$-$C_4$ alkylsulfonyl group, $R^5$ represents a hydrogen atom, a $C_1$-$C_4$ alkyl group, a $C_3$-$C_4$ alkenyl group, a $C_3$-$C_4$ alkynyl group or a $C_2$-$C_4$ haloalkyl group, $R^6$ and $R^7$ represent independently a $C_1$-$C_4$ alkyl group, $R^8$ represents a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a $(C_1$-$C_3$ alkylamino)$C_1$-$C_6$ alkyl group, a $(di(C_1$-$C_3$ alkyl)amino) $C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group or an $NR^9R^{10}$ group (wherein $R^9$ and $R^{10}$ represent independently a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group);

Group [a-1]:

a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a $(C_1$-$C_3$ alkylamino) $C_1$-$C_6$ alkyl group, a $(di(C_1$-$C_3$ alkyl)amino) $C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group and an $NR^{11}R^{12}$ group (wherein $R^{11}$ and $R^{12}$ represent independently a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group);

Group [a-2]:

a halogen atom, a $C_1$-$C_4$ alkyl group, a $C_2$-$C_4$ alkenyl group, a $C_2$-$C_4$ alkynyl group, a hydroxyl group, a cyano group, a carboxyl group, a $C_2$-$C_5$ alkoxycarbonyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a ($C_1$-$C_3$ alkylamino) $C_1$-$C_6$ alkyl group, a (di($C_1$-$C_3$ alkyl)amino) $C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group and an $NR^{13}R^{14}$ group (wherein $R^{13}$ and $R^{14}$ represent independently a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group); a plant disease controlling agent containing the present compound as an active ingredient; and a plant disease controlling method comprising treating a plant or a soil with an effective amount of the present compound.

Effects of the Invention

Since the present compound has excellent plant disease controlling activity, it is useful as an active ingredient of a plant disease controlling agent.

BEST MODE FOR CARRYING OUT THE INVENTION

In the present invention,

Examples of the halogen atom represented by $X^2$ include a fluorine atom, a chlorine atom, a bromine atom and an iodine atom, Examples of the $C_1$-$C_4$ alkyl group include a methyl group, an ethyl group, a 1-methylethyl group, a 1,1-dimethylethyl group, a propyl group and a 1-methylpropyl group, Examples of the $C_2$-$C_4$ alkenyl group include a vinyl group, a 1-propenyl group, a 2-propenyl group, a 2-butenyl group and a 3-butenyl group, Examples of the $C_2$-$C_4$ alkynyl group include an ethynyl group, a 1-propynyl group, a 2-propynyl group and a 3-butynyl group, Examples of the $C_1$-$C_4$ haloalkyl group include a fluoromethyl group, a chloromethyl group, a bromomethyl group, a difluoromethyl group, a dichloromethyl group, a dibromomethyl group, a trifluoromethyl group, trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group, a 4-fluorobutyl group and a 1-chloroethyl group, Examples of the $C_1$-$C_4$ alkoxy group include a methoxy group, an ethoxy group, a 1-methylethoxy group, a 1,1-dimethylethoxy group, a propoxy group, a 1-methylpropoxy group, a 2-methylpropoxy group, and a butoxy group, Examples of the $C_1$-$C_4$ alkylthio group include a methylthio group, an ethylthio group, a 1-methylethylthio group, a 1,1-dimethylethylthio group, a propylthio group and a 1-methylpropylthio group, Examples of the hydroxy $C_1$-$C_4$ alkyl group include a hydroxymethyl group, a 1-hydroxyethyl group and a 2-hydroxyethyl group, Examples of the phenyl group optionally substituted with at least one group selected from the group consisting of a methyl group, a halogen atom, a cyano group and a nitro group include a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a 4-cyanophenyl group and a 4-nitrophenyl group, Examples of the $C_1$-$C_3$ haloalkyl group in the methylene group substituted with at least one group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group represented by $A^3$ include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group and a 1-chloroethyl group, Examples of the $C_2$-$C_4$ alkenyl group include a vinyl group, a 1-propenyl group, a 2-propenyl group, a 2-butenyl group and a 3-butenyl group, Examples of the $C_2$-$C_4$ alkynyl group include an ethynyl group, a 1-propynyl group, a 2-propynyl group and a 3-butynyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the methylene group substituted with at least one kind of group selected from the group consisting of a $C_1$-$C_3$ haloalkyl group, a $C_2$-$C_4$ alkenyl group, a $C_2$-$C_4$ alkynyl group, a cyano group, a phenyl group and a $C_2$-$C_5$ alkoxycarbonyl group represented by $A^3$ include specifically $CH(CF_3)$, $CH(CF_2H)$, $CH(CFH_2)$, $CH(CH_2CF_3)$, $CH(CCl_3)$, $CH(CCl_2H)$, $CH(CClH_2)$, $CH(CH=CH_2)$, $CH(CH=CHCH_3)$, $CH(CH=C(CH_3)_2)$, $CH(C\equiv CH)$, $CH(C\equiv CCH_3)$, $CH(CH_2C\equiv CH)$, $CH(CN)$, $CH(C_6H_5)$, $CH(CO_2CH_3)$, $CH(CO_2CH_2CH_3)$ and $CH(CO_2CH(CH_3)_2)$, Examples of the $C_1$-$C_4$ alkyl group represented by $R^1$ include a methyl group, an ethyl group, a 1-methylethyl group, a 1,1-dimethylethyl group, a propyl group and a 1-methylpropyl group, Examples of the $C_3$-$C_4$ alkenyl group include a 1-propenyl group, a 2-propenyl group, a 2-butenyl group and a 3-butenyl group, Examples of the $C_3$-$C_4$ alkynyl group include a 1-propynyl group, a 2-propynyl group and a 3-butynyl group, Examples of the $C_2$-$C_4$ haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, Examples of the $C_1$-$C_4$ alkyl group represented by $R^2$ include a methyl group, an ethyl group, a 1-methylethyl group, a 1,1-dimethylethyl group, a propyl group and a 1-methylpropyl group, Examples of the $C_3$-$C_4$ alkenyl group include a 1-propenyl group, a 2-propenyl group, a 2-butenyl group and a 3-butenyl group, Examples of the $C_3$-$C_4$ alkynyl group include a 1-propynyl group, a 2-propynyl group and a 3-butynyl group, Examples of the $C_2$-$C_4$ haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group, Examples of the $C_2$-$C_5$ alkylcarbonyl group include an acetyl group, an ethylcarbonyl group, a 1-methylethylcarbonyl group, and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, Examples of the $C_1$-$C_4$ alkyl group represented by $R^3$ include a methyl group, an ethyl group, a 1-methylethyl group, a 1,1-dimethylethyl group, a propyl group and a 1-methylpropyl group, Examples of the $C_3$-$C_4$ alkenyl group include a 1-propenyl group, a 2-propenyl group, a 2-butenyl group and a 3-butenyl group, Examples of the $C_3$-$C_4$ alkynyl group include a 1-propynyl group, a 2-propynyl group and a 3-butynyl group, Examples of the $C_1$-$C_4$ alkyl group represented by $R^4$ include a methyl group, an ethyl group, a 1-methylethyl group, a 1,1-dimethylethyl group, a propyl group and a 1-methylpropyl group, Examples of the $C_3$-$C_4$ alkenyl group include a 1-propenyl group, a 2-propenyl group, a 2-butenyl group and a 3-butenyl group, Examples of the $C_3$-$C_4$ alkynyl group include a 1-propynyl group, a 2-propynyl group and a 3-butynyl group, Examples of the $C_2$-$C_4$ haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group, and a 1,1-dimethylethoxycarbonyl group, Examples of the $C_1$-$C_4$ alkylsulfonyl group include a methylsulfonyl group, an ethylsulfonyl group a 1-methylethylsulfonyl group and a 1,1-dimethylethylsulfonyl group, Examples of the $C_1$-$C_4$ alkyl group represented by $R^5$ include a methyl group, an ethyl group, a 1-methylethyl group, a 1,1-dimethylethyl group, a propyl group and a 1-methylpropyl group, Examples of the $C_3$-$C_4$ alkenyl group include a 1-propenyl group, a 2-propenyl group, a 2-butenyl group and a 3-butenyl group, Examples of the $C_3$-$C_4$ alkynyl group include a 1-propynyl group, a 2-propynyl group and a 3-butynyl group, Examples of the $C_2$-$C_4$ haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group, Examples of the $NR^1R^2$ group include an amino group, a methylamino group, a dimethylamino group, an ethylamino group, a 2-propenylamino group, a 2-propynylamino group, a 2-chloroethylamino group, an acetylamino group, a propionylamino group, a 1,1-dimethylethylcarbonylamino group, a methoxycarbonylamino group, an ethoxycarbonylamino group, a methanesulfonylamino group, an N-acetyl-N-methylamino group, an N-ethoxycarbonyl-N-methylamino group and a methanesulfonylmethylamino group, Examples of the $CONR^4R^5$ group, include a carbamoyl group, a methylcarbamoyl group, a dimethylcarbamoyl group, an ethylmethylcarbamoyl group, a (2-propenyl)carbamoyl group, a (2-propynyl)carbamoyl group and a 2-chloroethylcarbamoyl group, Examples of the $C_1$-$C_4$ alkyl group represented by $R^6$ include a methyl group, an ethyl group, a 1-methylethyl group, a 1,1-dimethylethyl group, a propyl group and a 1-methylpropyl group, Examples of the $C_1$-$C_4$ alkyl group represented by $R^7$ include a methyl group, an ethyl group, a 1-methylethyl group, a 1,1-dimethylethyl group, a propyl group and a 1-methylpropyl group, Examples of the halogen atom represented by $R^8$ include a fluorine atom, a chlorine atom, a bromine atom and an iodine atom, Examples of the $C_1$-$C_6$ alkoxy group include a methoxy group, an ethoxy group, a propoxy group, an isopropoxy group, a butoxy group, an isobutoxy group, a sec-butoxy group, a tert-butoxy group, a pentyloxy group, an isopentyloxy group and a hexyloxy group, Examples of the $C_3$-$C_6$ alkenyloxy group include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group, Examples of the $C_1$-$C_6$ haloalkyl group include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group, Examples of the $C_1$-$C_6$ haloalkoxy group include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group, Examples of the $C_1$-$C_3$ alkylthio group include a methylthio group, an ethylthio group, a 1-methylethylthio group and a propylthio group, Examples of the hydroxy $C_1$-$C_6$ alkyl group include a hydroxymethyl group, a 1-hydroxyethyl group, a 2-hydroxyethyl group, a 1-hydroxypropyl group and a 2-hydroxypropyl group, Examples of the $C_2$-$C_4$ alkylcarbonyloxy group include an acetoxy group, an ethylcarbonyloxy group, a 1-methylethylcarbonyloxy group and a propylcarbonyloxy group, Examples of the ($C_1$-$C_3$ alkylamino) $C_1$-$C_6$ alkyl group include an N-methylaminomethyl group, an N-ethylaminomethyl group, a 1-(N-methylamino)ethyl group, a 2-(N-methylamino)ethyl group and a 1-(N-ethylamino)ethyl group, Examples of the (di($C_1$-$C_3$ alkyl)amino) $C_1$-$C_6$ alkyl group include an N,N-dimethylaminomethyl group, a 1-(N,N-dimethylamino)ethyl group, a 2-(N,N-dimethylamino)ethyl group and an N,N-diethylaminoethyl group, Examples of the $C_2$-$C_6$ cyanoalkyl group include a cyanomethyl group, a 1-cyanoethyl group and a 2-cyanoethyl group, Examples of the $C_1$-$C_3$ alkylsulfonyl group include a methanesulfonyl group and an ethanesulfonyl group, Examples of the $C_1$-$C_4$ alkyl group represented by $R^9$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, Examples of the $C_1$-$C_4$ alkyl group represented by $R^{10}$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, and Examples of the $NR^9R^{10}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

In the group [a-1],

Examples of the $C_1$-$C_6$ alkoxy group include a methoxy group, an ethoxy group, a propoxy group, an isopropoxy group, a butoxy group, an isobutoxy group, a sec-butoxy group, a tert-butoxy group, a pentyloxy group, an isopentyloxy group and a hexyloxy group, Examples of the $C_3$-$C_6$ alkenyloxy group include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group, Examples of the $C_1$-$C_6$ haloalkyl group include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group, Examples of the $C_1$-$C_6$ haloalkoxy group include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group, Examples of the $C_1$-$C_3$ alkylthio group include a methylthio group, an ethylthio group, a 1-methylethylthio group and a propylthio group, Examples of the $C_1$-$C_3$ alkylidene group forming a double bond with the same ring-forming carbon atom include a methylene group forming a double bond with the same ring-forming carbon atom, an ethylidene group forming a double bond with the same ring-forming carbon atom, an isopropylidene group forming a double bond with the same ring-forming carbon atom and a propylidene group forming a double bond with the same ring-forming carbon atom, Examples of the hydroxy $C_1$-$C_6$ alkyl group include a hydroxymethyl group, a 1-hydroxyethyl group, a 2-hydroxyethyl group, a 1-hydroxypropyl group and a 2-hydroxypropyl group, Examples of the $C_2$-$C_4$ alkylcarbonyloxy group include an acetoxy group, an ethylcarbonyloxy group, a 1-methylethylcarbonyloxy group and a propylcarbonyloxy group, Examples of the ($C_1$-$C_3$ alkylamino)$C_1$-$C_6$ alkyl group include an N-methylaminomethyl group, an N-ethylaminomethyl group, a 1-(N-methylamino)ethyl group, a 2-(N-methylamino)ethyl group and a 1-(N-ethylamino)ethyl group, Examples of the (di($C_1$-$C_3$ alkyl)amino)$C_1$-$C_6$ alkyl group include an N,N-dimethylaminomethyl group, a 1-(N,N-dimethylamino)ethyl group, a 2-(N,N-dimethylamino)ethyl group and an N,N-diethylaminomethyl group, Examples of the $C_2$-$C_6$ cyanoalkyl group include a cyanomethyl group, a 1-cyanoethyl group and a 2-cyanoethyl group, Examples of the $C_1$-$C_3$ alkylsulfonyl group include a methanesulfonyl group and an ethanesulfonyl group, Examples of the $C_1$-$C_4$ alkyl group represented by $R^{11}$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, Examples of the $C_1$-$C_4$ alkyl group represented by $R^{12}$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, and Examples of the $NR^{11}R^{12}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

In the group [a-2],

Examples of the halogen atom include a fluorine atom, a chlorine atom, a bromine atom and an iodine atom, Examples of the $C_1$-$C_4$ alkyl group include a methyl group, an ethyl group, a 1-methylethyl group, a 1,1-dimethylethyl group, a propyl group and a 1-methylpropyl group, Examples of the $C_2$-$C_4$ alkenyl group include a vinyl group, a 1-propenyl group, a 2-propenyl group, a 2-butenyl group and a 3-butenyl group, Examples of the $C_2$-$C_4$ alkynyl group include an ethynyl group, a 1-propynyl group, a 2-propynyl group and a 3-butynyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_6$ alkoxy group include a methoxy group, an ethoxy group, a propoxy group, an isopropoxy group, a butoxy group, an isobutoxy group, a sec-butoxy group, a tert-butoxy group, a pentyloxy group, an isopentyloxy group and a hexyloxy group, Examples of the $C_3$-$C_6$ alkenyloxy group include a 2-propenyloxy group, a 1-methyl-2-propenyloxy group, a 2-methyl-2-propenyloxy group, a 2-butenyloxy group, a 3-butenyloxy group, a 2-hexenyloxy group and a 5-hexenyloxy group, Examples of the $C_1$-$C_6$ haloalkyl group include a fluoromethyl group, a difluoromethyl group, a trifluoromethyl group, a trichloromethyl group, a chlorofluoromethyl group, a bromodifluoromethyl group, a 2-fluoroethyl group, a 2,2-difluoroethyl group, a 2,2,2-trifluoroethyl group and a 6,6,6-trifluorohexyl group, Examples of the $C_1$-$C_6$ haloalkoxy group include a trifluoromethoxy group, a difluoromethoxy group, a bromodifluoromethoxy group, a chlorodifluoromethoxy group, a fluoromethoxy group, a 2,2,2-trifluoroethoxy group, a 1,1,2,2-tetrafluoroethoxy group, a 5-chloropentyloxy group, a 4-fluoroisopentyloxy group and a 2,2-dichlorohexyloxy group, Examples of the $C_1$-$C_3$ alkylthio group include a methylthio group, an ethylthio group, a 1-methylethylthio group and a propylthio group, Examples of the $C_1$-$C_3$ alkylidene group forming a double bond with the same ring-forming carbon atom include a methylene group forming a double bond with the same ring-forming carbon atom, an ethylidene group forming a double bond with the same ring-forming carbon atom, an isopropylidene group forming a double bond with the same ring-forming carbon atom and a propylidene group forming a double bond with the same ring-forming carbon atom, Examples of the hydroxy $C_1$-$C_6$ alkyl group include a hydroxymethyl group, a 1-hydroxyethyl group, a 2-hydroxyethyl group, a 1-hydroxypropyl group and a 2-hydroxypropyl group, Examples of the $C_2$-$C_4$ alkylcarbonyloxy group include an acetoxy group, an ethylcarbonyloxy group, a 1-methylethylcarbonyloxy group and a propylcarbonyloxy group, Examples of the ($C_1$-$C_3$ alkylamino)$C_1$-$C_6$ alkyl group include an N-methylaminomethyl group, an N-ethylaminomethyl group, a 1-(N-methylamino)ethyl group, a 2-(N-methylamino)ethyl group and a 1-(N-ethylamino)ethyl group, Examples of the (di($C_1$-$C_3$ alkyl)amino)$C_1$-$C_6$ alkyl group include an N,N-dimethylaminomethyl group, a 1-(N,N-dimethylamino)ethyl group, a 2-(N,N-dimethylamino)ethyl group and an N,N-diethylaminomethyl group, Examples of the $C_2$-$C_6$ cyanoalkyl group include a cyanomethyl group, a 1-cyanoethyl group and a 2-cyanoethyl group, Examples of the $C_1$-$C_3$ alkylsulfonyl group include a methanesulfonyl group and an ethanesulfonyl group, Examples of the $C_1$-$C_4$ alkyl group represented by $R^{13}$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, Examples of the $C_1$-$C_4$ alkyl group represented by $R^{14}$ include a methyl group, an ethyl group, a 1-methylethyl group, a 1,1-dimethylethyl group, a propyl group and a 1-methylpropyl group, Examples of the $C_2$-$C_5$ alkylcarbonyl group include an acetyl group, an ethylcarbonyl group, a 1-methylethylcarbonyl group and a 1,1-dimethylethylcarbonyl group, Examples of the $C_2$-$C_5$ alkoxycarbonyl group include a methoxycarbonyl group, an ethoxycarbonyl group, a 1-methylethoxycarbonyl group and a 1,1-dimethylethoxycarbonyl group, Examples of the $C_1$-$C_4$ alkylsulfonyl group include a methylsulfonyl group, an ethylsulfonyl group, a 1-methylethylsulfonyl group and a 1,1-dimethylethylsulfonyl group, and Examples of the $NR^{13}R^{14}$ group include an amino group, a methylamino group, a dimethylamino group, an ethylamino group, an acetylamino group, a propionylamino group, a 1,1-dimethylethylcarbonylamino group, a methoxycarbonylamino group, an ethoxycarbonylamino group, a 1,1-dimethylethoxycarbonylamino group, a methanesulfonylamino group, an N-acetyl-N-methylamino group, an N-ethoxycarbonyl-N-methylamino group and a methanesulfonylmethylamino group.

In $Cy^1$,

Examples of the $C_3$-$C_6$ cycloalkyl group in the $C_3$-$C_6$ cycloalkyl group substituted with at least one group selected from the group [a-1] include a cyclopropyl group, a cyclobutyl group, a cyclopentyl group and a cyclohexyl group, Examples of the $C_3$-$C_6$ cycloalkenyl group in the $C_3$-$C_6$ cycloalkenyl group optionally substituted with at least one group selected from the group [a-1] include a 2-cyclopropenyl group, a 1-cyclobutenyl group, a 2-cyclobutenyl group, a 1-cyclopentenyl group, a 2-cyclopentenyl group, a 3-cyclopentenyl group, a 1-cyclohexenyl group, a 2-cyclohexenyl group and a 3-cyclohexenyl group, Examples of the $C_3$-$C_6$ cycloalkyl group optionally substituted with at least one group selected from the group [a-1], and one of whose ring-forming methylenes is replaced with a carbonyl group include a 2-oxocyclopropyl group, a 2-oxocyclobutyl group, a 3-oxocyclobutyl group, a 2-oxocyclopentyl group, a 3-oxocyclopentyl group, a 2-oxocyclohexyl group, a 3-oxocyclohexyl group and a 4-oxocyclohexyl group, and Examples of the $C_3$-$C_6$ hydroxyiminocycloalkyl group in the $C_3$-$C_6$ hydroxyiminocycloalkyl group optionally substituted with at least one group selected from the group [a-1] include a 2-hydroxyiminocyclopropyl group, 2-hydroxyiminocyclobutyl group, a 3-hydroxyiminocyclobutyl group, a 2-hydroxyiminocyclopentyl group, a 3-hydroxyiminocyclopentyl group, a 2-hydroxyiminocyclohexyl group, a 3-hydroxyiminocyclohexyl group and a 4-hydroxyiminocyclohexyl group.

In $Cy^2$,

Examples of the $C_3$-$C_6$ cycloalkyl group in the $C_3$-$C_6$ cycloalkyl group optionally substituted with at least one group selected from the group [a-2] include a cyclopropyl group, a cyclobutyl group, a cyclopentyl group and a cyclohexyl group, Examples of the $C_3$-$C_6$ cycloalkenyl group in the $C_3$-$C_6$ cycloalkenyl group optionally substituted with at least one group selected from the group [a-2] include a 2-cyclopropenyl group, a 1-cyclobutenyl group, a 2-cyclobutenyl group, a 1-cyclopentenyl group, a 2-cyclopentenyl group, a 3-cyclopentenyl group, a 1-cyclohexenyl group, a 2-cyclohexenyl group and a 3-cyclohexenyl group, Examples of the $C_3$-$C_6$ cycloalkyl group optionally substituted with at least one group selected from the group [a-2], and one of whose ring-forming methylenes is replaced with a carbonyl group include a 2-oxocyclopropyl group, a 2-oxocyclobutyl group, a 3-oxocyclobutyl group, a 2-oxocyclopentyl group, a 3-oxocyclopentyl group, a 2-oxocyclohexyl group, a 3-oxocyclohexyl group and a 4-oxocyclohexyl group, and Examples of the $C_3$-$C_6$ hydroxyiminocycloalkyl group in the $C_3$-$C_6$ hydroxyiminocycloalkyl group optionally substituted with at least one group selected from the group [a-1] include a 2-hydroxyiminocyclopropyl group, a 2-hydroxyiminocyclobutyl group, a 3-hydroxyiminocyclobutyl group, a 2-hydroxyiminocyclopentyl group, a 3-hydroxyiminocyclopentyl group, a 2-hydroxyiminocyclohexyl group, a 3-hydroxyiminocyclohexyl group and a 4-hydroxyiminocyclohexyl group.

Specific examples of the group represented by $A^2$-$Cy^1$ include:

a {1-(hydroxymethyl)cyclohexyl}methyl group, a {1-(hydroxymethyl)cyclobutyl}methyl group, a {1-(hydroxymethyl)cyclopentyl}methyl group, a {1-(hydroxymethyl)cyclopropyl}methyl group, a (3-cyclohexenyl)methyl group, a (2-cyclohexenyl)methyl group, a (1-cyclohexenyl)methyl group, a {1-(dimethylamino)cyclohexyl}methyl group, a {1-(dimethylamino)cyclopentyl}methyl group, a {1-(dimethylamino)cyclobutyl}methyl group, a {1-(dimethylamino)cyclopropyl}methyl group, a (1-acetoxycyclohexyl)methyl group, a (1-acetoxycyclopentyl)methyl group, a (1-acetoxycyclobutyl)methyl group, a (1-acetoxycyclopropyl)methyl group, a (2-acetoxycyclohexyl)methyl group, a 2-cyclohexenyl group, a 3-cyclohexenyl group, a 2-methoxycyclohexyl group, a 2-methoxycyclopentyl group, a 2-methoxycyclobutyl group, a 3-methoxycyclohexyl group, a 4-methoxycyclohexyl group, a (2-methoxycyclohexyl)methyl group, a (1-methoxycyclohexyl)methyl group, a 2-acetoxycyclohexyl group, a 2-acetoxycyclopentyl group, a 2-acetoxycyclobutyl group, a 2-methylthiocyclohexyl group, a 2-methylthiocyclopentyl group, a 2-methylthiocyclobutyl group, a 2-(1,1-dimethylethoxycarbonylamino)cyclohexyl group, a 2-(1,1-dimethylethoxycarbonylamino)cyclopentyl group, a 2-(1,1-dimethylethoxycarbonylamino)cyclobutyl group, a 2-aminocyclohexyl group, a 2-aminocyclopentyl group, a 2-aminocyclobutyl group, a 2-acetylaminocyclohexyl group, a 2-acetylaminocyclopentyl group, a 2-acetylaminocyclobutyl group, a 2-dimethylaminocyclohexyl group, a 2-dimethylaminocyclopentyl group, a 2-dimethylaminocyclobutyl group, a 2-phenylcyclohexyl group, a 2-phenylcyclopentyl group, a 2-phenylcyclobutyl group, a 2-benzylcyclohexyl group, a 2-benzylcyclopentyl group, a 2-benzylcyclobutyl group, a 2-trifluoromethylcyclohexyl group, a 2-trifluoromethylcyclopentyl group, a 2-trifluoromethylcyclobutyl group, a 2-trifluoromethylcyclopropyl group, a 2-hydroxymethylcyclohexyl group, a 2-hydroxymethylcyclopentyl group, a 2-hydroxymethylcyclobutyl group, a 2-methylenecyclohexyl group, a 3-methylenecyclohexyl group, a 4-methylenecyclohexyl group, a 2-oxocyclohexyl group, a 3-oxocyclohexyl group, a 4-oxocyclohexyl group, a 2-oxocyclopentyl group, a 3-oxocyclopentyl group, a 2-hydroxyiminocyclohexyl group, and a 2-hydroxyiminocyclopentyl group, and Specific examples of the group represented by $A^3$-$Cy^2$ include:

a 1-cyclohexyl-2,2,2-trifluoroethyl group, a 1-cyclopentyl-2,2,2-trifluoroethyl group, a 1-cyclobutyl-2,2,2-trifluoroethyl group, a 1-cyano-1-cyclohexylmethyl group, a 1-cyano-1-cyclopentylmethyl group, a 1-cyano-1-cyclobutylmethyl group, a 1-vinyl-1-cyclohexylmethyl group, a 1-vinyl-1-cyclopentylmethyl group, a 1-vinyl-1-cyclobutylmethyl group, a 1-methoxycarbonyl-1-cyclohexylmethyl group, a 1-methoxycarbonyl-1-cyclopentylmethyl group, a 1-methoxycarbonyl-1-cyclobutylmethyl group and the like.

As embodiments of the present compound, for example, there are the following compounds.

An amide compound of the formula (1), wherein $X^1$ is a fluorine atom, and $X^2$ is a hydrogen atom or a fluorine atom, or $X^1$ is a methoxy group, and $X^2$ is a hydrogen atom or a fluorine atom;

An amide compound of the formula (1), wherein Z is an oxygen atom, $X^1$ is a fluorine atom, and $X^2$ is a hydrogen atom;

An amide compound of the formula (1), wherein Z is an oxygen atom, $X^1$ is a fluorine atom, and $X^2$ is a fluorine atom;

An amide compound of the formula (1), wherein Z is an oxygen atom, $X^1$ is a fluorine atom, and $X^2$ is a methoxy group;

An amide compound of the formula (1), wherein Z is an oxygen atom, $X^1$ is a fluorine atom, and $X^2$ is a chlorine atom;

An amide compound of the formula (1), wherein Z is an oxygen atom, $X^1$ is a fluorine atom, and $X^2$ is a bromine atom;

An amide compound of the formula (1), wherein Z is an oxygen atom, $X^1$ is a fluorine atom, and $X^2$ is an iodine atom;

An amide compound of the formula (1), wherein Z is an oxygen atom, $X^1$ is a fluorine atom, and $X^2$ is a $C_1$-$C_4$ alkyl group;

An amide compound of the formula (1), wherein Z is an oxygen atom, $X^1$ is a fluorine atom, and $X^2$ is a $C_2$-$C_4$ alkenyl group;

An amide compound of the formula (1), wherein Z is an oxygen atom, $X^1$ is a fluorine atom, and $X^2$ is a $C_2$-$C_4$ alkynyl group;

An amide compound of the formula (1), wherein Z is an oxygen atom, $X^1$ is a fluorine atom, and $X^2$ is a $C_1$-$C_4$ haloalkyl group;

An amide compound of the formula (1), wherein Z is an oxygen atom, $X^1$ is a fluorine atom, and $X^2$ is a $C_1$-$C_4$ alkoxy group;

An amide compound of the formula (1), wherein Z is an oxygen atom, $X^1$ is a fluorine atom, and $X^2$ is a $C_1$-$C_4$ alkylthio group;

An amide compound of the formula (1), wherein Z is an oxygen atom, $X^1$ is a fluorine atom, and $X^2$ is a hydroxy $C_1$-$C_4$ alkyl group;

An amide compound of the formula (1), wherein Z is an oxygen atom, $X^1$ is a fluorine atom, and $X^2$ is a nitro group;

An amide compound of the formula (1), wherein Z is an oxygen atom, $X^1$ is a fluorine atom, and $X^2$ is a cyano group;

An amide compound of the formula (1), wherein Z is an oxygen atom, $X^1$ is a fluorine atom, and $X^2$ is a formyl group;

An amide compound of the formula (1), wherein Z is an oxygen atom, $X^1$ is a fluorine atom, and $X^2$ is a $NR^1R^2$ group;

An amide compound of the formula (1), wherein Z is an oxygen atom, $X^1$ is a fluorine atom, and $X^2$ is a $CO_2R^3$ group;

An amide compound of the formula (1), wherein Z is an oxygen atom, $X^1$ is a fluorine atom, and $X^2$ is a $CONR^4R^5$ group;

An amide compound of the formula (1), wherein Z is an oxygen atom, $X^1$ is a fluorine atom, and $X^2$ is a phenyl group optionally substituted with at least one group selected from the group consisting of a methyl group, a halogen atom, a cyano group and a nitro group;

An amide compound of the formula (1), wherein Z is an oxygen atom, $X^1$ is a methoxy group and $X^2$ is a hydrogen atom;

An amide compound of the formula (1), wherein Z is an oxygen atom, $X^1$ is a methoxy group and $X^2$ is a fluorine atom;

An amide compound of the formula (1), wherein Z is an oxygen atom, $X^1$ is a methoxy group and $X^2$ is a methoxy group;

An amide compound of the formula (1), wherein Z is an oxygen atom, $X^1$ is a methoxy group and $X^2$ is a chlorine atom;

An amide compound of the formula (1), wherein Z is an oxygen atom, $X^1$ is a methoxy group and $X^2$ is a bromine atom;

An amide compound of the formula (1), wherein Z is an oxygen atom, $X^1$ is a methoxy group and $X^2$ is an iodine atom;

An amide compound of the formula (1), wherein Z is an oxygen atom, $X^1$ is a methoxy group and $X^2$ is a $C_1$-$C_4$ alkyl group;

An amide compound of the formula (1), wherein Z is an oxygen atom, $X^1$ is a methoxy group and $X^2$ is a $C_2$-$C_4$ alkenyl group;

An amide compound of the formula (1), wherein Z is an oxygen atom, $X^1$ is a methoxy group and $X^2$ is a $C_2$-$C_4$ alkynyl group;

An amide compound of the formula (1), wherein Z is an oxygen atom, $X^1$ is a methoxy group and $X^2$ is a $C_1$-$C_4$ haloalkyl group;

An amide compound of the formula (1), wherein Z is an oxygen atom, $X^1$ is a methoxy group and $X^2$ is a $C_1$-$C_4$ alkoxy group;

An amide compound of the formula (1), wherein Z is an oxygen atom, $X^1$ is a methoxy group and $X^2$ is a $C_1$-$C_4$ alkylthio group;

An amide compound of the formula (1), wherein Z is an oxygen atom, $X^1$ is a methoxy group and $X^2$ is a hydroxy C1-C4 alkyl group;

An amide compound of the formula (1), wherein Z is an oxygen atom, $X^1$ is a methoxy group and $X^2$ is a nitro group;

An amide compound of the formula (1), wherein Z is an oxygen atom, $X^1$ is a methoxy group and $X^2$ is a cyano group;

An amide compound of the formula (1), wherein Z is an oxygen atom, $X^1$ is a methoxy group and $X^2$ is a formyl group;

An amide compound of the formula (1), wherein Z is an oxygen atom, $X^1$ is a methoxy group and $X^2$ is a $NR^1R^2$ group;

An amide compound of the formula (1), wherein Z is an oxygen atom, $X^1$ is a methoxy group and $X^2$ is a $CO^2R^3$ group;

An amide compound of the formula (1), wherein Z is an oxygen atom, $X^1$ is a methoxy group and $X^2$ is a $CONR^4R^5$ group;

An amide compound of the formula (1), wherein Z is an oxygen atom, $X^1$ is a methoxy group and $X^2$ is a phenyl group optionally substituted with at least one group selected from the group consisting of a methyl group, a halogen atom, a cyano group and a nitro group;

An amide compound of the formula (1), wherein Z is an oxygen atom;

An amide compound of the formula (1), wherein $X^1$ is a fluorine atom;

An amide compound of the formula (1), wherein $X^1$ is a methoxy group;

An amide compound of the formula (1), wherein Z is an oxygen atom, and $X^1$ is a fluorine atom;

An amide compound of the formula (1), wherein Z is an oxygen atom, and $X^1$ is a methoxy group;

An amide compound of the formula (1), wherein $X^2$ is a hydrogen atom, a halogen atom, a $C_1$-$C_4$ alkoxy group or a C1-C4 alkyl group;

An amide compound of the formula (1), wherein $X^2$ is a hydrogen atom;

An amide compound of the formula (1), wherein $X^2$ is a halogen atom;

An amide compound of the formula (1), wherein $X^2$ is a fluorine atom;

An amide compound of the formula (1), wherein $X^2$ is a hydrogen atom or a fluorine atom;

An amide compound of the formula (1), wherein $X^2$ is a methoxy group;

An amide compound of the formula (1), wherein $X^2$ is a $C_1$-$C_4$ alkyl group;

An amide compound of the formula (1), wherein Z is an oxygen atom, and $X^2$ is a hydrogen atom, a halogen atom, a $C_1$-$C_4$ alkoxy group or a $C_1$-$C_4$ alkyl group;

An amide compound of the formula (1), wherein Z is an oxygen atom, and $X^2$ is a hydrogen atom;

An amide compound of the formula (1), wherein Z is an oxygen atom, and $X^2$ is a halogen atom;

An amide compound of the formula (1), wherein Z is an oxygen atom, and $X^2$ is a fluorine atom;

An amide compound of the formula (1), wherein Z is an oxygen atom, and $X^2$ is a hydrogen atom or a fluorine atom;

An amide compound of the formula (1), wherein Z is an oxygen atom, and $X^2$ is a methoxy group;

An amide compound of the formula (1), wherein Z is an oxygen atom, and $X^2$ is a $C_1$-$C_4$ alkyl group;

An amide compound of the formula (1), wherein A is $A^1$-$CR^6R^7R^8$;

An amide compound of the formula (1), wherein A is $A^1$-$CR^6R^7R^8$, and $R^8$ is a fluorine atom, an amino group or a hydroxyl group;

An amide compound of the formula (1), wherein A is $A^1$-$CR^6R^7R^8$, and $R^8$ is an amino group or a hydroxyl group;

An amide compound of the formula (1), wherein A is $A^1$-$CR^6R^7R^8$, $A^1$ is a $CH_2$ group or a $CH(CH_3)$ group and $R^8$ is an amino group or a hydroxyl group;

An amide compound of the formula (1), wherein A is $A^1$-$CR^6R^7R^8$, and $R^8$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a (di($C_1$-$C_3$)alkyl) amino) $C_1$-$C_6$ alkyl group, a carbamoyl group, a formyl group, a $C_2$-$C_6$ cyanoalkyl group, a $C_1$-$C_3$ alkylsulfonyl group, or a phenoxy group;

An amide compound of the formula (1), wherein A is $A^1$-$CR^6R^7R^8$, and $R^8$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a hydroxy $C_1$-$C_6$ alkyl group, a $C_2$-$C_4$ alkylcarbonyloxy group, a (di($C_1$-$C_3$)alkyl)amino) $C_1$-$C_6$ alkyl group, a carbamoyl group, a formyl group, a $C_2$-$C_6$ cyanoalkyl group, a $C_1$-$C_3$ alkylsulfonyl group, or a phenoxy group;

An amide compound of the formula (1), wherein A is $A^1$-$CR^6R^7R^8$, and $R^8$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a hydroxy $C_1$-$C_6$ alkyl group or a $C_2$-$C_4$ alkylcarbonyloxy group;

An amide compound of the formula (1), wherein A is $A^1$-$CR^6R^7R^8$, $A^1$ is a $CH_2$ group or a $CH(CH_3)$ group and $R^8$ is a hydroxyl group;

An amide compound of the formula (1), wherein A is $A^1$-$CR^6R^7R^8$, and $R^8$ is a hydroxyl group;

An amide compound of the formula (1), wherein A is $A^2$-$Cy^1$;

An amide compound of the formula (1), wherein A is $A^2$-$Cy^1$, and $A^2$ is a single bond;

An amide compound of the formula (1), wherein A is $A^2$-$Cy^1$, and $A^2$ is a $CH_2$ group;

An amide compound of the formula (1), wherein A is $A^2$-$Cy^1$, and $A^2$ is a $CH(CH_3)$ group;

An amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group [a-1];

An amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group and a $NR^{11}R^{12}$ group;

An amide compound of the formula (1), wherein A is $A^2$-$Cy^1$, $A^2$ is a single bond, a $CH_2$ group or a $CH(CH_3)$ group, and $Cy^1$ is a cyclohexyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group and a $NR^{11}R^{12}$ group;

An amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group consisting of a methoxy group, a trifluoromethyl group, a methylthio group, a $CH_2$ group forming a double bond with the same ring-forming carbon atom, a hydroxymethyl group, an amino group, a methylamino group and a dimethylamino group;

An amide compound of the formula (1), wherein A is $A^2$-$Cy^1$, $A^2$ is a single bond, a $CH_2$ group or a $CH(CH_3)$ group, and $Cy^1$ is a cyclohexyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

An amide compound of the formula (1), wherein A is $A^2$-$Cy^1$, $A^2$ is a single bond, a $CH_2$ group or a $CH(CH_3)$ group, and $Cy^1$ is a cyclopentyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

An amide compound of the formula (1), wherein A is $A^2$-$Cy^1$, $A^2$ is a single bond, a $CH_2$ group or a $CH(CH_3)$ group, and $Cy^1$ is a cyclobutyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

An amide compound of the formula (1), wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a methoxy group, a trifluoromethyl group and a hydroxymethyl group;

An amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

An amide compound of the formula (1), wherein A is $A^2$-$Cy^1$, and $Cy^1$ is a $C_3$-$C_6$ cycloalkyl group substituted with at least one group selected from the following group [b-1], Group [b-1]
a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a carbamoyl group, a formyl group, a $C_2$-$C_6$ cyanoalkyl group, a $C_1$-$C_3$ alkylsulfonyl group and a phenoxy group;

An amide compound of the formula (1), wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the above group [b-1];

An amide compound of the formula (1), wherein $Cy^1$ is a $C_3$-$C_6$ cycloalkyl group substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a carbamoyl group, a formyl group, a $C_2$-$C_6$ cyanoalkyl group, a $C_1$-$C_3$ alkylsulfonyl group and a phenoxy group;

An amide compound of the formula (1), wherein $Cy^1$ is a $C_3$-$C_6$ cycloalkyl group substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino)$C_1$-$C_6$ alkyl group, a $C_2$-$C_6$ cyanoalkyl group and a phenoxy group;

An amide compound of the formula (1), wherein $Cy^1$ is a $C_3$-$C_6$ cycloalkyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group and a $C_2$-$C_4$ alkylcarbonyloxy group;

An amide compound of the formula (1), $Cy^1$ is a cyclohexyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group and a $C_2$-$C_4$ alkylcarbonyloxy group;

An amide compound of the formula (1), wherein $A^2$ is a single bond, a $CH_2$ group or a $CH(CH_3)$ group, and $Cy^1$ is cyclohexyl group substituted with at least one group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group and a $C_2$-$C_4$ alkylcarbonyloxy group;

An amide compound of the formula (1), wherein $Cy^1$ is a $C_3$-$C_6$ cycloalkyl group substituted with at least one group selected from the group consisting of a methoxy group, trifluoromethyl group, a methylthio group, a $CH_2$ group forming a double bond with the same ring-forming carbon atom, and a hydroxymethyl group;

An amide compound of the formula (1), wherein $A^2$ is a single bond, a $CH_2$ group or a $CH(CH_3)$ group, and $Cy^1$ is a $C_3$-$C_6$ cycloalkyl group substituted with at least one group selected from the group consisting of a methoxy group, a trifluoromethyl group, a methylthio group, a $CH_2$ group forming a double bond with the same ring-forming carbon atom, and a hydroxymethyl group;

An amide compound of the formula (1), wherein $A^2$ is a single bond, a $CH_2$ group or a $CH(CH_3)$ group, and $Cy^1$ is a cyclohexyl group substituted with at least one group selected from the group consisting of a methoxy group, a trifluoromethyl group, a methylthio group, a $CH_2$ group forming a double bond with the same ring-forming carbon atom, and a hydroxymethyl group;

An amide compound of the formula (1), wherein $A^2$ is a single bond, a $CH_2$ group or a $CH(CH_3)$ group, and $Cy^1$ is a cyclohexyl group substituted with at least one group selected from the group consisting of a methoxy group, a $CH_2$ group forming a double bond with the same ring-forming carbon atom, and a hydroxymethyl group;

An amide compound of the formula (1), wherein $Cy^1$ is a cyclohexenyl group optionally substituted with at least one group selected from the group [a-1];

An amide compound of the formula (1), wherein $Cy^1$ is a $C_3$-$C_6$ cycloalkenyl group optionally substituted with at least one group selected from the group [b-1];

An amide compound of the formula (1), wherein $Cy^1$ is a cyclohexenyl group optionally substituted with at least one group selected from the group [b-1];

An amide compound of the formula (1), wherein $Cy^1$ is a $C_3$-$C_6$ cycloalkenyl group optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a $C_2$-$C_6$ cyanoalkyl group and a phenoxy group;

An amide compound of the formula (1), wherein $Cy^1$ is a $C_3$-$C_6$ cycloalkenyl group;

An amide compound of the formula (1), wherein $Cy^1$ is a cyclohexenyl group;

An amide compound of the formula (1), wherein $Cy^1$ is a 1-cyclohexenyl group;

An amide compound of the formula (1), wherein $Cy^1$ is a cyclohexyl group optionally substituted with at least one group selected from the group [a-1], and one of whose ring-forming methylenes is replaced with a carbonyl group;

An amide compound of the formula (1), wherein $Cy^1$ is a $C_3$-$C_6$ cycloalkyl group optionally substituted with at least one group selected from the group [b-1], and one of whose ring-forming methylenes is replaced with a carbonyl group;

An amide compound of the formula (1), wherein $Cy^1$ is a cyclohexyl group optionally substituted with at least one group selected from the group [b-1], and one of whose ring-forming methylenes is replaced with a carbonyl group;

An amide compound of the formula (1), wherein $Cy^1$ is a $C_3$-$C_6$ cycloalkyl group optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a $C_2$-$C_6$ cyanoalkyl group and a phenoxy group, and one of whose ring-forming methylenes is replaced with a carbonyl group;

An amide compound of the formula (1), wherein $Cy^1$ is a $C_3$-$C_6$ cycloalkyl group, one of whose ring-forming methylenes is replaced with a carbonyl group;

An amide compound of the formula (1), wherein $Cy^1$ is a cyclohexyl group, one of whose ring-forming methylenes is replaced with a carbonyl group;

An amide compound of the formula (1), wherein $Cy^1$ is a 2-oxocyclohexyl group;

An amide compound of the formula (1), wherein $Cy^1$ is a hydroxyiminocyclohexyl group optionally substituted with at least one group selected from the group [a-1];

An amide compound of the formula (1), wherein $Cy^1$ is a $C_3$-$C_6$ hydroxyiminocycloalkyl optionally substituted with at least one group selected from the group [b-1];

An amide compound of the formula (1), wherein $Cy^1$ is a hydroxyiminocyclohexyl optionally substituted with at least one group selected from the group [b-1];

An amide compound of the formula (1), wherein $Cy^1$ is a $C_3$-$C_6$ hydroxyiminocycloalkyl group optionally substituted with at least one group selected from the group consisting of a $C_1$-$C_6$ alkoxy group, a $C_3$-$C_6$ alkenyloxy group, a $C_1$-$C_6$ haloalkyl group, a $C_1$-$C_6$ haloalkoxy group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl) amino) $C_1$-$C_6$ alkyl group, a $C_2$-$C_6$ cyanoalkyl group and a phenoxy group;

An amide compound of the formula (1), wherein $Cy^1$ is a $C_3$-$C_6$ hydroxyiminocycloalkyl group;

An amide compound of the formula (1), wherein $X^2$ is a hydrogen atom, a halogen atom or a $C_1$-$C_4$ alkoxy group;

An amide compound of the formula (1), wherein $X^2$ is a hydrogen atom, a halogen atom or a $C_1$-$C_4$ alkoxy group, and A is $A^1$-$CR^6R^7R^8$;

An amide compound of the formula (1), wherein $X^2$ is a hydrogen atom or a halogen atom, and A is $A^1$-$CR^6R^7R^8$;

An amide compound of the formula (1), wherein $X^2$ is a hydrogen atom, a halogen atom or a $C_1$-$C_4$ alkoxy group, and A is $A^2$-$Cy^1$;

An amide compound of the formula (1), wherein Z is an oxygen atom, $X^2$ is a hydrogen atom, a halogen atom or a $C_1$-$C_4$ alkoxy group, and A is $A^2$-$Cy^1$;

An amide compound of the formula (1), wherein $X^2$ is a hydrogen atom or a halogen atom, and A is $A^2$-$Cy^1$;

An amide compound of the formula (1), wherein Z is an oxygen atom, $X^2$ is a hydrogen atom or a halogen atom, and A is $A^2$-$Cy^1$;

An amide compound of the formula (1), wherein $X^2$ is a hydrogen atom, a halogen atom, or a $C_1$-$C_4$ alkoxy group, and A is $A^3$-$Cy^2$;

An amide compound of the formula (1), wherein $X^2$ is a hydrogen atom, a halogen atom, or a $C_1$-$C_4$ alkoxy group, A is $A^3$-$Cy^2$, and $A^3$ is a methylene group;

An amide compound of the formula (1), wherein Z is an oxygen atom, $X^2$ is a hydrogen atom, a halogen atom, or a $C_1$-$C_4$ alkoxy group, A is $A^3$-$Cy^2$ and $A^3$ is a methylene group;

An amide compound of the formula (1), wherein $X^2$ is a hydrogen atom, a halogen atom, or a $C_1$-$C_4$ alkoxy group, A is $A^2$-$Cy^1$, and $A^2$ is a single bond, a $CH_2$ group or a $CH(CH_3)$ group;

An amide compound of the formula (1), wherein $X^2$ is a hydrogen atom, a halogen atom, or a $C_1$-$C_4$ alkoxy group, A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group;

An amide compound of the formula (1), wherein A is $A^3$-$Cy^2$;

An amide compound of the formula (1), wherein A is $A^3$-$Cy^2$, $A^3$ is a methylene group substituted with a $C_1$-$C_3$ haloalkyl group or a cyano group, and $Cy^2$ is a $C_3$-$C_6$ cycloalkyl group optionally substituted with at least one group selected from the group [a-2];

An amide compound of the formula (1), wherein A is $A^3$-$Cy^2$, $A^3$ is a methylene group substituted with at least one group selected from the group consisting of a $C_1$-$C_3$ haloalkyl group, a $C_2$-$C_4$ alkenyl group, a $C_2$-$C_4$ alkynyl group, a cyano group and a phenyl group, and $Cy^2$ is a $C_3$-$C_6$ cycloalkyl group optionally substituted with at least one group selected from the following group [b-2], Group [b-2]
a halogen atom, a $C_1$-$C_4$ alkyl group, a $C_2$-$C_4$ alkenyl group, a $C_2$-$C_4$ alkynyl group, a hydroxyl group, a cyano group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a carbamoyl group, a formyl group, a $C_2$-$C_6$ cyanoalkyl group, a $C_1$-$C_3$ alkylsulfonyl group and a phenoxy group;

An amide compound of the formula (1), wherein A is $A^3$-$Cy^2$, $A^3$ is a methylene group substituted with at least one group selected from the group consisting of a $C_1$-$C_3$ haloalkyl group, a $C_2$-$C_4$ alkenyl group, a $C_2$-$C_4$ alkynyl group, a cyano group and a phenyl group, and $Cy^2$ is a cyclohexyl group substituted with at least one group selected from the group [b-2];

An amide compound of the formula (1), wherein A is $A^3$-$Cy^2$, and $A^3$ is a methylene group substituted with at least one group selected from the group consisting of a $C_1$-$C_3$ haloalkyl group, a $C_2$-$C_4$ alkenyl group and a $C_2$-$C_4$ alkynyl group;

An amide compound of the formula (1), wherein A is $A^3$-$Cy^2$, $A^3$ is a methylene group substituted with a $C_1$-$C_3$ haloalkyl group and a cyano group, $Cy^2$ is a $C_3$-$C_6$ cycloalkyl group optionally substituted with at least one group selected from the group [b-2];

An amide compound of the formula (1), wherein A is $A^3$-$Cy^2$, $A^3$ is a methylene group substituted with a $C_1$-$C_3$ haloalkyl group and a cyano group, and $Cy^2$ is a cyclohexyl group optionally substituted with at least one group selected from the group [b-2];

An amide compound of the formula (1), wherein A is $A^3$-$Cy^2$, $A^3$ is a methylene group substituted with a $C_1$-$C_3$ haloalkyl group or a cyano group, and $Cy^2$ is a $C_3$-$C_6$ cycloalkyl group optionally substituted with a $C_1$-$C_4$ alkyl group;

An amide compound of the formula (1), wherein A is $A^3$-$Cy^2$, $A^3$ is a methylene group substituted with a $C_1$-$C_3$ haloalkyl group or a cyano group, and $Cy^2$ is a cyclohexyl group optionally substituted with a $C_1$-$C_4$ alkyl group;

An amide compound of the formula (1), wherein A is $A^3$-$Cy^2$, $A^3$ is a methylene group substituted with a $C_1$-$C_3$ haloalkyl group or a cyano group, and $Cy^2$ is a cyclopentyl group optionally substituted with a $C_1$-$C_4$ alkyl group; and An amide compound of the formula (1), wherein A is $A^3$-$Cy^2$, $A^3$ is a methylene group substituted with a $C_1$-$C_3$ haloalkyl group or a cyano group, and $Cy^2$ is a cyclobutyl group optionally substituted with a $C_1$-$C_4$ alkyl group.

In the present description, the structural formula of the compound may, for the sake of convenience, represent a certain form of an isomer, but the present invention includes all kinds of active isomers arising from the structure of the compound, such as a geometrical isomer, an optical isomer, a stereoisomer, and a tautomeric isomer, and a mixture thereof. Thus, it is not limited to the formula described for the sake of convenience, and can be any single isomer or a mixture thereof. Accordingly, the present compound may have an asymmetric carbon atom in the molecule and may potentially contain an optically active isomer and a racemic isomer, but the present invention is not particularly limited thereto, and includes any cases.

Next, a process for producing the present compound will be explained.

The present compound can be produced by, for example, Production Process 1 to Production process 9 shown hereinafter.

Production Process 1

Among the present compounds, the present compound (5) in which Z is an oxygen atom can be produced by reacting the compound (2) with the compound (3) in the presence of a dehydration condensing agent.

[Chemical Formula 2]

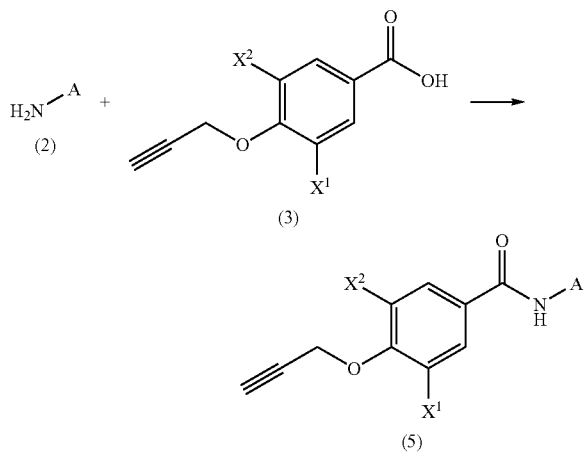

In the formulae, A, $X^1$ and $X^2$ are as defined above.

The reaction is usually carried out in the presence of a solvent.

Examples of the solvent used in the reaction include ethers such as tetrahydrofuran (hereinafter, sometimes, referred to as THF), ethylene glycol dimethyl ether and tert-butyl methyl ether (hereinafter, sometimes, referred to as MTBE), aliphatic hydrocarbons such as hexane, heptanes and octane, aromatic hydrocarbons such as toluene and xylene, halogenated hydrocarbons such as chlorobenzene, esters such as butyl acetate and ethyl acetate, nitriles such as acetonitrile, acid amides such as N,N-dimethylformamide (hereinafter, sometimes, referred to as DMF), sulfoxides such as dimethyl sulfoxide (hereinafter, sometimes, referred to as DMSO), and a mixture thereof.

Examples of the dehydration condensing agent used in the reaction include carbodiimides such as 1-ethyl-3-(3-dimethylaminopropyl)carbodiimide hydrochloride (hereinafter, referred to as WSC) and 1,3-dicyclohexylcarbodiimide.

The compound (3) is used usually in the proportion of 1 to 3 mole, and the dehydration condensing agent is used usually in the proportion of 1 to 5 mole per 1 mole of the compound (2).

The reaction temperature is usually in a range of from 0 to 140° C., and the reaction time is usually in a range of from 1 to 24 hours.

After completion of the reaction, the present compound (5) can be isolated by, after filtration of the reaction mixture, carrying out a post-treatment operation such as extraction of the filtrate with an organic solvent, and drying and concentration of the organic layer. The isolated present compound (5) can be further purified by chromatography, recrystallization or the like.

Production Process 2

Among the present compounds, the present compound (5) in which Z is an oxygen atom can be produced by reacting the compound (2) with the compound (4) in the presence of a base.

[Chemical Formula 3]

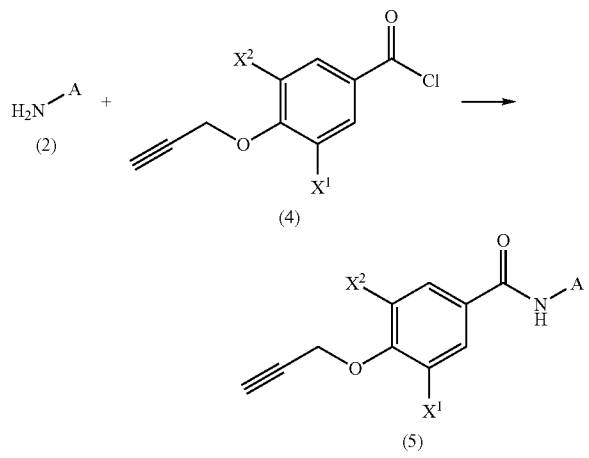

In the formulae, A, $X^1$ and $X^2$ are as defined above.

The reaction is usually carried out in the presence of a solvent.

Examples of the solvent used in the reaction include ethers such as THF, ethylene glycol dimethyl ether and MTBE, aliphatic hydrocarbons such as hexane, heptanes and octane, aromatic hydrocarbons such as toluene and xylene, halogenated hydrocarbons such as chlorobenzene, esters such as butyl acetate and ethyl acetate, nitriles such as acetonitriles, acid amides such as DMF, sulfoxides such as DMSO, and a mixture thereof.

Examples of the base used in the reaction include alkali metal carbonates such as sodium carbonate and potassium carbonate, tertiary amines such as triethyl amine and diisopropylethylamine, and nitrogen-containing aromatic compounds such as pyridine and 4-dimethylaminopyridine.

The compound (4) is used usually in the proportion of 1 to 3 mole, and the base is used usually in the proportion of 1 to 10 mole per 1 mole of the compound (2).

The reaction temperature is usually in a range of from −20 to 100° C., and the reaction time is usually in a range of from 0.1 to 24 hours.

After completion of the reaction, the present compound (5) can be isolated by carrying out a post-treatment operation such as extraction of the reaction mixture with an organic solvent, and drying and concentration of the organic layer, and the like. The isolated present compound (5) can be further purified by chromatography, recrystallization or the like.

Production Process 3

Among the present compounds, the present compound (6) in which Z is a sulfur atom can be produced by reacting the present compound (5) in which Z is an oxygen atom with 2,4-bis(4-methoxyphenyl)-1,3-dithia-2,4-diphosphethane-2,4-disulfide (hereinafter, referred to as Lawesson's reagent).

[Chemical Formula 4]

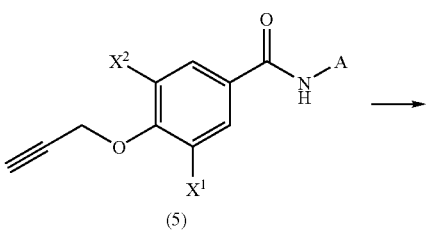

In the formulae, A, $X^1$ and $X^2$ are as defined above.

The reaction is usually carried out in the presence of a solvent.

Examples of the solvent used in the reaction include ethers such as THF, ethylene glycol dimethyl ether and MTBE, aliphatic hydrocarbons such as hexane, heptane and octane, aromatic hydrocarbons such as toluene and xylene, halogenated hydrocarbons such as chlorobenzene, organic nitriles such as acetonitrile and butyronitrile, sulfoxides such as dimethyl sulfoxide, and a mixture thereof.

The Lawesson's reagent is usually used in the proportion of 1 to 2 mole per 1 mole of the present compound (5).

The reaction temperature is usually in a range of from 25 to 150° C., and the reaction time is a usually in a range of from 0.1 to 24 hours.

After completion of the reaction, the present compound (6) can be isolated by carrying out a post-treatment operation such as extraction of the reaction mixture with an organic solvent, and drying and concentration of the organic layer, and the like. The isolated present compound (6) can be further purified by chromatography, recrystallization or the like.

Production Process 4

Among the present compounds, the present compound (9) in which Z is an oxygen atom, and $X^1$ is a fluorine atom can be produced by, first, reacting the compound (7) with the compound (2) in the presence of a base to obtain the compound (8) (step (IV-1)) and, then, reacting the compound (8) with propargyl alcohol in the presence of a base (step (IV-2)).

[Chemical Formula 5]

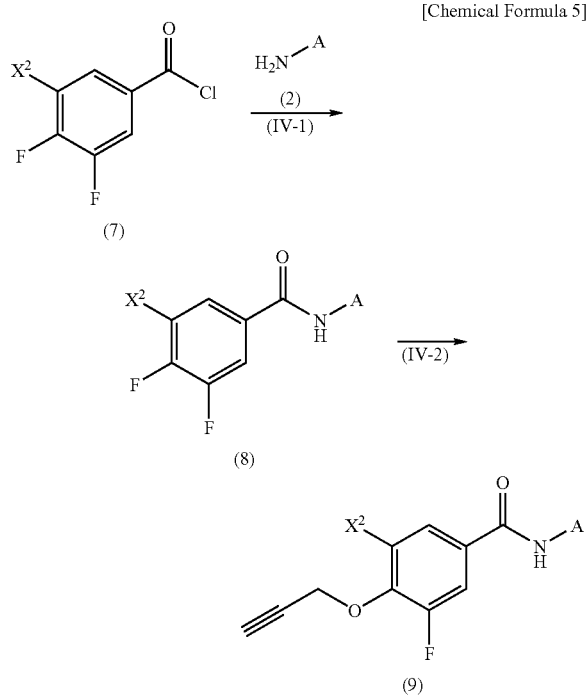

In the formulae, A and $X^2$ are as defined above.

Step (IV-1)

The reaction is usually carried out in the presence of a solvent.

Examples of the solvent used in the reaction include ethers such as THF, ethylene glycol dimethyl ether and MTBE, aliphatic hydrocarbons such as hexane, heptanes and octane, aromatic hydrocarbons such as toluene and xylene, halogenated hydrocarbons such as chlorobenzene, esters such as butyl acetate and ethyl acetate, nitriles such as acetonitrile, acid amides such as DMF, sulfoxides such as dimethyl sulfoxide, and a mixture thereof.

Examples of the base used in the reaction include alkali metal carbonates such as sodium carbonate and potassium carbonate, tertiary amines such as triethylamine and diisopropylethylamine, and nitrogen-containing aromatic compounds such as pyridine and 4-dimethylaminopyridine.

The compound (7) is usually used in the proportion of 1 to 3 mole, and the base is used usually in the proportion of 1 to 10 mole per 1 mole of the compound (2).

The reaction temperature is usually in a range of from −20 to 100° C., and the reaction time is usually in a range of from 0.1 to 24 hours.

After completion of the reaction, the compound (8) can be isolated by carrying out a post-treatment operation such as extraction of the reaction mixture with an organic solvent, and drying and concentration of the organic layer, and the like. The isolated compound (8) can be further purified by chromatography, recrystallization or the like.

Step (IV-2)

The reaction is usually carried out in the presence of a solvent.

Examples of the solvent used in the reaction include ethers such as THF, ethylene glycol dimethyl ether and MTBE, aliphatic hydrocarbons such as hexane, heptanes and octane, ketones such as acetone, methyl ethyl ketone and methyl isobutyl ketone, aromatic hydrocarbons such as toluene and xylene, halogenated hydrocarbons such as chlorobenzene, esters such as butyl acetate and ethyl acetate, nitriles such as acetonitrile, acid amides such as DMF, sulfoxides such as dimethyl sulfoxide, and a mixture thereof.

Examples of the base used in the reaction include alkali metal carbonates such as sodium carbonate and potassium carbonate, alkali metal bicarbonates such as sodium bicarbonate, alkali metal hydrides such as sodium hydride, and alkali metal hydroxides such as sodium hydroxide.

Propargyl alcohol is usually used in the proportion of 1 to 3 mole, and the base is usually used in the proportion of 1 to 2 mole per 1 mole of the compound (8).

The reaction temperature is usually in a range of from −20 to 100° C., and the reaction time is usually in a range of from 0.1 to 24 hours.

After completion of the reaction, the present compound (9) can be isolated by carrying out a post-treatment operation such as extraction of the reaction mixture with an organic solvent, and drying and concentration of the organic layer, and the like. The isolated present compound (9) can be further purified by chromatography, recrystallization or the like.

Production Process 5

Among the present compounds, the present compound (5) in which Z is an oxygen atom can be produced by reacting the compound (10) with propargyl bromide in the presence of a base.

[Chemical Formula 6]

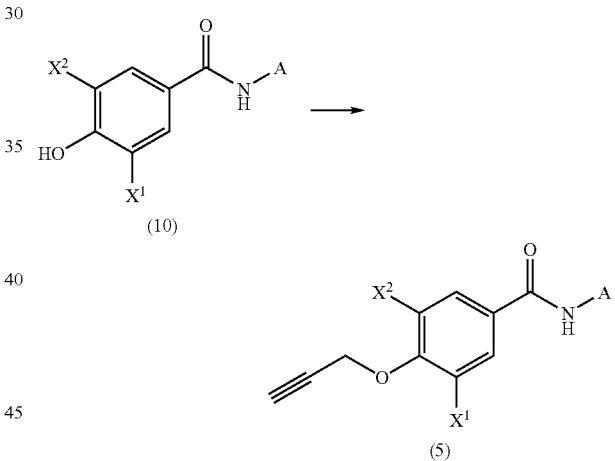

In the formulae, A, $X^1$ and $X^2$ are as defined above.

The reaction is usually carried out in the presence of a solvent.

Examples of the solvent used in the reaction include ethers such as THF, ethylene glycol dimethyl ether and MTBE, aromatic hydrocarbons such as toluene and xylene, halogenated hydrocarbons such as chlorobenzene, nitriles such as acetonitrile, acid amides such as DMF, sulfoxides such as dimethyl sulfoxide, ketones such as acetone, methyl ethyl ketone and methyl isobutyl ketone, water, and a mixture thereof.

Examples of the base used in the reaction include alkali metal carbonates such as sodium carbonate, potassium carbonate and cesium carbonate, alkali metal hydroxides such as sodium hydroxide, and alkali metal hydrides such as sodium hydride.

Propargyl bromide is usually used in the proportion of 1 to 3 mole, and the base is usually used in the proportion of 1 to 3 mole per 1 mole of the compound (10).

The reaction temperature is usually in a range of from −20 to 100° C., and the reaction time is usually in a range of from 0.1 to 24 hours.

After completion of the reaction, the present compound (5) can be isolated by carrying out a post-treatment operation such as extraction of the reaction mixture with an organic solvent, and drying and concentration of the organic layer, and the like. The isolated present compound (5) can be further purified by chromatography, recrystallization or the like.

Production Process 6

Among the present compounds, the present compound (13) in which Z is an oxygen atom, A is $A^2$-$Cy^1$, $A^2$ is a single bond, and $Cy^1$ is a 2-($C_1$-$C_3$ alkylthio)cyclohexyl group, a 2-($C_1$-$C_6$ alkoxy)cyclohexyl group or a 2-phenoxycyclohexyl group can be produced by a process shown in the following scheme.

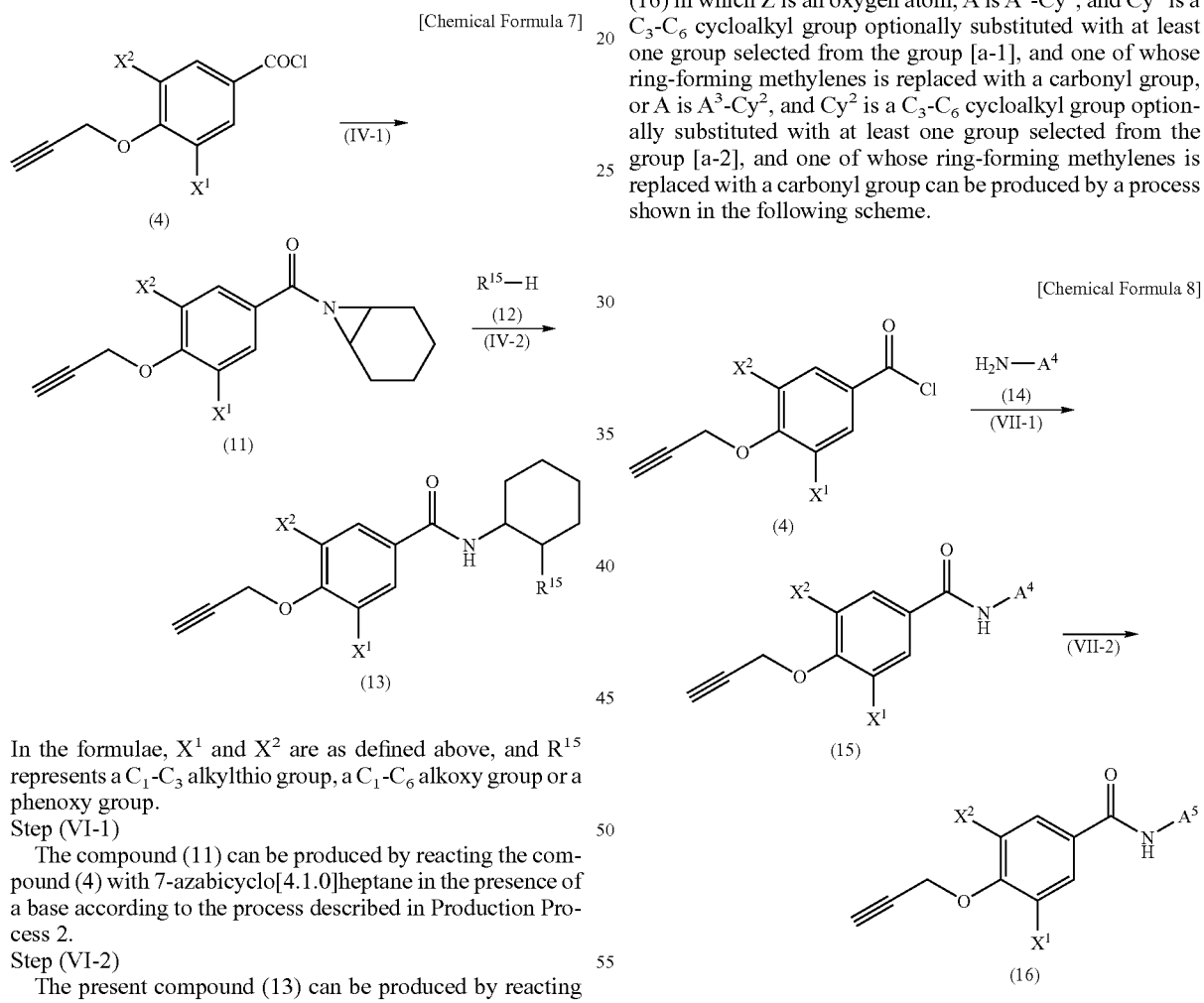

In the formulae, $X^1$ and $X^2$ are as defined above, and $R^{15}$ represents a $C_1$-$C_3$ alkylthio group, a $C_1$-$C_6$ alkoxy group or a phenoxy group.

Step (VI-1)

The compound (11) can be produced by reacting the compound (4) with 7-azabicyclo[4.1.0]heptane in the presence of a base according to the process described in Production Process 2.

Step (VI-2)

The present compound (13) can be produced by reacting the compound (11) with the compound (12).

The reaction is usually carried out in the presence of a solvent.

Examples of the solvent used in the reaction include ethers such as THF, ethylene glycol dimethyl ether, and MTBE, aromatic hydrocarbons such as toluene and xylene, halogenated hydrocarbons such as chlorobenzene and chloroform, esters such as butyl acetate and ethyl acetate, nitriles such as acetonitrile, acid amides such as DMF, and a mixture thereof.

The compound (12) is usually used in the proportion of 1 to 10 mole per 1 mole of the compound (11).

The reaction temperature is usually in a range of from −20 to 150° C., and the reaction time is usually in a range of from 0.1 to 24 hours.

The reaction can be carried out in the presence of an additive, if necessary. Examples of such an additive include a phosphorus compound such as tributylphosphine.

The compound represented by the formula (12) can also be used in the form of an alkali metal salt after reaction thereof with an alkali metal hydride such as sodium hydride.

After completion of the reaction, the present compound (13) can be isolated by carrying out a post-treatment operation such as extraction of the reaction mixture with an organic solvent, and drying and concentration of the organic layer. The isolated present compound (13) can be further purified by chromatography, recrystallization or the like.

Production Process 7

Among the present compounds, the present compound (16) in which Z is an oxygen atom, A is $A^2$-$Cy^1$, and $Cy^1$ is a $C_3$-$C_6$ cycloalkyl group optionally substituted with at least one group selected from the group [a-1], and one of whose ring-forming methylenes is replaced with a carbonyl group, or A is $A^3$-$Cy^2$, and $Cy^2$ is a $C_3$-$C_6$ cycloalkyl group optionally substituted with at least one group selected from the group [a-2], and one of whose ring-forming methylenes is replaced with a carbonyl group can be produced by a process shown in the following scheme.

In the formulae, $A^4$ represents $A^2$-$Cy^{11}$ or $A^3$-$Cy^{21}$, $A^5$ represents $A^2$-$Cy^{12}$ or $A^3$-$Cy^{22}$, $Cy^{11}$ represents a $C_3$-$C_6$ cycloalkyl group optionally substituted with at least one group selected from the group [a-1], and one of whose ring-forming methylenes is replaced with CH(OH), $Cy^{21}$ represents a $C_3$-$C_6$ cycloalkyl group optionally substituted with at least one group selected from the group [a-2], and one of whose ring-forming methylenes is replaced with CH(OH), $Cy^{12}$ represents a $C_3$-$C_6$ cycloalkyl group optionally substituted with at least one group selected from the group [a-1], and one of whose ring-forming methylenes is replaced with a carbonyl group, $Cy^{22}$ represents a $C_3$-$C_6$ cycloalkyl group optionally substituted with at least one group selected from the group [a-2], and one of whose ring-forming methylenes is replaced with a carbonyl group, and $X^1$, $X^2$, $A^2$ and $A^3$ are as defined above.

Step (VII-1)

The compound (15) can be produced by reacting the compound (4) with the compound (14) in the presence of a base according to the process described in Production Process 2.

Step (VII-2)

The present compound (16) can be produced by reacting the compound (15) with an oxidizing agent.

The reaction is usually carried out in the presence of a solvent.

Examples of the solvent used in the reaction include ketones such as acetone, methyl ethyl ketone, and methyl isobutyl ketone, halogenated hydrocarbons such as chloroform, water, and a mixture thereof.

Examples of the oxidizing agent used in the reaction include hypervalent iodine compounds such as bis(acetoxy) phenyl iodide, chromium compounds such as potassium bichromate and chromic acid, halogen oxide compounds such as periodic acid, manganese oxides such as manganese dioxide and potassium permanganate.

The oxidizing agent is usually used in the proportion of 1 to 10 mole per 1 mole of the present compound (15).

The reaction temperature is usually in a range of from −78 to 150° C., and the reaction time is usually in a range of from 0.1 to 24 hours.

After completion of the reaction, the present compound (16) can be isolated by pouring the reaction mixture into water, and carrying out a post-treatment operation such as extraction with an organic solvent, and drying and concentration of the organic layer. The isolated present compound (16) can be further purified by chromatography, recrystallization or the like.

Production Process 8

Among the present compounds, the compound (19) in which Z is an oxygen atom, A is $A^2$-$Cy^1$, $Cy^1$ is a $C_3$-$C_6$ cycloalkyl group substituted with a $C_1$-$C_3$ alkylidene group forming a double bond with the same ring-forming carbon atom, or A is $A^3$-$Cy^2$, and $Cy^2$ is a $C_3$-$C_6$ cycloalkyl group substituted with a $C_1$-$C_3$ alkylidene group forming a double bond with the same ring-forming carbon atom can be produced by reacting the compound (17) with the compound (18) in the presence of a base.

[Chemical Formula 9]

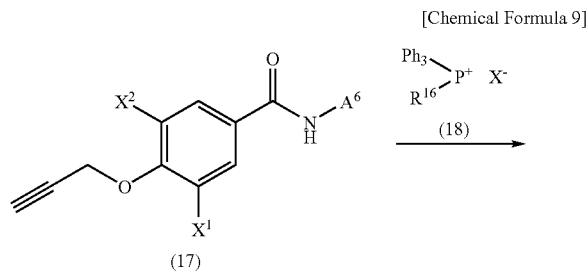

(17)

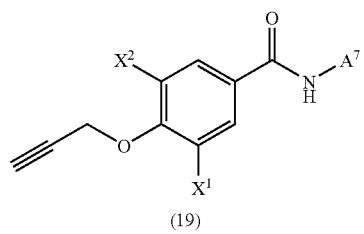

(19)

In the formulae, $A^6$ represents $A^2$-$Cy^{13}$ or $A^3$-$Cy^{23}$, $Cy^{13}$ represents a $C_3$-$C_6$ cycloalkyl group one of whose ring-forming methylenes is replaced with a carbonyl group, $Cy^{23}$ represents a $C_3$-$C_6$ cycloalkyl group one of whose ring-forming methylenes is replaced with a carbonyl group, $A^7$ represents $A^2$-$Cy^{14}$ or $A^3$-$Cy^{24}$, $Cy^{14}$ represents a $C_3$-$C_6$ cycloalkyl group substituted with a $C_1$-$C_3$ alkylidene group forming a double bond with the same ring-forming carbon atom, $Cy^{24}$ represents a $C_3$-$C_6$ cycloalkyl group substituted with a $C_1$-$C_3$ alkylidene group forming a double bond with the same ring-forming carbon atom, $R^{16}$ represents a $C_1$-$C_3$ alkyl group, X represents a chlorine atom, a bromine atom or an iodine atom, and $X^1$, $X^2$, $A^2$ and $A^3$ are as defined above.

The reaction is usually carried out in the presence of a solvent.

Examples of the solvent used in the reaction include ketones such as acetone, methyl ethyl ketone, and methyl isobutyl ketone, halogenated hydrocarbons such as chloroform, water, and a mixture thereof.

Examples of the base used in the reaction include alkali metal salts such as tert-butoxy potassium and n-butyl lithium, and alkali metal hydroxides such as sodium hydroxide.

The compound represented by the formula (18) is usually used in the proportion of 1 to 10 mole, and the base is usually used in the proportion of 1 to 10 mole per 1 mole of the present compound (17).

The reaction temperature is usually in a range of from −78 to 150° C., and the reaction time is usually in a range of from 0.1 to 24 hours.

After completion of the reaction, the present compound (19) can be isolated by carrying out a post-treatment operation such as extraction of the reaction mixture with an organic solvent, and drying and concentration of the organic layer. The isolated present compound (19) can be further purified by chromatography, recrystallization or the like.

Production Process 9

Among the present compounds, the present compound (20) in which Z is an oxygen atom, A is $A^2$-$Cy^1$, and $Cy^1$ is a $C_3$-$C_6$ hydroxyiminocycloalkyl group optionally substituted with at least one group selected from the group [a-1], or A is $A^3$-$Cy^2$, and $Cy^2$ is a $C_3$-$C_6$ hydroxyiminocycloalkyl group optionally substituted with at least one group selected from the group [a-2] can be produced by reacting the compound (16) with hydroxylamine or a salt thereof.

[Chemical Formula 10]

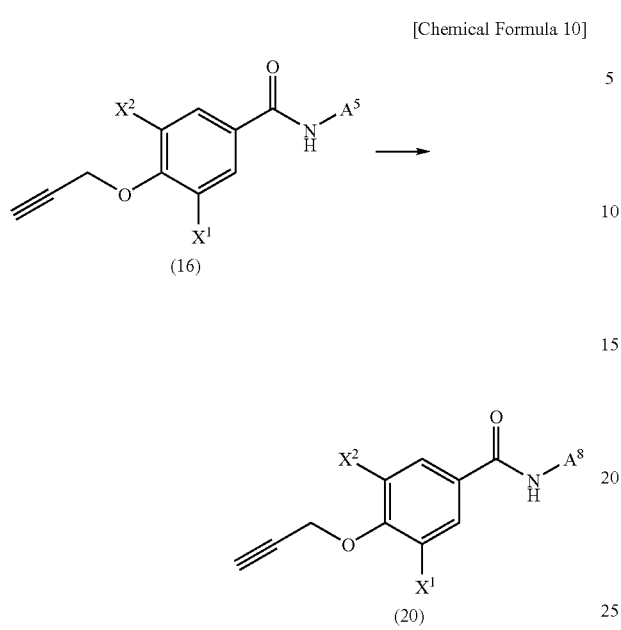

Chemical Formula 11

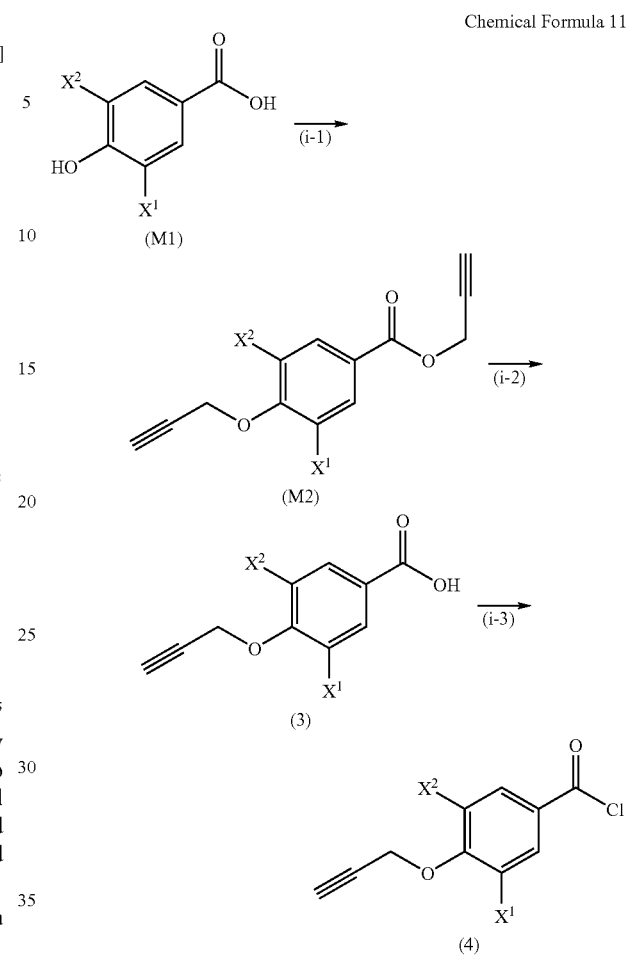

In the formulae, $A^8$ represents $A^2$-$Cy^{15}$ or $A^3$-$Cy^{25}$, $Cy^{15}$ represents a $C_3$-$C_6$ hydroxyiminocycloalkyl group optionally substituted with at least one group selected from the group [a-1], $Cy^{25}$ represents a $C_3$-$C_6$ hydroxyiminocycloalkyl group optionally substituted with at least one group selected from the group [a-2], and $A^2$, $A^3$, $A^5$, $X^1$ and $X^2$ are as defined above.

The reaction is usually carried out in the presence of a solvent.

Examples of the solvent used in the reaction include ethers such as 1,4-dioxane, tetrahydrofuran, and MTBE, aliphatic hydrocarbons such as hexane and heptane, aromatic hydrocarbons such as toluene and xylene, halogenated hydrocarbons such as chlorobenzene, esters such as ethyl acetate, nitriles such as acetonitrile and butyronitrile, acid amides such as DMF, sulfoxides such as dimethyl sulfoxide, alcohols such as methanol and ethanol, water, and a mixture thereof.

Hydroxylamine or a salt thereof is usually used in the proportion of 1 to 5 mole per 1 mole of the compound (16).

The reaction temperature is usually in a range of from 0 to 150° C., and a reaction time is usually in a range of from 0.1 to 24 hours.

After completion of the reaction, the present compound (20) can be isolated by carrying out a post-treatment operation such as extraction of the reaction mixture with an organic solvent, and drying and concentration of the organic layer. The isolated present compound (20) can be further purified by chromatography, recrystallization of the like.

A part of intermediates used in the production of the present compounds are commercially available compounds, or are compounds disclosed in known literatures. Such production intermediates can be produced, for example, by the following processes.

Intermediate Production Process 1

The compound (3) and the compound (4) can be produced by the process shown in the following scheme.

In the formulae, $X^1$ and $X^2$ are as defined above.

Step (i-1)

The compound (M2) can be produced by reacting the compound (M1) with propargyl bromide in the presence of a base.

The reaction is usually carried out in the presence of a solvent.

Examples of the solvent used in the reaction include acid amides such as DMF, and sulfoxides such as DMSO.

Examples of the base used in the reaction include alkali metal carbonates such as sodium carbonate, potassium carbonate and cesium carbonate, and alkali metal hydroxides such as sodium hydroxide.

Propargyl bromide is usually used in the proportion of 2 to 5 mole, and the base is usually used in the proportion of 2 to 5 mole per 1 mole of the compound (M1).

The reaction temperature is usually in a range of from 0 to 140° C., and the reaction time is usually in a range of from 0.5 to 24 hours.

After completion of the reaction, the compound (M2) can be isolated by performing post-treatment operation such as extraction of the reaction mixture with an organic solvent, and drying and concentration of the organic layer. The isolated compound (M2) can be further purified by chromatography, recrystallization or the like.

Step (i-2)

The compound (3) can be produced by hydrolyzing the compound (M2) in the presence of a base.

The reaction is usually carried out in the presence of a solvent.

Examples of the base used in the reaction include alkali metal hydroxides such as sodium hydroxide and potassium hydroxide.

Examples of the solvent used in the reaction include ethers such as tetrahydrofuran, ethylene glycol dimethyl ether and tert-butyl methyl ether, alcohols such as methanol and ethanol, water, and a mixture thereof.

The base is usually used in the proportion of 1 to 10 mole per 1 mole of the compound (M2).

The reaction temperature is usually in a range of from 0 to 120° C., and the reaction time is usually in a range of from 0.5 to 24 hours.

After completion of the reaction, the reaction solution is made acidic and, when a solid is precipitated, the compound (3) can be isolated by filtration, or when a solid is not precipitated, the compound (3) can be isolated by carrying out a post-treatment operation such as extraction of the reaction mixture with an organic solvent, and drying and concentration of the organic layer. The isolated compound (3) can be further purified by chromatography, recrystallization or the like.

Step (i-3)

The compound (4) can be produced by reacting the compound (3) with thionyl chloride.

The reaction is usually carried out in the presence of a solvent.

Examples of the solvent used in the reaction include aliphatic hydrocarbons such as hexane, heptane and octane, aromatic hydrocarbons such as toluene and xylene, nitriles such as acetonitrile, halogenated hydrocarbons such as chlorobenzene, acid amides such as DMF, and a mixture thereof.

Thionyl chloride is usually used in the proportion of 1 to 2 mole per 1 mole of the compound (3).

The reaction temperature is usually in a range of from 20 to 120° C., and the reaction time is usually in a range of from 0.1 to 24 hours.

After completion of the reaction, the compound (4) can be isolated by performing post-treatment operation such as concentration of the reaction mixture. The isolated compound (4) can be further purified by chromatography, recrystallization or the like.

Intermediate Production Process 2

The compound (10) can be produced by the process shown in the following scheme.

Chemical Formula 12

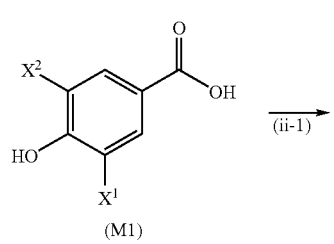

(M1)

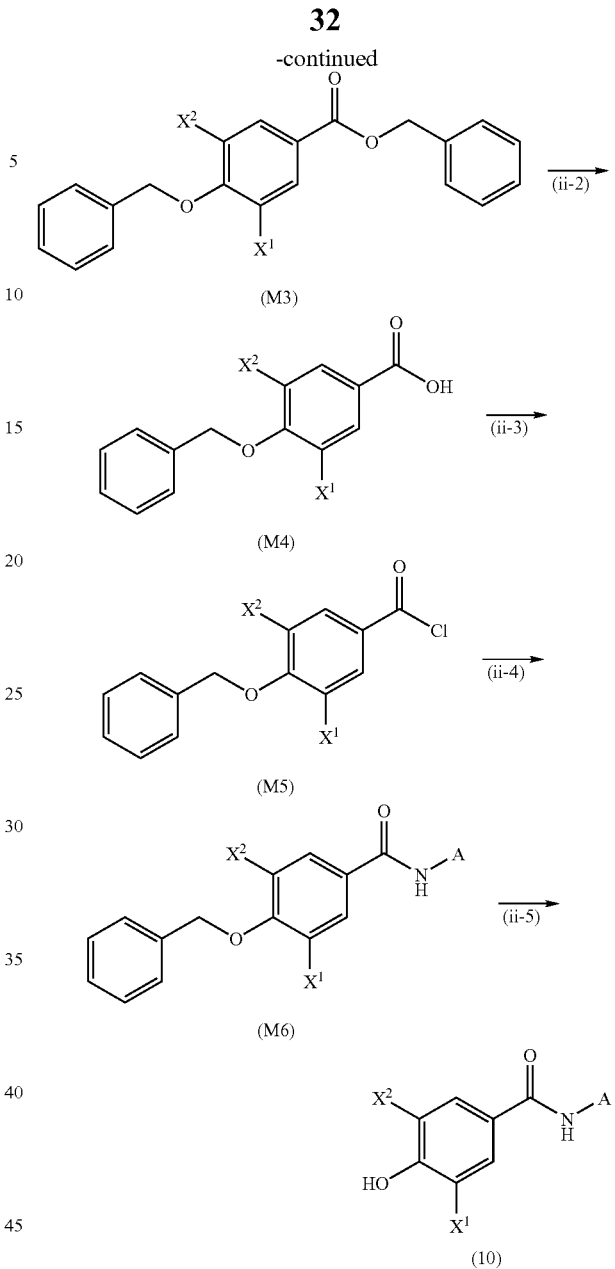

In the formulae, A, $X^1$ and $X^2$ are as defined above.

Step (ii-1)

The compound (M3) can be produced by reacting the compound (M1) with benzyl bromide in the presence of a base.

The reaction is usually carried out in the presence of a solvent.

Examples of the solvent used in the reaction include acid amides such as DMF, and sulfoxides such as DMSO.

Examples of the base used in the reaction include alkali metal carbonates such as sodium carbonate, potassium carbonate and cesium carbonate, and alkali metal hydroxides such as sodium hydroxide.

Benzyl bromide is usually used in the proportion of 2 to 5 mole, and the base is usually used in the proportion of 2 to 5 mole per 1 mole of the compound (M1).

The reaction temperature is usually in a range of from 0 to 140° C., and the reaction time is usually in a range of from 0.5 to 24 hours.

After completion of the reaction, the compound (M3) can be isolated by carrying out a post-treatment operation such as extraction of the reaction mixture with an organic solvent, and drying and concentration of the organic layer. The isolated compound (M3) can be further purified by chromatography, recrystallization or the like.

Step (ii-2)

The compound (M4) can be produced by hydrolyzing the compound (M3) in the presence of a base.

The reaction is usually carried out in the presence of a solvent.

Examples of the base used in the reaction include alkali metal hydroxides such as sodium hydroxide and potassium hydroxide.

Examples of the solvent used in the reaction include ethers such as tetrahydrofuran, ethylene glycol dimethyl ether and MTBE, alcohols such as methanol and ethanol, water, and a mixture thereof.

The base is usually used in the proportion of 1 to 10 mole per 1 mole of the compound (M3).

The reaction temperature is usually in a range of from 0 to 120° C., and the reaction time is usually in a range of from 0.5 to 24 hours.

After completion of the reaction, the reaction solution is made acidic and, when a solid is precipitated, the solid is filtered to isolate the compound (M4) and, when a solid is not precipitated, the compound (M4) can be isolated by carrying out a post-treatment operation such as extraction of the reaction mixture with an organic solvent, and drying and concentration of the organic layer. The isolated compound (M4) can be further purified by chromatography, recrystallization of the like.

Step (ii-3)

The compound (M5) can be produced by reacting the compound (M4) with thionyl chloride.

The reaction is usually carried out in the presence of a solvent.

Examples of the solvent used in the reaction include aliphatic hydrocarbons such as hexane, heptane and octane, aromatic hydrocarbons such as toluene and xylene, nitriles such as acetonitrile, halogenated hydrocarbons such as chlorobenzene, acid amides such as DMF, and a mixture thereof.

Thionyl chloride is usually used in the proportion of 1 to 2 mole per 1 mole of the compound (M4).

The reaction temperature is usually in a range of from 20 to 120° C., and the reaction time is usually in a range of from 0.1 to 24 hours.

After completion of the reaction, the compound (M5) can be isolated by performing post-treatment operation such as concentration of the reaction mixture. The isolated compound (M5) can be further purified by chromatography, recrystallization or the like.

Step (ii-4)

The compound (M6) can be produced by reacting the compound (M5) with the compound (2) in the presence of a base according to the process described in Preparation Process 2.

Step (ii-5)

The compound (10) can be produced by reacting the compound (M6) with hydrogen in the presence of palladium carbon.

The reaction is usually carried out in the presence of a solvent.

Examples of the solvent used in the reaction include aliphatic hydrocarbons such as hexane, heptane and octane, aromatic hydrocarbons such as toluene and xylene, alcohols such as methanol and ethanol, esters such as ethyl acetate, ethers such as THF and MTBE, water, and a mixture thereof.

Palladium carbon is used in the proportion of 0.01 to 0.1 mole, and hydrogen is usually used in the proportion of 1 to 2 mole per 1 mole of the compound (M6).

The reaction temperature is usually in a range of from 0 to 50° C., and the reaction time is usually in a range of from 0.1 to 24 hours.

Pressure of hydrogen used in the reaction is in a range of from normal pressure to 10 atoms.

After completion of the reaction, the compound (10) can be isolated by carrying out a post-treatment operation such as filtration and concentration of the reaction mixture. The isolated present compound (10) can be further purified by chromatography, recrystallization or the like.

Among the compound (3), the compound in which $X^1$ and $X^2$ are a fluorine atom (3,5-difluoro-4-(2-propynyloxy)benzoic acid) can be produced from 3,4,5-trifluorobenzaldehyde by a process described in Intermediate Production Process 3 or Intermediate Production Process 4.

Intermediate Production Process 3

3,5-Difluoro-4-(2-propynyloxy)benzoic acid can be produced by a process shown in the following scheme.

[Chemical Formula 13]

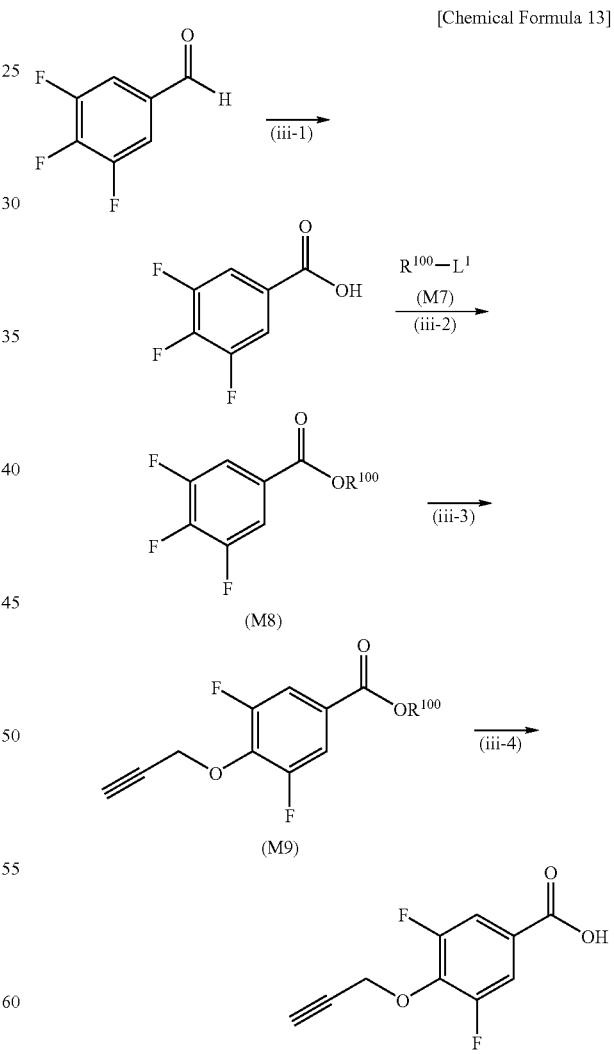

In the formulae, $R^{100}$ represents a C1-C4 alkyl group, a 2-propynyl group or a benzyl group, and $L^1$ represents a chlorine atom, a bromine atom, an iodine atom or a methanesulfonyloxy group.

Step (iii-1)

3,4,5-Trifluorobenzoic acid can be produced by reacting 3,4,5-trifluorobenzaldehyde with an oxidizing agent.

The reaction is usually carried out in the presence of a solvent.

Examples of the solvent used in the reaction include ketones such as acetone, methyl ethyl ketone and methyl isobutyl ketone, nitriles such as acetonitrile, acid amides such as DMF, halogenated hydrocarbons such as chloroform, water, and a mixture thereof.

Examples of the oxidizing agent used in the reaction include potassium permanganate, 3-chloroperbenzoic acid, and a monopersulfate salt compound (OXONE (registered trade mark)).

The oxidizing agent is usually used in the proportion of 1 to 5 mole per 1 mole of 3,4,5-trifluorobenzaldehyde.

The reaction temperature is usually in a range of from 0 to 100° C., and the reaction time is usually in a range of from 0.5 to 24 hours.

After completion of the reaction, 3,4,5-trifluorobenzoic acid can be isolated by carrying out a post-treatment operation such as extraction of the reaction mixture with an organic solvent, and drying and concentration of the organic layer. Isolated 3,4,5-trifluorobenzoic acid can be further purified by chromatography, recrystallization or the like.

Step (iii-2)

The compound (M8) can be produced by reacting 3,4,5-trifluorobenzoic acid with the compound (M7) in the presence of a base.

The reaction is usually carried out in the presence of a solvent.

Examples of the solvent used in the reaction include nitriles such as acetonitrile and the like, acid amides such as DMF, sulfoxides such as DMSO, water, and a mixture thereof.

Examples of the base used in the reaction include alkali metal carbonates such as sodium carbonate, potassium carbonate and cesium carbonate, and alkali metal hydroxides such as sodium hydroxide.

The compound (M7) is usually used in the proportion of 2 to 5 mole, and the base is usually used in the proportion of 2 to 5 mole per 1 mole of 3,4,5-trifluorobenzoic acid.

The reaction temperature is usually in the range of from 0 to 140° C., and the reaction time is usually in a range of from 0.5 to 24 hours.

After completion of the reaction, the compound (M8) can be isolated by carrying out a post-treatment operation such as extraction of the reaction mixture with an organic solvent, drying and concentration of the organic layer. The isolated compound (M8) can be further purified by chromatography, recrystallization or the like.

Step (iii-3)

The compound (M9) can be produced by reacting the compound (M8) with propargyl alcohol in the presence of a base.

The reaction is usually carried out in the presence of a solvent.

Examples of the solvent used in the reaction include nitriles such as acetonitrile, acid amides such as DMF, and sulfoxides such as DMSO.

Examples of the base used in the reaction include alkali metal carbonates such as sodium carbonate, potassium carbonate and cesium carbonate, alkali metal hydroxides such as sodium hydroxide, and alkali metal hydrides such as sodium hydride.

Propargyl alcohol is usually used in the proportion of 1 to 5 mole, and the base is usually used in the proportion of 1 to 5 mole per 1 mole of the compound (M8).

The reaction temperature is usually in a range of from 0 to 140° C., and the reaction time is usually in a range of from 0.5 to 24 hours.

After completion of the reaction, the compound (M9) can be isolated by performing post-treatment operation such as extraction of the reaction mixture with an organic solvent, drying and concentration of the organic layer. Isolated compound (M9) can be further purified by chromatography, recrystallization or the like.

Step (iii-4)

3,5-Difluoro-4-(2-propynyloxy)benzoic acid can be produced by hydrolyzing the compound (M9) in the presence of a base.

The reaction is usually carried out in the presence of a solvent.

Examples of the base used in the reaction include alkali metal hydroxides such as sodium hydroxide and potassium hydroxide.

Examples of the solvent used in the reaction include ethers such as tetrahydrofuran, ethylene glycol dimethyl ether and tert-butyl methyl ether, alcohols such as methanol and ethanol, water, and a mixture thereof.

The base is usually used in the proportion of 1 to 10 mole per 1 mole of the compound (M9).

The reaction temperature is usually in a range of from 0 to 120° C., and the reaction time is usually in a range of from 0.5 to 24 hours.

After completion of the reaction, the reaction solution is made acidic and, thereafter, 3,5-difluoro-4-(2-propynyloxy) benzoic acid can be isolated by carrying out a post-treatment operation such as extraction of the reaction mixture with an organic solvent, drying and concentration of the organic layer. Isolated 3,5-difluoro-4-(2-propynyloxy)benzoic acid can be further purified by chromatography, recrystallization or the like.

Intermediate Production Process 4

3,5-Difluoro-4-(2-propynyloxy)benzoic acid can be produced by a process shown in following scheme.

[Chemical Formula 14]

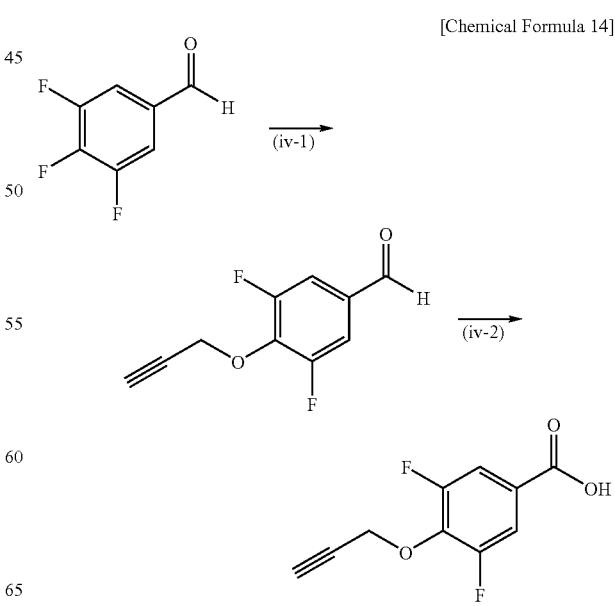

Step (iv-1)

3,5-Difluoro-4-(2-propynyloxy)benzaldehyde can be produced by reacting 3,4,5-trifluorobenzaldehyde and propargyl alcohol in the presence of a base.

The reaction is usually carried out in the presence of a solvent.

Examples of the solvent used in the reaction include hydrocarbons such as toluene, nitriles such as acetonitrile, acid amides such as DMF, sulfoxides such as DMSO, ketones such as acetone, methyl ethyl ketone and methyl isobutyl ketone, water, and a mixture thereof.

Examples of the base used in the reaction include alkali metal carbonates such as sodium carbonate, potassium carbonate and cesium carbonate, alkali metal hydroxides such as sodium hydroxide, and alkali metal hydrides such as sodium hydride.

Propargyl alcohol is usually used in the proportion of 1 to 5 mole, and the base is usually used in the proportion of 1 to 5 mole per 1 mole of 3,4,5-trifluorobenzaldehyde.

The reaction temperature is usually in a range of from 0 to 100° C., and the reaction time is usually in a range of from 0.5 to 24 hours.

After completion of a reaction, 3,5-difluoro-4-(2-propynyloxy)benzaldehyde can be isolated by carrying out a post-treatment operation such as extraction of the reaction mixture with an organic solvent, drying and concentration of the organic layer and the like. Isolated 3,5-difluoro-4-(2-propynyloxy)benzaldehyde can be further purified by chromatography, recrystallization or the like.

Step (iv-2)

3,5-Difluoro-4-(2-propynyloxy)benzoic acid can be produced by reacting 3,5-difluoro-4-(2-propynyloxy)benzaldehyde and an oxidization agent.

The reaction is usually carried out in the presence of a solvent.

Examples of the solvent used in the reaction include ketones such as acetone, methyl ethyl ketone and isobutyl ketone, nitriles such as acetonitrile, acid amides such as DMF, halogenated hydrocarbons such as chloroform, water, and a mixture thereof.

Examples of the oxidizing agent used in the reaction include potassium permanganate, 3-chloroperbenzoic acid, and monopersulfate salt compound (OXONE (registered trademark)).

The oxidizing agent is usually used in the proportion of 1 to 3 mole per 1 mole of 3,5-difluoro-4-(2-propynyloxy)benzaldehyde.

The reaction temperature is usually in a range of from 0 to 100° C. and the reaction time is usually in a range of from 0.5 to 24 hours.

After completion of the reaction, 3,5-difluoro-4-(2-propynyloxy)benzoic acid can be isolated by performing post-treatment operation such as extraction of the reaction mixture with an organic solvent, drying and concentration of the organic layer and the like. Isolated 3,5-difluoro-4-(2-propynyoxy) benzoic acid can be further purified by chromatography, recrystallization or the like.

As embodiments of a compound represented by the formula (10):

[Chemical Formula 15]

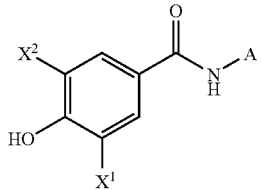

(10)

wherein $X^1$, $X^2$ and A are as defined above, which is an intermediate for producing the present compound, for example, the following compounds are listed.

The compound of the formula (10), wherein $X^1$ is a fluorine atom;

The compound of the formula (10), wherein $X^1$ is a methoxy group;

The compound of the formula (10), wherein $X^1$ is a fluorine atom, and $X^2$ is a hydrogen atom;

The compound of the formula (10), wherein $X^1$ is a fluorine atom, and $X^2$ is a fluorine atom;

The compound of the formula (10), wherein $X^1$ is a methoxy group, and $X^2$ is a hydrogen atom; and The compound of the formula (10), wherein $X^1$ is a methoxy group, and $X^2$ is a methoxy group.

Plant diseases against which the present compound exerts an excellent effect include those caused by fungi, bacteria and viruses. Specific examples of the fungi include genus *Erysiphe* such as wheat powdery mildew (*Erysiphe graminis*), genus *Uncinula* such as grape powdery mildew (*Uncinula necator*), genus *Podosphaera* such as apple powdery mildew (*Podosphaera leucotricha*), genus *Sphaerotheca* such as cucumber powdery mildew (*Sphaerotheca cucurbitae*), genus *Oidiopsis* such as tomato powdery mildew (*Oidiopsis sicula*), genus *Magnaporthe* such as rice blast (*Magnaporthe oryzae*), genus *Cochliobolus* such as rice brown spot (*Cochliobolus miyabeanus*), genus *Mycosphaerella* such as wheat leaf blotch (*Mycosphaerella graminicola*), genus *Pyrenophora* such as barley net blotch (*Pyrenophora teres*), genus *Stagonospora* such as wheat Glume blotch (*Stagonospora nodorum*), genus *Rhynchosporium* such as barley scald disease (*Rhynchosporium secalis*), genus *Pseudocercosporella* such as wheat eyespot (*Pseudocercosporella herpotrichoides*), genus *Gaeumannomyces* such as wheat take-all (*Gaeumannomyces graminis*), genus *Fusarium* such as wheat *Fusarium* head bright (*Fusarium* spp.), genus *Microdochium* such as wheat snow mold (*Microdochium nivale*), genus *Venturia* such as apple scab (*Venturia inaequalis*), genus *Elsinoe* such as grape antracnose (*Elsinoe ampelina*), genus *Botrytis* such as cucumber gray mold (*Botrytis cinerea*), genus *Monilinia* such as peach brown rot (*Monilinia fructicola*), genus *Phoma* such as rape stem canker (*Phoma lingam*), genus *Cladosporium* such as tomato leaf mold (*Cladosporium fulvum*), genus *Cercospora* such as sugarbeet brown spot (*Cercospora beticola*), genus *Cercosporidium* such as peanut late leaf spot (*Cercosporidium personatum*), genus *Colletotrichum* such as strawberry anthracnose (*Colletotrichum fragariae*), genus *Sclerotinia* such as cucumber stem rot (*Sclerotinia sclerotiorum*), genus *Alternaria* such as apple necrotic leaf spot (*Alternaria mali*), genus *Verticillium* such as eggplant *Verticillium* wilt (*Verticillium dahliae*), genus *Rhizoctonia* such as rice sheath blight (*Rhizoctonia*

*solani*), genus *Puccinia* such as wheat leaf rust (*Puccinia recondita*), genus *Phakopsora* such as soybean rust (*Phakopsora pachyrhizi*), genus *Tilletia* such as wheat bunt (*Tilletia caries*), genus *Ustilago* such as barley loose smut (*Ustilago nuda*), genus *Sclerotium* such as peanut southern blight (*Sclerotium rolfsii*), genus *Phytophthora* such as potato late blight (*Phytophthora infestans*), genus *Pseudoperonospora* such as cucumber downy mildew (*Pseudoperonospora cubensis*), genus *Peronospora* such as Chinese cabbage downy mildew (*Peronospora parasitica*), genus *Plasmopara* such as grape downy mildew (*Plasmopara viticola*), genus *Sclerophthora* such as rice downy mildew (*Sclerophthora macrospora*), genus *Pythium* such as cucumber seedling damping-off (*Pythium ultimum*), and genus *Plasmodiophora* such as rapeseed clubroot (*Plasmodiophora brassicae*). Examples of bacteria include genus *Burkholderia* such as bacterial rice seedling blight (*Burkholderia plantarii*), genus *Pseudomonas* such as bacterial cucumber leaf spot (*Pseudomonas syringae* pv. *Lachrymans*), genus *Ralstonia* such as eggplant wilting (*Ralstonia solanacearum*), genus *Xanthomonas* such as Asiatic citrus canker (*Xanthomonas citiri*), and genus *Erwinia* such as Chinese cabbage bacterial soft rot (*Erwinia carotovora*). Examples of viruses include Tobacco mosaic virus and Cucumber mosaic virus. However, the sterilizing spectra should not be limited thereto in any cases.

The plant disease control agent of the present invention can be the present compound itself, but usually, it is used in the form of formulations such as emulsifiable concentrates, wettable powders, granular wettable powders, flowable formulations, dusts and granules produced by mixing it with solid carriers, liquid carriers, surface active agents and other adjuvants for formulations. These formulations usually contain the present compound in an amount of 0.1% to 90% by weight.

Examples of the solid carriers used in the formulations include fine powders or particles of minerals such as kaolin clay, attapulgite clay, bentonite, montmorillonite, acid clay, pyrophyllite, talc, diatomaceous earth, calcite and the like; natural organic substances such as corncob powder, walnut shell flour and the like; synthetic organic substances such as urea and the like; salts such as calcium carbonate, ammonium sulfate and the like; and synthetic inorganic substances such as synthetic hydrated silicon oxide and the like. Examples of the liquid carriers include aromatic hydrocarbons such as xylene, alkylbenzene, methylnaphthalene and the like; alcohols such as 2-propanol, ethylene glycol, propylene glycol, cellosolve and the like; ketones such as acetone, cyclohexanone, isophorone and the like; vegetable oils such as soybean oil, cotton seed oil and the like; petroleum aliphatic hydrocarbons; esters; and dimethyl sulfoxide, acetonitrile and water.

Examples of the surfactant include anionic surfactants such as alkyl sulfate, alkyl aryl sulfonate, dialkyl sulfosuccinate, polyoxyethylene alkyl aryl ether phosphate, ligninsulfonate, a naphthalenesulfonate formaldehyde polycondensate and the like; and nonionic surfactants such as polyoxyethylene alkyl aryl ether, a polyoxyethylene alkylpolyoxypropylene block copolymer, sorbitan fatty acid ester and the like.

Examples of the adjuvant for formulation include water-soluble polymers such as polyvinyl alcohol, polyvinyl pyrrolidone and the like; polysaccharides such as gum Arabic, alginic acid and a salt thereof, CMC (carboxymethyl cellulose), xanthan gum and the like; inorganic substances such as aluminum magnesium silicate, alumina sol and the like; preservatives; colorants; PAP (acidic isopropyl phosphate); and stabilizers such as BHT and the like.

The plant disease control agent of the present invention is used for treating plants to protect the plants from plant diseases, and is also used for treating soil to protect plants growing in the soil from plant diseases.

When the plant disease control agent of the present invention is used by subjecting plants to a foliage treatment or used by treating soil, its application amount varies depending upon the kind of crops as plants to be protected, the kind of diseases to be controlled, severity of diseases, form of the formulation, time of application, weather conditions and the like. The total amount of the present compound is usually within a range of from 1 to 5,000 g, and preferably from 5 to 1,000 g per 10,000 m$^2$.

Emulsifiable concentrates, wettable powders and flowable formulations are usually used for treatment by spraying after dilution with water. In this case, the concentration of the present compound is usually within a range from 0.0001 to 3% by weight, and preferably from 0.0005 to 1% by weight. Dusts and granules are usually used for a treatment without being diluted.

The plant disease control agent of the present invention can be used by a treating method such as seed disinfection. Examples of the method include a method of immersing seeds of plants in the plant disease control agent of the present invention in which the concentration of the present compound is adjusted within a range from 1 to 1,000 ppm, a method of spraying or smearing, the plant disease control agent of the present invention in which the concentration of the present compound is adjusted within a range from 1 to 1,000 ppm, on seeds of plants, and a method of dust coating of seeds of plants using the plant disease control agent of the present invention.

The plant disease control method of the present invention is usually carried out by treating a plant in which onset of diseases is presumed, or soil where the plant is growing, with an effective amount of the plant disease control agent of the present invention, and/or treating a plant in which onset of diseases has been confirmed, or the soil where the plants are growing.

The plant disease control agent of the present invention can be used as a control agent for plant diseases in crop lands such as upland fields, paddy fields, lawn, and orchards, etc. The plant disease control agent can control plant diseases in crop lands where the following "crops" or the like are cultivated.

Field crops: corn, rice, wheat, barley, rye, oat, sorghum, cotton, soybean, peanut, buckwheat, beet, rape, sunflower, sugar cane, tobacco, etc.

Vegetables: Solanaceae (e.g. eggplant, tomato, green pepper, pepper and potato), Cucurbitaceae (e.g. cucumber, pumpkin, zucchini, watermelon and melon), Cruciferae (e.g. Japanese radish, turnip, horseradish, kohlrabi, Chinese cabbage, cabbage, leaf mustard, broccoli and cauliflower), Compositae (e.g. edible burdock, garland chrysanthemum, globe artichoke and lettuce), Liliacede (e.g. Welsh onion, onion, garlic and asparagus), Umbelliferae (e.g. carrot, parsley, celery and Pastinaca), Chenopodiales (e.g. spinach and chard), Lamiaceae (e.g. perilla, mint and basil), strawberry, sweet potato, Chinese yam, taro, etc.

Flowers and ornament plants.

Ornamental foliage plants.

Fruit trees: pomaceous fruits (e.g. apple, pear, Japanese pear, Chinese quince and quince), stone fruits (e.g. peach, plum, nectarine, Japanese apricot, cherry, apricot and prune), citrus fruits (e.g. Satsuma mandarin, orange, lemon, lime and grapefruit), nut trees (e.g. chestnut, walnut, hazel, almond, pistachio, cashew nut and macadamia nut), berries (e.g. blueberry, cranberry, blackberry and raspberry), grape, Japanese persimmon, olive, loquat, banana, coffee, date palm, coconut palm, etc.

Trees other than fruit trees: tea, mulberry, flowering trees and shrubs, street trees (Japanese ash, birch, flowering dogwood, blue gum, ginkgo, lilac, maple, oak, poplar, Chinese redbud, Formosa sweet gum, plane trees, zelkova, Japanese arborvitae, fir, Japanese hemlock, needle juniper, pine, Japanese spruce and Japanese yew).

The above-mentioned "crops" also include crops having resistance to herbicides such as HPPD inhibitors (e.g. isoxaflutol), ALS inhibitors (e.g. imazethapyr and thifensulfuron-methyl), EPSP synthetase inhibitors, glutamine synthetase inhibitors, bromoxynil, etc. which has been imparted by a classic breeding method or a gene engineering technology.

Examples of the "crops" having the resistance imparted by the classic breeding method include Clearfield® canola resistant to imidazolinone herbicides (e.g. imazethapyr) and STS soybean resistant to sulfonylurea ALS inhibition type herbicides (e.g. thifensulfuron-methyl). As crops having the resistance imparted by the gene engineering technology, corn cultivars resistant to glyphosate and glufosinate are exemplified and are already on the market under the trade names such as RoundupReady® and LibertyLink®.

The above-mentioned "crops" also include crops which have been enabled by the gene engineering technology to synthesize a selective toxin known in the case of, for example, *Bacillus*.

Examples of toxins produced in such gene engineered plants include insecticidal proteins derived from *Bacillus cereus* and *Bacillus popilliae*; insecticidal proteins such as δ-endotoxins (e.g. Cry1Ab, Cry1Ac, Cry1F, Cry1Fa2, Cry2Ab, Cry3A, Cry3Bb1 and Cry9C) derived from *Bacillus thuringiensis*, VIP1, VIP2, VIP3, VIP3A, etc.; toxins derived from nematodes; toxins produced by animals, such as scorpion toxin, spider toxin, bee toxin, insect-specific neurotoxins, etc.; fungi toxins; plant lectins; agglutinin; protease inhibitors such as trypsin inhibitors, serine protease inhibitors, patatin, cystatin, papain inhibitors, etc.; ribosome-inactivating proteins (RIPs) such as ricin, corn-RIP, abrin, rufin, sapolin, briodin, etc.; steroid metabolic enzymes such as 3-hydroxysteroid oxidase, ecdysteroid-UDP-glucosyltransferase, cholesterol oxidase, etc.; ecdysone inhibitors; HMG-COA reductase; ion channel inhibitors such as sodium channel inhibitors, calcium channel inhibitors, etc.; juvenile hormone esterase; diuretic hormone receptors; stilbene synthetase; bibenzyl synthetase; chitinase; and glucanase.

The toxins produced in such gene engineered crops also include hybrid toxins of insecticidal proteins such as δ-endotoxin proteins (e.g. Cry1Ab, Cry1Ac, Cry1F, Cry1Fa2, Cry2Ab, Cry3A, Cry3Bb1 and Cry9C), VIP1, VIP2, VIP3, VIP3A, etc., partly deficient toxins and modified toxins. The hybrid toxins are produced by a novel combination of the different domains of such proteins by adopting a gene engineering technology. As the partly deficient toxin, Cry1Ab deficient in a part of the amino acid sequence is known. In the modified toxins, one or more amino acids of a natural toxin have been replaced.

Examples of such toxins and gene engineered plants capable of synthesizing such toxins are described in EP-A-0 374 753, WO 93/07278, WO 95/34656, EP-A-0 427 529, EP-A-451 878, WO 03/052073, etc.

The toxins contained in such genetically engineered plants impart resistance to insect pests of Coleoptera, Diptera and Lepidoptera to the plants.

Gene engineered plants containing one or more insecticidal insect-resistant genes and capable of producing one or more toxins have already been known, and some of them are on the market. Examples of such genetically modified plants include YieldGard® (a corn cultivar capable of producing Cry1Ab toxin), YieldGard Rootworm® (a corn cultivar capable of producing Cry3Bb1 toxin), YieldGard Plus® (a corn cultivar capable of producing Cry1Ab and Cry3Bb1 toxins), Herculex I® (a corn cultivar capable of producing phosphinotrysin N-acetyltransferase (PAT) for imparting resistance to Cry1Fa2 toxin and Glyfosinate), NuCOTN33B (a cotton cultivar capable of producing Cry1Ac toxin), Bollgard I® (a cotton cultivar capable of producing Cry1Ac toxin), Bollgard II® (a cotton cultivar capable of producing Cry1Ac and Cry2Ab toxins), VIPCOT® (a cotton cultivar capable of producing VIP toxin), NewLeaf® (a potato cultivar capable of producing Cry3A toxin), NatureGard®, Agrisure® GT Advantage (GA21 glyphosate resistant properties), Agrisure® CB Advantage (Bt11 corn borer (CB) properties), and Protecta®.

The above-mentioned "crops" also include crops having an ability to produce an anti-pathogenic substance having a selective action which has been imparted by a gene engineered technology.

As examples of the anti-pathogenic substance, PR proteins and the like are known (PRPs, EP-A-0 392 225). Such anti-pathogenic substances and gene engineered plants capable of producing them are described in EP-A-0 392 225, WO 95/33818, EP-A-0 353 191, and the like.

Examples of such anti-pathogenic substances produced by the gene engineered plants include ion channel inhibitors such as sodium channel inhibitors, calcium channel inhibitors (for example, KP1, KP4 and KP6 toxins produced by viruses are known), etc.; stilbene synthase; bibenzyl synthase; chitinase; glucanase; PR proteins; and anti-pathogenic substances produced by microorganisms, such as peptide antibiotics, antibiotics having a heterocyclic ring, protein factors concerned in resistance to plant diseases (which are called plant-disease-resistant genes and are described in WO 03/000906), etc.

It is also possible to use the plant disease control agent of the present invention after mixing with other fungicides, insecticides, acaricides, nematocides, herbicides, plant growth regulators, fertilizers or soil conditioners, or to use the agent and them simultaneously without mixing them. Examples of the active ingredients of the plant disease control agent include chlorothalonil, fluazinam, dichlofluanid, fosetyl-Al, cyclic imide derivatives (e.g., captan, captafol, folpet, etc.), dithiocarbamate derivatives (e.g., maneb, mancozeb, thiram, ziram, zineb, propineb, etc.), inorganic or organic copper derivatives (e.g., basic copper sulfate, basic copper chloride, copper hydroxide, oxine-copper, etc.), acylalanine derivatives (e.g., metalaxyl, furalaxyl, ofurace, cyprofuram, benalaxyl, oxadixyl, etc.), strobilurin compounds (e.g., kresoxim-methyl, azoxystrobin, trifloxystrobin, picoxystrobin, pyraclostrobin, fluoxastrobin, metominostrobin, oryzastrobin, enestrobin, dimoxystrobin, etc.), anilinopyrimidine derivatives (e.g., cyprodinil, pyrimethanil, mepanipyrim, etc.), phenylpyrrol derivatives (e.g., fenpiclonil, fludioxonil, etc.), imide derivatives (e.g., procymidone, iprodione, vinclozolin, etc.), benzimidazole derivatives (e.g., carbendazim, benomyl, thiabendazole and thiophanate-methyl, etc.), amine derivatives (e.g., fenpropimorph, tridemorph, fenpropidine, spiroxamine, etc.), azole derivatives (e.g., propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol, ipconazole, pefurazoate, prothioconazole, etc.), triforine, pyrifenox, fenarimol, propamocarb, cymoxanil, dimethomorph, flumorph, famoxadone, fenamidone, pyribencarb, iprovaricarb, benthiavalicarb, mandipropamid, cyazofamid, amisulbrom, zoxamide, ethaboxam, boscalid, penthiopyrad, fluopyram, bixafen, carboxin, oxycarboxin, thifluzamide, flutolanil, mepronil, furametpyr, pencycuron, hymexazol, etridiazole, ferimzone, silthiofam, blasticidin S, kasugamycin, streptomycin, pyrazophos, iprobenfos, edifenphos, isoprothiolane, fthalide, pyroquilon, tricyclazole, carpropamid, diclocymet, fenoxanil, probenazole, tiadinil, isotianil, iminoctadine, guazatine, tolnifanide, tolclofos-methyl, fenhexamid, polyoxin B, quinoxyfen, proquinazid, metrafenone, cyflufenamide, diethofencarb, fluopicolide, and acibenzolar-S-methyl.

EXAMPLES

The present invention will be explained in more detail by way of Production Examples, Formulation Examples and Test Examples, but the present invention is not limited thereto.

First, Production Examples of the present compound will be shown.

Production Example 1

To 5 ml of THF were added 0.35 g of 3,5-difluoro-4-(2-propynyloxy)benzoyl chloride, 0.50 g of 2-hydroxy-1,2-dimethylpropylamine and 0.50 g of triethylamine, and the mixture was stirred at room temperature for 2 hours. The reaction mixture was subjected to silica gel column chromatography, and 0.48 g of N-(2-hydroxy-1,2-dimethylpropyl)-3,5-difluoro-4-(2-propynyloxy)benzamide (hereinafter referred to as the present compound 1) was obtained.

The Present Compound 1

[Chemical Formula 16]

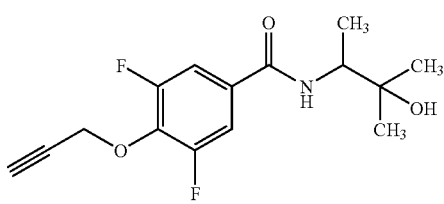

$^1$H-NMR (CDCl$_3$) δ: 1.25 (3H, d, J=6.8 Hz), 1.28 (6H, s), 2.00 (1H, s), 2.52 (1H, t, J=2.4 Hz), 4.08-4.15 (1H, m), 4.88 (2H, d, J=2.4 Hz), 6.39 (1H, d, J=8.0 Hz), 7.34-7.41 (2H, m).

Production Example 2

According to the same process as that described in Production Example 1, N-(2-hydroxy-1,2-dimethylpropyl)-3-methoxy-4-(2-propynyloxy)benzamide (hereinafter referred to as the present compound 2) was obtained except for using 3-methoxy-4-(2-propynyloxy)benzoyl chloride in place of 3,5-difluoro-4-(2-propynyloxy)benzoyl chloride.

The Present Compound 2

[Chemical Formula 17]

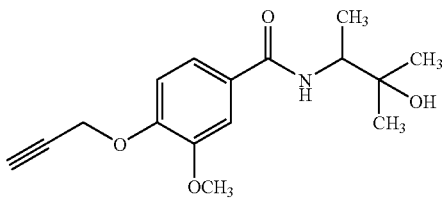

$^1$H-NMR (CDCl$_3$) δ: 1.25 (3H, J=7.0 Hz), 1.26 (3H, s), 1.28 (3H, s), 2.54 (1H, t, J=2.4 Hz), 3.91 (3H, s), 4.06-4.15 (1H, m), 4.80 (2H, d, J=2.4 Hz), 6.53-6.56 (1H, br m), 7.00 (1H, d, J=8.5 Hz), 7.29 (1H, dd, J=8.5, 2.0 Hz), 7.46 (1H, d, J=2.0 Hz).

Production Example 3

According to the same process as that described in Production Example 1, N-(2-hydroxy-2-methylpropyl)-3,5-difluoro-4-(2-propynyloxy)benzamide (hereinafter referred to as the present compound 3) was obtained except for using 2-hydroxy-2-methylpropylamine in place of 2-hydroxy-1,2-dimethylpropylamine.

The Present Compound 3

[Chemical Formula 18]

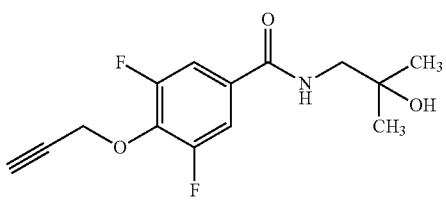

$^1$H-NMR (CDCl$_3$) δ: 1.29 (6H, s), 2.11 (1H, s), 2.52 (1H, t, J=2.4 Hz), 3.46 (2H, d, J=6.0 Hz), 4.88 (2H, d, J=2.4 Hz), 6.57 (1H, br s), 7.36-7.43 (2H, m).

Production Example 4

According to the same process as that described in Production Example 1, N-(2-hydroxy-2-methylpropyl)-3-methoxy-4-(2-propynyloxy)benzamide (hereinafter referred to as the present compound 4) was obtained except for using 2-hydroxy-2-methylpropylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 4

[Chemical Formula 19]

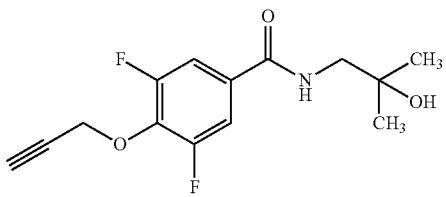

$^1$H-NMR (CDCl$_3$) δ: 1.29 (6H, s), 2.38 (1H, s), 2.53 (1H, t, J=2.4 Hz), 3.47 (2H, d, J=6.0 Hz), 3.93 (3H, s), 4.82 (2H, d,

J=2.4 Hz), 6.55 (1H, br s), 7.04 (1H, d, J=8.5 Hz), 7.30 (1H, dd, J=8.5, 1.7 Hz), 7.47 (1H, J=1.7 Hz).

Production Example 5

According to the same process as that described in Production Example 1, N-(3-hydroxy-2,2-dimethylpropyl)-3,5-difluoro-4-(2-propynyloxy)benzamide (hereinafter referred to as the present compound 5) was obtained except for using 3-hyroxy-2,2-dimethylpropylamine in place of 2-hydroxy-1,2-dimethylpropylamine.

The Present Compound 5

[Chemical Formula 20]

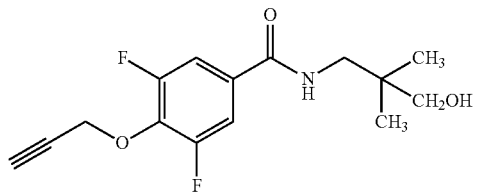

$^1$H-NMR (CDCl$_3$) δ: 0.95 (6H, s), 2.52 (1H, t, J=2.4 Hz), 3.30 (2H, d, J=6.4 Hz), 3.32 (2H, d, J=6.4 Hz), 3.56 (1H, t, J=6.4 Hz), 4.88 (2H, d, J=2.4 Hz), 6.89 (1H, br s), 7.34-7.41 (2H, m).

Production Example 6

According to the same process as that described in Production Example 1, N-(2-amino-2-methylpropyl)-3,5-difluoro-4-(2-propynyloxy)benzamide (hereinafter, referred to as the present compound 6) was obtained except for using 2-amino-2-methylpropylamine in place of 2-hydroxy-1,2-dimethylpropylamine.

The Present Compound 6

[Chemical Formula 21]

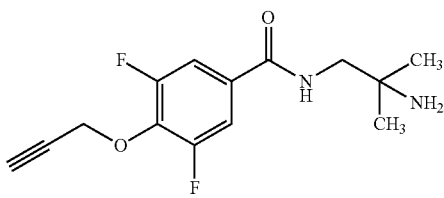

$^1$H-NMR (CDCl$_3$) δ: 1.18 (6H, s), 1.41 (2H, br s), 2.52 (1H, t, J=2.4 Hz), 3.30 (2H, d, J=5.6 Hz), 4.88 (2H, d, J=2.4 Hz), 6.83 (1H, br s), 7.36-7.44 (2H, m).

Production Example 7

According to the same process as that described in Production Example 1, N-{1-(hydroxymethyl)cyclohexyl}methyl-3,5-difluoro-4-(2-propynyloxy)benzamide (hereinafter referred to as the present compound 7) was obtained except for using 1-{1-(hydroxymethyl)cyclohexyl}methylamine in place of 2-hydroxy-1,2-dimethylpropylamine.

The Present Compound 7

[Chemical Formula 22]

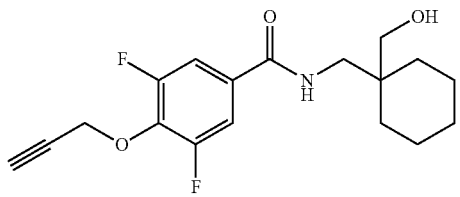

$^1$H-NMR (CDCl$_3$) δ: 1.30-1.53 (10H, m), 2.52 (1H, t, J=2.4 Hz), 3.19 (1H, t, J=6.4 Hz), 3.42 (2H, d, J=6.3 Hz), 3.45 (2H, d, J=6.3 Hz), 4.88 (2H, d, J=2.4 Hz), 6.76-6.81 (1H, m), 7.33-7.40 (2H, m).

Production Example 8

According to the same process as that described in Production Example 1, N-{1-(hydroxymethyl)cyclohexyl}methyl-3-methoxy-4-(2-propynyloxy)benzamide (hereinafter referred to as the present compound 8) was obtained except for using 1-{1-(hydroxymethyl)cyclohexyl}methylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 8

[Chemical Formula 23]

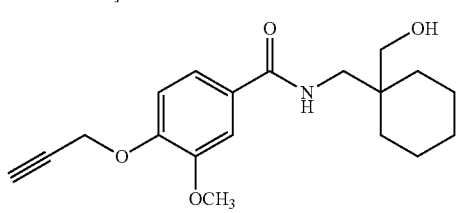

$^1$H-NMR (CDCl$_3$) δ: 1.28-1.52 (10H, m), 2.53 (1H, J=2.4 Hz), 3.38 (2H, d, J=7.0 Hz), 3.40 (2H, d, J=6.8 Hz), 3.85 (1H, t, J=7.0 Hz), 3.93 (3H, s), 4.82 (2H, d, J=2.4 Hz), 6.57-6.63 (1H, m), 7.03 (1H, d, J=8.3 Hz), 7.26 (1H, dd, J=8.3, 2.1 Hz), 7.46 (1H, d, J=2.1 Hz).

Production Example 9

According to the same process as that described in Production Example 1, N-{1-(hydroxymethyl)cyclopentyl}methyl-3,5-difluoro-4-(2-propynyloxy)benzamide (hereinafter, referred to as the present compound 9) was obtained except for using 1-{1-(hydroxymethyl)cyclopentyl}methylamine in place of 2-hydroxy-1,2-dimethylpropylamine.

The Present Compound 9

[Chemical Formula 24]

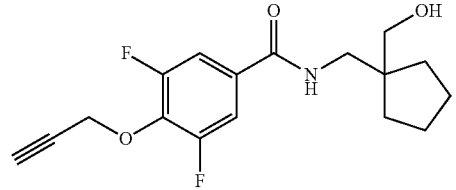

¹H-NMR (CDCl₃) δ: 1.37-1.53 (4H, m), 1.60-1.71 (4H, m), 2.52 (1H, t, J=2.4 Hz), 3.41-3.44 (4H, m), 3.46-3.50 (1H, m), 4.88 (2H, d, J=2.4 Hz), 7.02-7.08 (1H, m), 7.34-7.41 (2H, m).

Production Example 10

According to the same process as that described in Production Example 1, N-{1-(hydroxymethyl)cyclopentyl}methyl-3-methoxy-4-(2-propynyloxy)benozamide (hereinafter referred to as the present compound 10) was obtained except for using 1-{1-(hydroxymethyl)cyclopentyl)}methylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.
The Present Compound 10

[Chemical Formula 25]

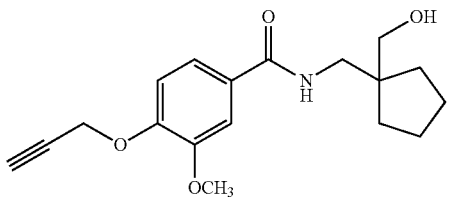

¹H-NMR (CDCl₃) δ: 1.34-1.55 (4H, m), 1.60-1.69 (4H, m), 2.53 (1H, t, J=2.4 Hz), 3.34 (2H, d, J=6.8 Hz), 3.42 (2H, d, J=6.5 Hz), 3.93 (3H, s), 3.97 (1H, t, J=6.8 Hz), 4.82 (2H, d, J=2.4 Hz), 6.69-6.74 (1H, m), 7.03 (1H, d, J=8.5 Hz), 7.26 (1H, dd, J=8.5, 2.2 Hz), 7.46 (1H, d, J=2.2 Hz).

Production Example 11

According to the same process as that describe in Production Example 1, N-{1-(hydroxymethyl)cyclobutyl}methyl-3,5-difluoro-4-(2-propynyloxy)benzamide (hereinafter referred to as the present compound 11) was obtained except for using 1-{1-(hydroxymethyl)cyclobutyl}methylamine in place of 2-hydroxy-1,2-dimethylpropylamine.
The Present Compound 11

[Chemical Formula 26]

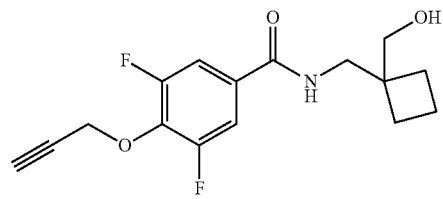

¹H-NMR (CDCl₃) δ: 1.78-1.87 (4H, m), 1.92-2.02 (2H, m), 2.52 (1H, t, J=2.4 Hz), 3.18 (1H, t, J=6.0 Hz), 3.59 (2H, d, J=6.0 Hz), 3.62 (2H, d, J=6.0 Hz), 4.88 (2H, d, J=2.4 Hz), 6.87-6.93 (1H, m), 7.32-7.39 (2H, m).

Production Example 12

According to the same process as that described in Production Example 1, N-{1-(hydroxymethyl)cyclobutyl}methyl-3-methoxy-4-(2-propynyloxy)benzamide (hereinafter referred to as the present compound 12) was obtained except for using 1-{1-(hydroxymethyl)cyclobutyl}methylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.
The Present Compound 12

[Chemical Formula 27]

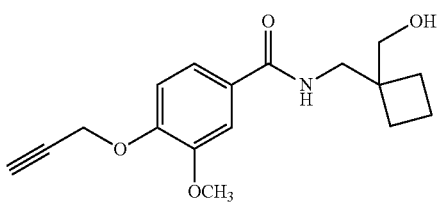

¹H-NMR (CDCl₃) δ: 1.77-1.85 (4H, m), 1.92-2.01 (2H, m), 2.53 (1H, t, J=2.4 Hz), 3.55 (2H, d, J=6.5 Hz), 3.59 (2H, d, J=6.3 Hz), 3.79 (1H, t, J=6.5 Hz), 3.92 (3H, s), 4.81 (2H, d, J=2.4 Hz), 6.76-6.82 (1H, m), 7.02 (1H, d, J=8.4 Hz), 7.26 (1H, dd, J=8.4, 2.2 Hz), 7.45 (1H, d, J=2.2 Hz).

Production Example 13

According to the same process as that described in Production Example 1, N-{1-(hydroxymethyl)cyclopropyl}methyl-3,5-difluoro-4-(2-propynyloxy)benzamide (hereinafter referred to as the present compound 13) was obtained except for using 1-{1-(hydroxymethyl)cyclopropyl}methylamine in place of 2-hydroxy-1,2-dimethylpropylamine.
The Present Compound 13

[Chemical Formula 28]

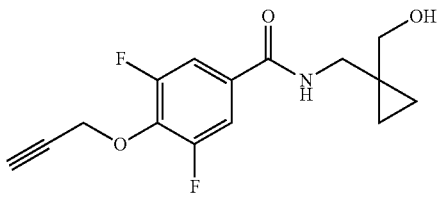

¹H-NMR (CDCl₃) δ: 0.50-0.57 (4H, m), 2.53 (1H, t, J=2.4 Hz), 3.26 (1H, br s), 3.43 (2H, d, J=5.6 Hz), 3.49 (2H, s), 4.88 (2H, d, J=2.4 Hz), 7.23-7.29 (1H, m), 7.36-7.43 (2H, m).

Production Example 14

According to the same process as that described in Production Example 1, N-{1-(hydroxymethyl)cyclopropyl}methyl-3-methoxy-4-(2-propynyloxy)benzamide (hereinafter referred to as the present compound 14) was obtained except for using 1-{1-(hydroxymethyl)cyclopropyl}methylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 14

[Chemical Formula 29]

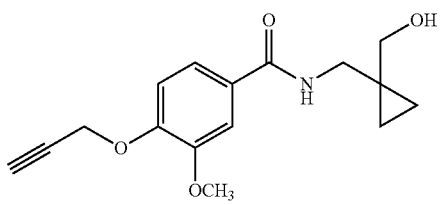

¹H-NMR (CDCl₃) δ: 0.49-0.56 (4H, m), 2.53 (1H, t, J=2.3 Hz), 3.37 (1H, t, J=6.0 Hz), 3.44 (2H, d, J=5.9 Hz), 3.44 (2H, d, J=5.8 Hz), 3.93 (3H, s), 4.82 (2H, d, J=2.2 Hz), 6.78-6.84 (1H, m), 7.04 (1H, d, J=8.4 Hz), 7.30 (1H, dd, J=8.4, 2.0 Hz), 7.47 (1H, d, J=2.0 Hz).

Production Example 15

According to the same process as that described in Production Example 1, N-(3-cyclohexenyl)methyl-3-methoxy-4-(2-propynyloxy)benzamide (hereinafter referred to as the present compound 15) was obtained except for using 3-cyclohexenylmethylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 15

[Chemical Formula 30]

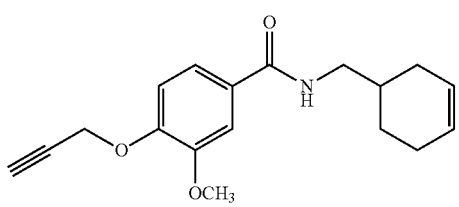

¹H-NMR (CDCl₃) δ: 1.28-1.40 (1H, m), 1.74-2.21 (6H, m), 2.53 (1H, t, J=2.4 Hz), 3.33-3.45 (2H, m), 3.92 (3H, s), 4.81 (2H, d, J=2.4 Hz), 5.63-5.72 (2H, m), 6.25-6.31 (1H, m), 7.02 (1H, d, J=8.2 Hz), 7.26 (1H, dd, J=8.2, 1.8 Hz), 7.46 (1H, d, J=1.8 Hz).

Production Example 16

According to the same process as that described in Production Example 1, N-{1-(dimethylamino)cyclohexyl}methyl-3,5-dimethoxy-4-(2-propynyloxy)benzamide (hereinafter referred to as the present compound 16) was obtained except for using 1-{1-(dimethylamino)cyclohexyl}methylamine in place of 2-hydroxy-1,2-dimethylpropylamine, and using 3,5-dimethoxy-4-(2-propynyloxy)benzoyl chloride in place of 3,5-difluoro-4-(2-propynyloxy)benzoyl chloride.

The Present Compound 16

[Chemical Formula 31]

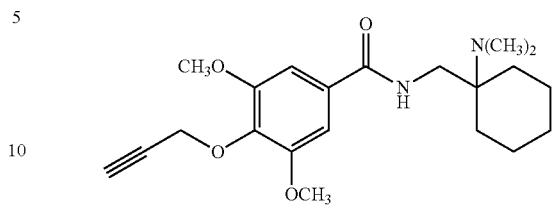

¹H-NMR (CDCl₃) δ: 1.09-1.89 (10H, m), 2.29 (6H, s), 2.44 (1H, t, J=2.4 Hz), 3.54 (2H, d, J=4.8 Hz), 3.91 (6H, s), 4.77 (2H, d, J=2.4 Hz), 6.91 (1H, br s), 7.01 (2H, s).

Production Example 17

According to the same process as that described in Production Example 1, N-{1-(dimethylamino)cyclohexyl}methyl-3,5-difluoro-4-(2-propynyloxy)benzamide (hereinafter referred to as the present compound 17) was obtained except for using 1-{1-(dimethylamino)cyclohexyl}methylamine in place of 2-hydroxy-1,2-dimethylpropylamine.

The Present Compound 17

[Chemical Formula 32]

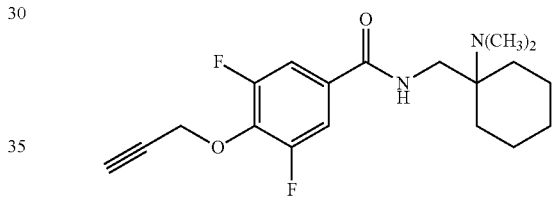

¹H-NMR (CDCl₃) δ: 1.07-1.69 (10H, m), 2.28 (6H, s), 2.53 (1H, t, J=1.8 Hz), 3.52 (2H, d, J=4.3 Hz), 4.88 (2H, d, J=2.2 Hz), 6.98 (1H, br s), 7.32-7.41 (2H, m).

Production Example 18

According to the same process as that described in Production Example 1, N-(1-cyclohexenyl)methyl-3,5-difluoro-4-(2-propynyloxy)benzamide (hereinafter referred to as the present compound 18) was obtained except for using 1-cyclohexenylmethylamine hydrochloride in place of 2-hydroxy-1,2-dimethylpropylamine.

The Present Compound 18

[Chemical Formula 33]

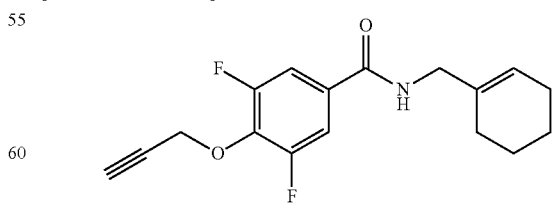

¹H-NMR (CDCl₃) δ: 1.55-1.68 (4H, m), 1.96-2.05 (4H, m), 2.52 (1H, t, J=2.4 Hz), 3.93 (2H, d, J=5.3 Hz), 4.88 (2H, d, J=2.4 Hz), 5.62-5.65 (1H, m), 6.07-6.10 (1H, m), 7.34-7.40 (2H, m).

Production Example 19

(Step 1)

According to the same process as that described in Production Example 1, N-(1-hydroxycyclohexyl)methyl-3,5-difluoro-4-(2-propynyloxy)benzamide was obtained except for using 1-(1-hydroxycyclohexyl)methylamine hydrochloride in place of 2-hydroxy-1,2-dimethylpropylamine.

N-(1-Hydroxycyclohexyl)methyl-3,5-difluoro-4-(2-propynyloxy)benzamide

[Chemical Formula 34]

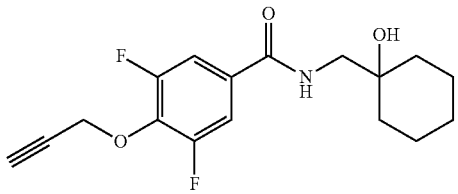

$^1$H-NMR (CDCl$_3$) δ: 1.35-1.58 (10H, m), 2.50-2.53 (2H, m), 3.47 (2H, d, J=5.9 Hz), 4.87 (2H, d, J=2.4 Hz), 6.75-6.76 (1H, br m), 7.37-7.43 (2H, m).

(Step 2)

To a mixture of 0.32 g of N-(1-hydroxycyclohexyl)methyl-3,5-difluoro-4-(2-propynyloxy)benzamide and 10 ml of chloroform were added successively 0.24 g of 4-dimethylaminopyridine and 0.14 ml of acetic anhydride, and the mixture was stirred at room temperature for 2 hours. Thereafter, the reaction mixture was added to an aqueous saturated sodium bicarbonate solution, followed by extraction with ethyl acetate. The organic layer was washed successively with an aqueous saturated citric acid solution and an aqueous saturated sodium bicarbonate solution, dried over magnesium sulfate, and concentrated under reduced pressure, and 0.20 g of N-(1-acetoxycyclohexyl)methyl-3,5-difluoro-4-(2-propynyloxy)benzamide (hereinafter referred to as the present compound 19) was obtained.

The Present Compound 19

[Chemical Formula 35]

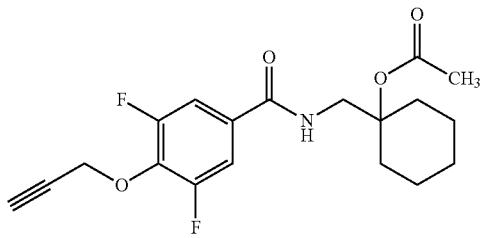

$^1$H-NMR (CDCl$_3$) δ: 1.29-1.61 (8H, m), 2.07-2.11 (2H, m), 2.12 (3H, s), 2.54 (1H, t, J=2.4 Hz), 3.76 (2H, d, J=5.8 Hz), 4.87 (2H, d, J=2.4 Hz), 7.39-7.46 (2H, m), 7.80-7.83 (1H, m).

Production Example 20

According to the same process as that described in Production Examples 1, N-(2-cyclohexenyl)-3,5-difluoro-4-(2-propynyloxy)benzamide (hereinafter referred to as the present compound 20) was obtained except for using 2-cyclohexenylamine in place of 2-hydroxy-1,2-dimethylpropylamine.

The Present Compound 20

[Chemical Formula 36]

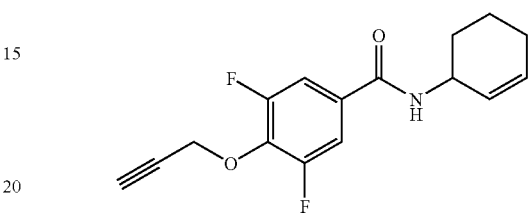

$^1$H-NMR (CDCl$_3$) δ: 1.60-1.73 (3H, m), 1.96-2.09 (3H, m), 2.51 (1H, t, J=2.4 Hz), 4.63-4.68 (1H, m), 4.88 (2H, d, J=2.4 Hz), 5.64-5.68 (1H, m), 5.92-5.95 (2H, m), 7.32-7.39 (2H, m).

Production Example 21

According to the same process as that described in Production Example 1, N-(2-methoxycyclohexyl)-3,5-difluoro-4-(2-propynyloxy)benzamide (hereinafter referred to as the present compound 21) was obtained except for using 2-methoxycyclohexylamine in place of 2-hydroxy-1,-dimethylpropylamine.

The Present Compound 21

[Chemical Formula 37]

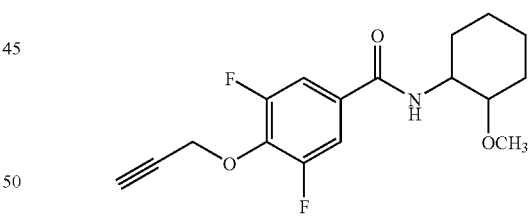

$^1$H-NMR (CDCl$_3$) δ: 1.15-2.09 (8H, m), 2.52 (1H, t, J=2.3 Hz), 3.35-3.36 (3H, m), 3.46-3.50 (1H, m), 4.05-4.13 (1H, m), 4.87 (2H, d, J=2.3 Hz), 6.50 (1H, d, J=8.0 Hz), 7.32-7.39 (2H, m).

Production Example 22

According to the same process as that described in Production Example 19, N-(2-acetoxycyclohexyl)-3,5-difluoro-4-(2-propynyloxy)benzamide (hereinafter referred to as the present compound 22) was obtained except for using 2-hydroxycyclohexylamine in place of 1-(1-hydroxycyclohexyl)methylamine hydrochloride.

The Present Compound 22

[Chemical Formula 38]

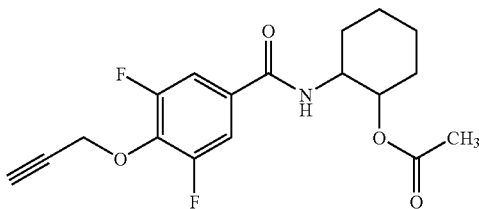

¹H-NMR (CDCl₃) δ: 1.23-2.03 (8.0H, m), 2.03 (0.6H, s), 2.13 (2.4H, s), 2.53 (1.0H, t, J=2.4 Hz), 3.94-4.03 (0.2H, m), 4.15-4.21 (0.8H, m), 4.76-4.84 (0.2H, m), 4.86-4.88 (2.0H, m), 5.10-5.13 (0.8H, m), 6.41 (0.8H, d, J=7.7 Hz), 6.57 (0.2H, d, J=8.5 Hz), 7.29-7.35 (2.0H, m).

Production Example 23

(Step 1)

To a mixture of 10 ml of ethyl acetate and 2.3 g of 3,5-difluoro-4-(2-propynyloxy)benzoyl chloride was added dropwise a mixture of 1.45 g of 7-azabicyclo[4.1.0]heptane, 2 ml of triethylamine and 3 ml of ethyl acetate with ice-cooling, and the mixture was stirred at room temperature for 4 hours. Thereafter, the reaction mixture was concentrated under reduced pressure, and, the resulting residue was subjected to silica gel column chromatography, and 1.8 g of Compound (A) shown by the following formula was obtained.

Compound (A)

[Chemical Formula 39]

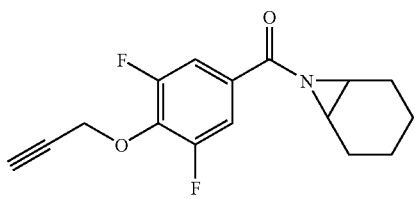

¹H-NMR (CDCl₃) δ: 1.33-1.41 (2H, m), 1.51-1.60 (2H, m), 1.89-1.96 (2H, m), 2.02-2.09 (2H, m), 2.53 (1H, t, J=2.4 Hz), 2.78 (2H, t, J=1.7 Hz), 4.90 (2H, d, J=2.4 Hz), 7.52-7.59 (2H, m).

(Step 2)

To a mixture of 3 ml of acetonitrile and 0.29 g of Compound (A) was added 77 mg of thiomethoxy sodium, and the mixture was stirred at room temperature for 3 hours. Thereafter, to the reaction mixture was added an aqueous sodium hydroxide solution, followed by extraction with ethyl acetate. The organic layer was dried over magnesium sulfate, and concentrated under reduced pressure, and the resulting crystals were washed with a mixed solvent of hexane and ethyl acetate, and 0.2 g of N-(2-methylthiocyclohexyl)-3,5-difluoro-4-(2-propynyloxy)benzamide (hereinafter referred to as the present compound 23) was obtained.

The Present Compound 23

[Chemical Formula 40]

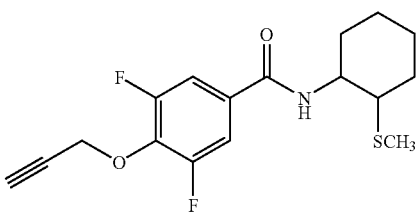

¹H-NMR (CDCl₃) δ: 1.25-1.84 (6H, m), 2.05 (3H, s), 2.13-2.17 (1H, m), 2.36-2.40 (1H, m), 2.48-2.54 (2H, m), 3.79-3.87 (1H, m), 4.88 (2H, d, J=2.4 Hz), 6.17 (1H, d, J=5.6 Hz), 7.34-7.41 (2H, m).

Production Example 24

According to the same process as that described in Production Example 1, N-{2-(1,1-dimethylethoxycarbonylamino)cyclohexyl}-3,5-difluoro-4-(2-propynyloxy)benzamide (hereinafter referred to as the present compound 24) was obtained except for using 2-(1,1-dimethylethoxycarbonylamino)cyclohexylamine in place of 2-hydroxy-1,2-dimethylpropylamine.

The Present Compound 24

[Chemical Formula 41]

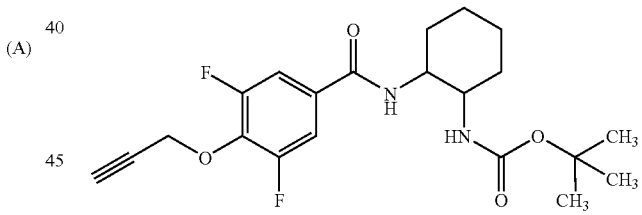

¹H-NMR (CDCl₃) δ: 1.17-2.31 (17.0H, m), 2.49 (0.4H, t, J=2.4 Hz), 2.51 (0.6H, t, J=2.4 Hz), 3.47-4.01 (2.0H, m), 4.63 (0.4H, d, J=8.3 Hz), 4.86-4.91 (2.6H, m), 7.28-7.31 (0.4H, m), 7.43-7.47 (2.0H, m), 7.83 (0.6H, d, J=4.4 Hz).

Production Example 25

To 1.0 g of N-{2-(1,1-dimethylethoxycarbonylamino)cyclohexyl}-3,5-difluoro-4-(2-propynyloxy)benzamide was added 5 ml of concentrated hydrochloric acid, and the mixture was stirred at room temperature for 12 hours. The reaction mixture was concentrated under reduced pressure, and the resulting residue was washed successively with a 15% aqueous sodium hydroxide solution, and MTBE, and 0.3 g of N-(2-aminocyclohexyl)-3,5-difluoro-4-(2-propynyloxy)benzamide (hereinafter referred to as the present compound 25) was obtained.

The Present Compound 25

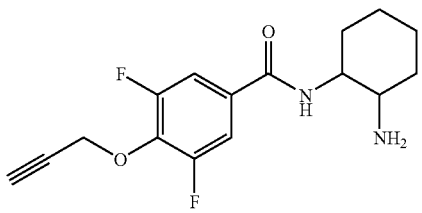

[Chemical Formula 42]

$^1$H-NMR (DMSO-d$_6$) δ: 1.24-2.02 (8.0H, m), 2.90-3.71 (2.3H, m), 4.04-4.09 (0.7H, m), 4.93-4.96 (2.0H, m), 5.40-5.86 (2.0H, m), 7.72-7.77 (2.0H, m), 8.15 (0.7H, d, J=6.3 Hz), 8.55 (0.3H, d, J=7.5 Hz).

Production Example 26

To a mixture of 5 ml of ethyl acetate, 0.34 g of N-(2-aminocyclohexyl)-3,5-difluoro-4-(2-propynyloxy)benzamide and 0.4 ml of triethylamine was added dropwise 0.07 g of acetyl chloride with ice-cooling. The resulting mixture was stirred at room temperature for 4 hours. Thereafter, the reaction mixture was concentrated under reduced pressured. The residue was subjected to silica gel column chromatography, and 0.21 g of N-(2-acetylaminocyclohexyl)-3,5-difluoro-4-(2-propynyloxy)benzamide (hereinafter referred to as the present compound 26) was obtained.

The Present Compound 26

[Chemical Formula 43]

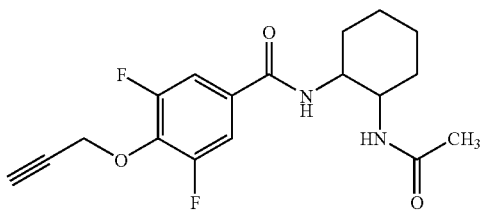

$^1$H-NMR (CDCl$_3$) δ: 1.16-2.08 (8.9H, m), 2.11 (2.1H, s), 2.51 (1.0H, t, J=2.1 Hz), 3.69-4.22 (2.0H, m), 4.87 (2.0H, d, J=2.2 Hz), 5.80 (0.3H, d, J=7.7 Hz), 5.95 (0.7H, d, J=4.8 Hz), 7.16-7.18 (0.3H, m), 7.39-7.47 (2.0H, m), 8.03-8.04 (0.7H, m).

Production Example 27

According to the same process as that described in Production Example 1, N-(2-dimethylaminocyclohexyl)-3,5-difluoro-4-(2-propynyloxy)benzamide (hereinafter referred to as the present compound 27) was obtained except for using 2-dimethylaminocyclohexylamine in place of 2-hydroxy-1,2-dimethylpropylamine.

The Present Compound 27

[Chemical Formula 44]

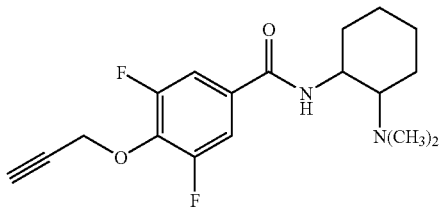

$^1$H-NMR (CDCl$_3$) δ: 1.08-1.43 (4H, m), 1.70-1.79 (1H, m), 1.81-1.94 (2H, m), 2.24 (6H, s), 2.40-2.46 (1H, m), 2.52 (1H, t, J=2.3 Hz), 2.62-2.67 (1H, m), 3.53-3.60 (1H, m), 4.86 (2H, d, J=2.4 Hz), 7.01-7.03 (1H, m), 7.34-7.40 (2H, m).

Production Example 28

According to the same process as that described in Production Example 1, N-(2-phenylcyclohexyl)-3,5-difluoro-4-(2-propynyloxy)benzamide (hereinafter referred to as the present compound 28) was obtained except for using 2-phenylcyclohexylamine in place of 2-hydroxy-1,2-dimethylpropylamine.

The Present Compound 28

[Chemical Formula 45]

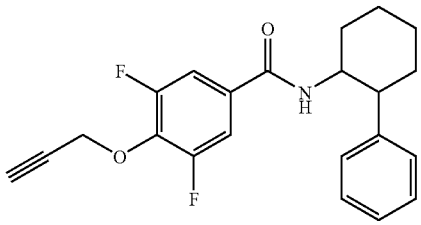

$^1$H-NMR (CDCl$_3$) δ: 1.30-2.33 (8.0H, m), 2.48 (0.2H, t, J=2.4 Hz), 2.50 (0.8H, t, J=2.4 Hz), 2.52-2.56 (0.2H, m), 3.07 (0.8H, dt, J=12.0, 3.7 Hz), 4.15-4.21 (0.2H, m), 4.48-4.53 (0.8H, m), 4.80 (0.4H, d, J=2.4 Hz), 4.83 (1.6H, d, J=2.4 Hz), 5.67 (0.2H, d, J=8.0 Hz), 5.91 (0.8H, d, J=7.6 Hz), 6.95-7.01 (0.4H, m), 7.04-7.10 (1.6H, m), 7.17-7.33 (5.0H, m).

Production Example 29

According to the same process as that described in Production Example 1, N-(2-benzylcyclohexyl)-3,5-difluoro-4-(2-propynyloxy)benzamide (hereinafter referred to as the present compound 29) was obtained except for using 2-benzylcyclohexylamine in place of 2-hydroxy-1,2-dimethylopropylamine.

The Present Compound 29

[Chemical Formula 46]

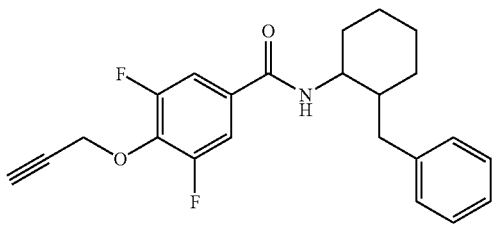

$^1$H-NMR (CDCl$_3$) δ: 1.09-2.16 (9.0H, m), 2.45-2.53 (2.0H, m), 2.77-2.88 (1.0H, m), 3.81-3.90 (0.4H, m), 4.28-4.33 (0.6H, m), 4.85-4.88 (2.0H, m), 5.89 (0.4H, d, J=8.8 Hz), 6.09 (0.6H, d, J=8.5 Hz), 7.10-7.36 (7.0H, m).

Production Example 30

According to the same process as that described in Production Example 1, N-(1-benzylcyclohexyl)-3-methoxy-4-(2-propynyloxy)benzamide (hereinafter referred to as the present compound 30) was obtained except for using 1-benzylcyclohexylamine in place of 2-hydroxy-1,2-dimethylpropylamine, and using 3-methoxy-4-(2-propynyloxy)benzoyl chloride in place of 3,5-difluloro-4-(2-propenyloxy)benzoyl chloride.

The Present Compound 30

[Chemical Formula 47]

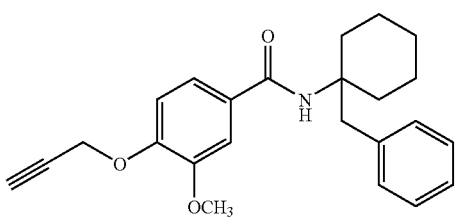

$^1$H-NMR (CDCl$_3$) δ: 1.24-1.65 (8H, m), 2.19-2.25 (2H, m), 2.52 (1H, t, J=2.4 Hz), 3.18 (2H, s), 3.93 (3H, s), 4.80 (2H, d, J=2.4 Hz), 5.40 (1H, s), 6.98 (1H, d, J=8.2 Hz), 7.06-7.25 (6H, m), 7.42 (1H, d, J=2.2 Hz).

Production Example 31

According to the same process as that described in Production Example 1, N-(trans-2-trifluoromethylcyclohexyl)-3,5-difluoro-4-(2-propynyloxy)benzamide (hereinafter referred to as the present compound 31) was obtained except for using 2-trifluoromethylcyclohexylamine in place of 2-hydroxy 1,2-dimethylpropylamine.

The Present Compound 31

[Chemical Formula 48]

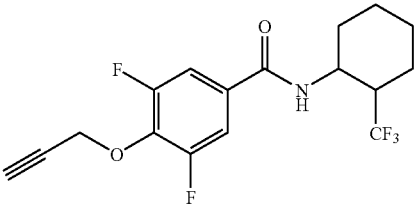

$^1$H-NMR (CDCl$_3$) δ: 1.30-2.07 (8H, m), 2.43-2.54 (2H, m), 4.62-4.69 (1H, m), 4.88 (2H, d, J=2.4 Hz), 6.20 (1H, d, J=8.0 Hz), 7.29-7.35 (2H, m).

Production Example 32

According to the same process as that described in Production Example 1, N-(cis-2-trifluoromethylcyclohexyl)-3,5-difluoro-4-(2-propynyloxy)benzamide (hereinafter referred to as the present compound 32) was obtained except for using 2-trifluoromethylcyclohexylamine in place of 2-hydroxy-1,2-dimethylpropylamine.

The Present Compound 32

[Chemical Formula 49]

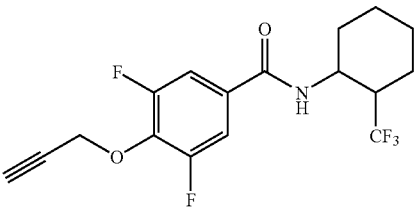

$^1$H-NMR (CDCl$_3$) δ: 1.29-2.10 (8H, m), 2.43-2.52 (1H, m), 2.55 (1H, t, J=2.4 Hz), 4.63-4.67 (1H, m), 4.86 (2H, d, J=2.2 Hz), 6.67 (1H, d, J=8.5 Hz), 7.30-7.37 (2H, m).

Production Example 33

According to the same process as that described in Production Example 1, N-{(2-hydroxymethyl)cyclohexyl}-3,5-difluoro-4-(2-propynyloxy)benzamide (hereinafter referred to as the present compound 33) was obtained except for using 2-(hydroxymethyl)cyclohexylamine in place of 2-hydroxy-1,2-dimethylpropylamine.

The Present Compound 33

[Chemical Formula 50]

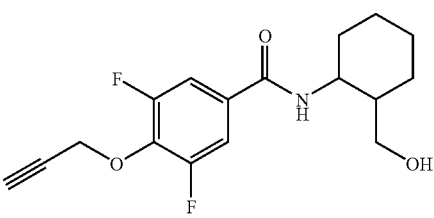

$^1$H-NMR (CDCl$_3$) δ: 1.09-2.07 (9.0H, m), 2.53-2.55 (1.0H, m), 3.34-3.50 (1.8H, m), 3.61-3.67 (0.2H, m), 3.75-3.88 (0.4H, m), 4.14-4.17 (0.8H, m), 4.39-4.43 (0.8H, m), 4.87-4.88 (2.0H, m), 6.72 (0.2H, d, J=8.2 Hz), 6.84 (0.8H, d, J=4.1 Hz), 7.33-7.44 (2.0H, m).

Production Example 34

To a mixture of 10 ml of a 15% aqueous sodium hydroxide solution and 20 ml of toluene were added 1.08 g of trans-2-hydroxycyclohexylamine hydrochloride, 0.05 g of tetrabutylammonium bromide and 0.80 g of 3-methoxy-4-(2-propynyloxy)benzoyl chloride, and the mixture was stirred at room temperature for 2 hours. After the reaction mixture was extracted with ethyl acetate, the organic layer was washed successively with water and an aqueous saturated sodium chloride solution, dried over magnesium sulfate, and concentrated under reduced pressure. The residue was subjected to silica gel column chromatography, and 1.1 g of N-(trans-2-hydroxycyclohexyl)-3-methoxy-4-(2-propynyloxy)benzamide was obtained.

N-(trans-2-Hydroxycyclohexyl)-3-methoxy-4-(2-propynyloxy)benzamide

[Chemical Formula 51]

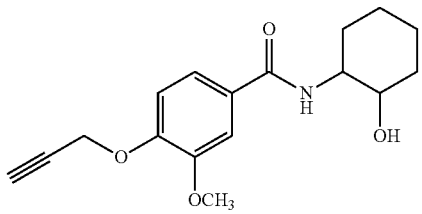

$^1$H-NMR (CDCl$_3$) δ: 1.22-1.45 (4H, m), 1.70-1.81 (2H, m), 2.01-2.15 (2H, m), 2.53 (1H, t, J=2.4 Hz), 3.43 (1H, td, J=10.0, 4.3 Hz), 3.51-3.69 (1H, m), 3.77-3.88 (1H, m), 3.91-3.95 (3H, m), 4.81 (2H, d, J=2.4 Hz), 6.10 (1H, d, J=6.5 Hz), 7.03 (1H, d, J=8.5 Hz), 7.27 (1H, dd, J=8.2, 2.2 Hz), 7.44 (1H, d, J=1.9 Hz).

To 20 ml of chloroform were added 1.0 g of N-(trans-2-hydroxycyclohexyl)-3-methoxy-4-(2-propynyloxy)benzamide obtained by the above operation, 1.3 g of bis (acetoxy) phenyl iodide and 0.10 g of 2,2,6,6-tetramethylpiperidine N-oxide, and the mixture was stirred at room temperature for 8 hours. The reaction mixture was concentrated under reduced pressure, and added to water, followed by extraction with ethyl acetate. The organic, layer was washed with an aqueous saturated sodium bicarbonate solution, dried with magnesium sulfate, and concentrated under reduced pressure. The residue was subjected to silica gel column chromatography, and 0.70 g of N-(2-oxocyclohexyl)-3-methoxy-4-(2-propynyloxy)benzamide (hereinafter referred to as the present compound 34) was obtained.

The Present Compound 34

[Chemical Formula 52]

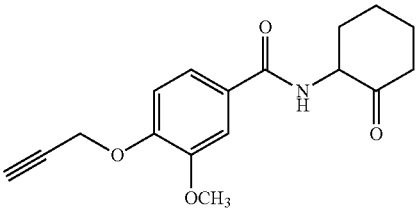

$^1$H-NMR (CDCl$_3$) δ: 1.39-1.51 (1H, m), 1.63-1.97 (3H, m), 2.15-2.24 (1H, m), 2.42-2.52 (1H, m), 2.53 (1H, t, J=2.3 Hz), 2.56-2.63 (1H, m), 2.78-2.86 (1H, m), 3.94 (3H, s), 4.61-4.69 (1H, m), 4.82 (2H, d, J=2.4 Hz), 7.05 (1H, d, J=8.2 Hz), 7.14-7.15 (1H, br m), 7.36 (1H, dd, J=8.3, 2.1 Hz), 7.45 (1H, d, J=1.9 Hz).

Production Example 35

To 10 ml of ethanol were added 0.40 g of N-(2-oxocyclohexyl)-3-methoxy-4-(2-propynyloxy)benzamide, 0.40 g of hydroxylamine hydrochloride and 0.40 g of triethylamine, and this was heated under reflex for 2 hours. The reaction mixture which had been allowed to cool to near room temperature was concentrated under reduced pressure, water was added to the residue, and this was extracted with ethyl acetate. The organic layer was dried over magnesium sulfate, and concentrated under reduced pressure. The residue was subjected to silica gel column chromatography, and 83 mg of N-(2-hydroxyiminocyclohexyl)-3-methoxy-4-(2-propynyloxy)benzamide (hereinafter referred to as the present compound 35) was obtained.

The Present Compound 35

[Chemical Formula 53]

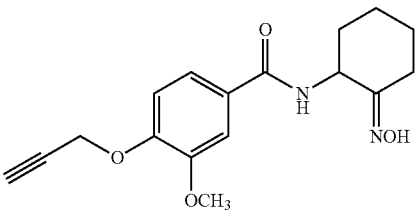

$^1$H-NMR (DMSO-d$_6$) δ: 1.30-1.51 (2H, m), 1.56-2.00 (4H, m), 2.46-2.63 (2H, m), 3.42-3.52 (1H, m), 3.92-3.97 (3H, m), 4.49-4.60 (1H, m), 4.79-4.86 (2H, m), 7.00-7.07 (1H, m), 7.31-7.51 (3H, m), 9.75-9.80 (1H, m).

Production Example 36

According to the same process as that described in Production Example 1, N-(2-oxocyclohexyl)-3,5-difluoro-4-(2-propynyloxy)benzamide (hereinafter referred to as the present compound 36) was obtained except for using 2-aminocyclohexanone in place of 2-hydroxy-1,2-dimethylpropylamine.

The Present Compound 36

[Chemical Formula 54]

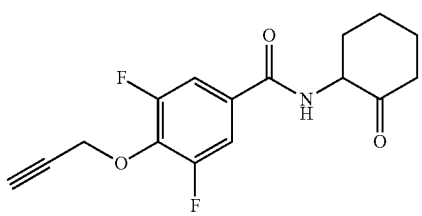

$^1$H-NMR (CDCl$_3$) δ: 1.44 (1H, ddd, J=25.0, 12.6, 4.2 Hz), 1.70 (1H, tdd, J=17.4, 8.9, 4.4 Hz), 1.81-1.96 (2H, m), 2.17-2.23 (1H, m), 2.46 (1H, td, J=13.6, 6.1 Hz), 2.52 (1H, t, J=2.3 Hz), 2.58-2.63 (1H, m), 2.76-2.83 (1H, m), 4.58-4.64 (1H, m), 4.89 (2H, d, J=2.2 Hz), 7.11 (1H, d, J=4.6 Hz), 7.35-7.44 (2H, m).

Production Example 37

To a mixture of 1 ml of tetrahydrofuran and 0.65 g of methyltriphenylphosphonium iodide was added 0.17 g of tert-butoxy potassium at room temperature, the mixture was stirred at room temperature for 30 minutes, a mixture of 0.25 g of N-(2-oxocyclohexyl)-3,5-difluoro-4-(2-propynyloxy)benzamide and 1 ml of tetrahydrofuran was added dropwise, and the mixture was stirred for 3 hours. Thereafter, an aqueous saturated ammonium chloride solution was added to the reaction mixture, followed by extraction with ethyl acetate. The organic layer was dried with magnesium sulfate, and concentrated under reduced pressure. The residue was subjected to silica gel chromatography, and 0.17 g of N-(2-methylenecyclohexyl)-3,5-difluoro-4-(2-propynyloxy)benzamide (hereinafter referred to as the present compound 37) was obtained.
The Present Compound 37

[Chemical Formula 55]

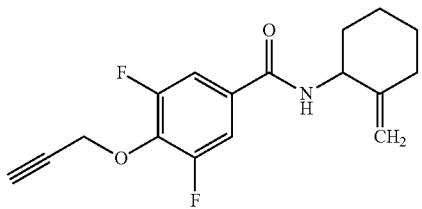

$^1$H-NMR (CDCl$_3$) δ: 1.26-1.43 (2H, m), 1.54-1.64 (1H, m), 1.76-1.86 (2H, m), 2.02-2.17 (2H, m), 2.41-2.47 (1H, m), 2.53 (1H, t, J=2.4 Hz), 4.52-4.59 (1H, m), 4.70 (1H, d, J=1.1 Hz), 4.78 (1H, d, J=1.1 Hz), 4.88 (2H, d, J=2.4 Hz), 6.19 (1H, d, J=8.5 Hz), 7.36-7.43 (2H, m).

Production Example 38

According to the same process as that described in Production Example 1, N-(1-cyano-1-cyclohexylmethyl)-3-methoxy-4-(2-propynyloxy)benzamide (hereinafter referred to as the present compound 38) was obtained except for using 1-cyano-1-cyclohexylmethylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 38

[Chemical Formula 56]

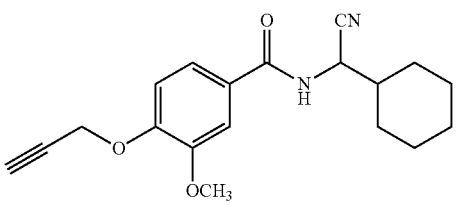

$^1$H-NMR (CDCl$_3$) δ: 1.15-1.31 (5H, m), 1.66-1.98 (6H, m), 2.54 (1H, t, J=2.3 Hz), 3.94 (3H, s), 4.83 (2H, d, J=2.3 Hz), 5.02 (1H, dd, J=8.9, 6.8 Hz), 6.46 (1H, d, J=8.9 Hz), 7.05 (1H, d, J=8.2 Hz), 7.29 (1H, dd, J=8.2, 2.0 Hz), 7.44 (1H, d, J=2.0 Hz).

Production Example 39

According to the same process as that described in Production Example 1, N-(1-cyano-1-cyclohexylmethyl)-3,5-difluoro-4-(2-propynyloxy)benzamide (hereinafter referred to as the present compound 39) was obtained except for using 1-cyano-1-cyclohexylmethylamine in place of 2-hydroxy-1,2-dimethylpropylamine.

The Present Compound 39

[Chemical Formula 57]

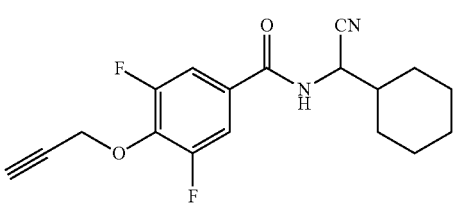

$^1$H-NMR (CDCl$_3$) δ: 1.15-1.32 (5H, m), 1.71-1.96 (6H, m), 2.53 (1H, t, J=2.4 Hz), 4.91 (2H, d, J=2.4 Hz), 4.97 (1H, dd, J=8.9, 6.8 Hz), 6.49 (1H, d, J=8.7 Hz), 7.36-7.43 (2H, m).

Production Example 40

According to the same process as that described in Production Example 1, N-(1-phenyl-1-cyclohexylmethyl)-3-methoxy-4-(propynyloxy)benzamide (hereinafter referred to as the present compound 40) was obtained except for using 1-phenyl-1-cyclohexylmethylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

Present Compound 40

[Chemical Formula 58]

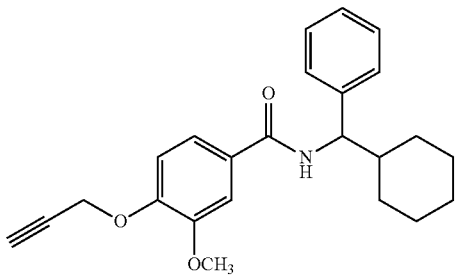

$^1$H-NMR (CDCl$_3$) δ: 0.96-1.28 (5H, m), 1.47-1.95 (6H, m), 2.52 (1H, t, J=2.4 Hz), 3.91 (3H, s), 4.80 (2H, d, J=2.4 Hz), 4.96 (1H, dd, J=8.5, 8.6 Hz), 6.34 (1H, d, J=8.5 Hz), 7.02 (1H, d, J=8.5 Hz), 7.23-7.36 (6H, m), 7.45 (1H, d, J=2.2 Hz).

Production Example 41

According to the same process as that described in Production Example 1, N-(1-phenyl-1-cyclohexylmethyl)-3,5-difluoro-4-(2-propynyloxy)benzamide (hereinafter, referred to as the present compound 41) was obtained except for using 1-phenyl-1-cyclohexylmethylamine in place of 2-hydroxy-1,2-dimethylpropylamine.

The Present Compound 41

[Chemical Formula 59]

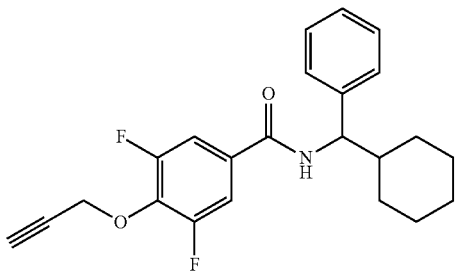

$^1$H-NMR (CDCl$_3$) δ: 0.87-1.28 (6H, m), 1.46-1.91 (5H, m), 2.50 (1H, t, J=2.4 Hz), 4.86 (2H, d, J=2.4 Hz), 4.91 (1H, dd, J=8.9, 8.7 Hz), 6.29 (1H, d, J=8.9 Hz), 7.24-7.37 (7H, m).

Production Example 42

According to the same process as that described in Production Example 1, N-(1-cyclohexyl-2,2,2-trifluoroethyl),3-5-difluoro-4-(2-propynyloxy)benzamide (hereinafter referred to as the present compound 42) was obtained except for using 1-cyclohexyl-2,2,2-trifluoroethylamine in place of 2-hydroxy-1,2-dimethylpropylamine.

The Present Compound 42

[Chemical Formula 60]

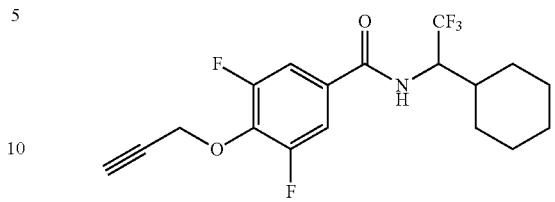

$^1$H-NMR (CDCl$_3$) δ: 1.03-1.37 (5H, m), 1.65-1.94 (6H, m), 2.53 (1H, t, J=2.4 Hz), 4.64-4.75 (1H, m), 4.90 (2H, d, J=2.4 Hz), 6.09 (1H, d, J=9.9 Hz), 7.35-7.41 (2H, m).

Production Example 43

According to the same process as that described in Production Example 1, N-(1-cyclohexyl-2,2,2-trifluoroethyl)-3-methoxy-4-(2-propynyloxy)benzamide (hereinafter referred to as the present compound 43) was obtained except for using 1-cyclohexyl-2,2,2-trifluoroethylamine in place of 2-hydroxy-1,2-dimethylpropylamine, and using 3-methoxy-4-(2-propynyloxy)benzoyl chloride in place of 3,5-difluoro-4-(2-propynyloxy)benzoyl chloride.

The Present Compound 43

[Chemical Formula 61]

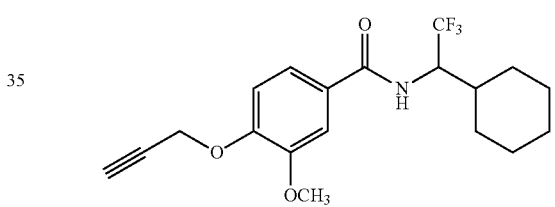

$^1$H-NMR (CDCl$_3$) δ: 1.04-1.39 (5H, m), 1.64-1.95 (6H, m), 2.54 (1H, t, J=2.4 Hz), 3.95 (3H, s), 4.70-4.81 (1H, m), 4.83 (2H, d, J=2.4 Hz), 6.11 (1H, d, J=10.1 Hz), 7.07 (1H, d, J=8.3 Hz), 7.27 (1H, dd, J=8.3, 2.0 Hz), 7.49 (1H, d, J=2.0 Hz).

Next, regarding the production of the intermediate for producing the present compound, Reference Production Examples will be shown.

Reference Production Example 1

To 100 ml of DMF were added 11.8 g of 4-hydroxy-3,5-dimethoxybenzoic acid, 15.7 g of propargyl bromide and 18 g of potassium carbonate, and the resulting mixture was stirred at room temperature for 8 hours and, then, at 80° C. for 4 hours. Thereafter, ethyl acetate was added to the reaction mixture which had been allowed to cool to near room temperature, and this was filtered through Celite (registered trade mark). To the filtrate were added successively water and dilute hydrochloric acid, followed by extraction with ethyl acetate. The organic layer was dried over magnesium sulfate, and concentrated under reduced pressure. The resulting crystals were washed with a mixed solvent of hexane and MTBE, and 15.5 g of 2-propynyl 4-(2-propynyloxy)-3,5-dimethoxybenzoate was obtained.

[Chemical Formula 62]

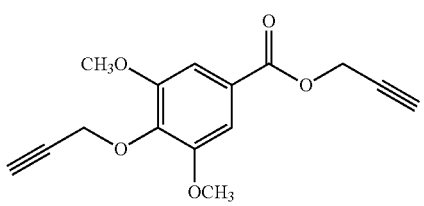

2-propynyl 4-(2-Propynyloxy)-3,5-dimethoxybenzoate $^1$H-NMR (CDCl$_3$) δ: 2.44 (1H, t, J=2.4 Hz), 2.52 (1H, t, J=2.4 Hz), 3.91 (6H, s), 4.81 (2H, d, J=2.4 Hz), 4.92 (2H, d, J=2.4 Hz), 7.33 (2H, s).

To 50 ml of methanol were added 15.5 g of 2-propynyl 4-(2-propynyloxy)-3,5-dimethoxybenzoate and 40 ml of a 15% aqueous sodium hydroxide solution, and the resulting mixture was stirred at 50° C. for 4 hours. Thereafter, the reaction mixture which had been allowed to cool to near room temperature was made acidic by addition of hydrochloric acid. The precipitated crystals were collected by filtration, and dried, and 13.0 g of 4-(2-propynyloxy)-3,5-dimethoxybenzoic acid was obtained.

4-(2-Propynyloxy)-3,5-dimethoxybenzoic acid

[Chemical Formula 63]

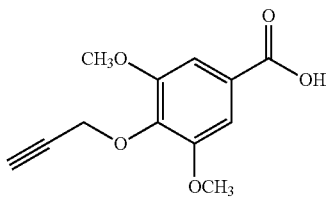

$^1$H-NMR (DMSO-d$_6$) δ: 3.35 (1H, br s), 3.45 (1H, t, J=2.4 Hz), 3.83 (6H, s), 4.70 (2H, d, J=2.4 Hz), 7.24 (2H, s).

To 100 ml of toluene were added 13.0 g of 4-(2-propynyloxy)-3,5-dimethoxybenzoic acid, 9.5 g of thionyl chloride and 50 mg of DMF, and the resulting mixture was heated under reflux for 3 hours. Thereafter, the reaction mixture which had been allowed to cool to near room temperature was concentrated under reduced pressure. The resulting solid was washed with hexane, and 12.0 g of 4-(2-propynyloxy)-3,5-dimethoxybenzoyl chloride was obtained.

4-(2-Propynyloxy)-3,5-dimethoxybenzoyl chloride

[Chemical Formula 64]

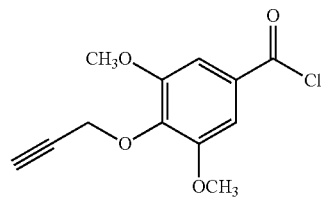

$^1$H-NMR (CDCl$_3$) δ: 2.46 (1H, t, J=2.4 Hz), 3.93 (6H, s), 4.87 (2H, d, J=2.4 Hz), 7.38 (2H, s).

Reference Production Example 2

To 100 ml of DMF were added 10 g of 4-hydroxy-3-methoxybenzoic acid, 15.7 g of propargyl bromide and 18 g of potassium carbonate, and the resulting mixture was stirred at room temperature for 8 hours, and then at 80° C. for 2 hours. Thereafter, ethyl acetate was added to the reaction mixture which had been allowed to cool to near room temperature, and this was filtered through Celite (registered trade mark). To the filtrate were added sequentially water and dilute hydrochloric acid, followed by extraction with ethyl acetate. The organic layer was dried with magnesium sulfate, and concentrated under reduced pressure. The resulting crystals were washed with a mixed solvent of hexane and MTBE, and 13.2 g of 2-propynyl 4-(2-propynyloxy)-3-methoxybenzoate was obtained.

2-Propynyl 4-(2-propynyloxy)-3-methoxybenzoate

[Chemical Formula 65]

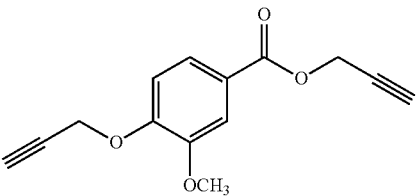

$^1$H-NMR (CDCl$_3$) δ: 2.52 (1H, t, J=2.5 Hz), 2.55 (1H, t, J=2.4 Hz), 3.93 (3H, s), 4.83 (2H, d, J=2.4 Hz), 4.91 (2H, d, J=2.4 Hz), 7.05 (1H, d, J=8.7 Hz), 7.58 (1H, d, J=1.9 Hz), 7.72 (1H, dd, J=8.5, 1.9 Hz).

To 50 ml of methanol were added 13.2 g of 2-propynyl 4-(2-propynyloxy)-3-methoxybenzoate and 40 ml of a 15% aqueous sodium hydroxide solution, and the resulting mixture was stirred at room temperature for 8 hours, and then at 50° C. for 2 hours. Thereafter, the reaction mixture which had been allowed to cool to near room temperature was added to hydrochloric acid to make the mixture acidic. The precipitated crystals were collected by filtration, and dried, and 12.0 g of 4-(2-propynyloxy)-3-methoxybenzoic acid was obtained.

4-(2-Propynyloxy)-3-methoxybenzoic acid

[Chemical Formula 66]

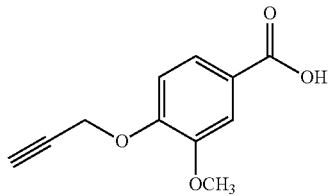

To 100 ml of toluene were added 12.0 g of 4-(2-propyny-loxy)-3-methoxybenzoic acid, 9.0 g of thionyl chloride and 50 mg of DMF, and the resulting mixture was heated to reflux for 3 hours. Thereafter, the reaction mixture which had been allowed to cool to near room temperature was concentrated under reduced pressure. The resulting solid was washed with hexane, and 11.0 g of 4-(2-propynyloxy)-3-methoxybenzoyl chloride was obtained.

4-(2-Propynyloxy)-3-methoxybenzoyl chloride

[Chemical Formula 67]

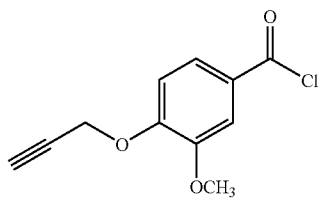

$^1$H-NMR (CDCl$_3$) δ: 2.59 (1H, t, J=2.4 Hz), 3.94 (3H, s), 4.87 (2H, d, J=2.4 Hz), 7.10 (1H, d, J=8.7 Hz), 7.56 (1H, d, J=2.2 Hz), 7.84 (1H, dd, J=8.7, 2.2 Hz).

Reference Production Example 3

To 50 ml of DMF were added 5.5 g of 4-hydroxy-3-fluorobenzoic acid, 9.4 g of propargyl bromide and 11 g of potassium carbonate, and the resulting mixture was stirred at room temperature for 8 hours. Thereafter, ethyl acetate was added to the reaction mixture, and this was filtered through Celite (registered trade mark). Water and dilute hydrochloric acid were successively added to the filtrate, followed by extraction with ethyl acetate. The organic layer was dried over magnesium sulfate, and concentrated under reduced pressure. The residue was subjected to silica gel column chromatography, and 10.8 g of 2-propynyl 4-(2-propynyloxy)-3-fluorobenzoate was obtained.

2-Propynyl 4-(2-propynyloxy)-3-fluorobenzoate

[Chemical Formula 68]

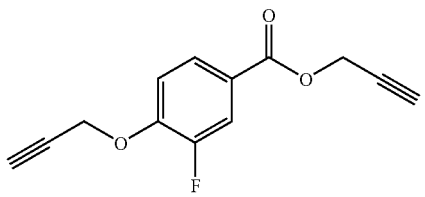

$^1$H-NMR (CDCl$_3$) δ: 2.50 (1H, t, J=2.5 Hz), 2.56 (1H, t, J=2.4 Hz), 4.82 (2H, d, J=2.4 Hz), 4.89 (2H, d, J=2.4 Hz), 7.13 (1H, t, J=8.3 Hz), 7.78 (1H, dd, J=11.5, 2.1 Hz), 7.82-7.86 (1H, m).

To 50 ml of ethanol were added 10.8 g of 2-propynyl 4-(2-propynyloxy)-3-fluorobenzoate and 30 ml of a 15% aqueous sodium hydroxide solution, and the resulting mixture was stirred at room temperature for 2 hours. Thereafter, the reaction mixture was added to hydrochloric acid to make the mixture acidic. The precipitated crystals were collected by filtration and dried, and 8.0 g of 4-(2-propynyloxy)-3-fluorobenzoic acid was obtained.

4-(2-Propynyloxy)-3-fluorobenzoic acid

[Chemical Formula 69]

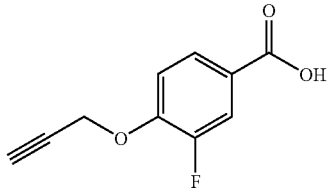

$^1$H-NMR (DMSO-d$_6$) δ: 3.21-3.59 (1H, m), 3.68 (1H, t, J=2.3 Hz), 5.01 (2H, d, J=2.2 Hz), 7.34 (1H, t, J=8.5 Hz), 7.71 (1H, dd, J=11.8, 1.9 Hz), 7.77-7.83 (1H, m).

Reference Production Example 4

(a) To 50 ml of N-methylpyrrolidone were added 10 g of 3,4,5-trifluorobromobenzene and 8.5 g of copper cyanide, and the resulting mixture was stirred at 150° C. for 4 hours. Thereafter, aqueous ammonia was added to the reaction mixture which had been allowed to cool to near room temperature, followed by extraction with ethyl acetate. The organic layer was dried over magnesium sulfate, and concentrated under reduced pressure. The residue was subjected to silica gel column chromatography, and 5.0 g of 3,4,5-trifluorobenzonitrile was obtained.

3,4,5-Trifluorobenzonitrile

[Chemical Formula 70]

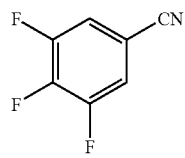

To a mixture obtained by adding 5.0 g of 3,4,5-trifluorobenzonitrile and 4.5 g of benzyl alcohol to 25 ml of DMF was added 1.5 g of 60% sodium hydride (oily) at 0° C. The mixture was stirred at room temperature for 4 hours. Thereafter, dilute hydrochloric acid was added to the reaction mixture, followed by extraction with ethyl acetate. The organic layer was dried over magnesium sulfate, and concentrated under reduced pressure. The residue was subjected to silica gel column chromatography, and 7.0 g of 4-benzyloxy-3,5-difluorobenzonitrile was obtained.

4-Benzyloxy-3,5-difluorobenzonitrile

[Chemical Formula 71]

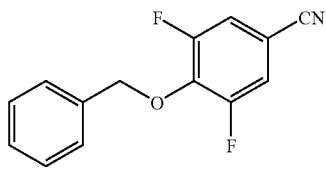

$^1$H-NMR (CDCl$_3$) δ: 5.29 (2H, s), 7.14-7.23 (2H, m), 7.29-7.43 (5H, m).

To 100 ml of methanol were added 7.0 g of 4-benzyloxy-3,5-difluorobenzonitrile and 15 ml of concentrated sulfuric acid, and the resulting mixture was heated under reflux for 5 days. Thereafter, water was added to the reaction mixture which had been allowed to cool to near room temperature, followed by extraction with ethyl acetate. The organic layer was dried over magnesium sulfate, and concentrated under reduced pressure. The residue was subjected to silica gel column chromatography, and 4.5 g of methyl 3,5-difluoro-4-hydroxybenzoate was obtained.

Methyl 3,5-difluoro-4-hydroxybenzoate

[Chemical Formula 72]

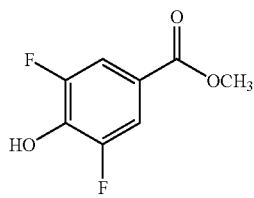

$^1$H-NMR (CDCl$_3$) δ: 3.91 (3H, s), 6.00 (1H, br s), 7.58-7.67 (2H, m).

To 80 ml of acetonitrile were added 4.5 g of methyl 3,5-difluoro-4-hydroxybenzoate, 3.5 g of propargyl bromide and 9.4 g of cesium carbonate, and the resulting mixture was heated to reflux for 2 hours. Thereafter, the reaction mixture which had been allowed to cool to near room temperature was filtered through Celite (registered trade mark). The filtrate was concentrated under reduced pressure, and the residue was subjected to silica gel column chromatography, and 5.5 g of methyl 3,5-difluoro-4-(2-propynyloxy)benzoate was obtained.

Methyl 3,5-difluoro-4-(2-propynyloxy)benzoate

[Chemical Formula 73]

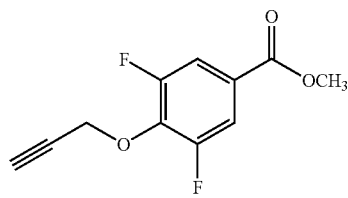

$^1$H-NMR (CDCl$_3$) δ: 2.53 (1H, t, J=2.4 Hz), 3.92 (3H, s), 4.91 (2H, d, J=2.4 Hz), 7.61 (2H, ddd, J=15.1, 7.5, 2.2 Hz).

To 30 ml of ethanol were added 5.5 g of methyl 3,5-difluoro-4-(2-propynyloxy)benzoate and 10 ml of a 15% aqueous sodium hydroxide solution, and the resulting mixture was stirred at room temperature for 2 hours. Thereafter, the reaction mixture was concentrated under reduced pressure. Hydrochloric acid was added to the residue to make the mixture acidic, and the precipitated solids were collected by filtration, and 5.0 g of 3,5-difluoro-4-(2-propynyloxy)benzoic acid was obtained.

3,5-Difluoro-4-(2-propynyloxy)benzoic acid

[Chemical Formula 74]

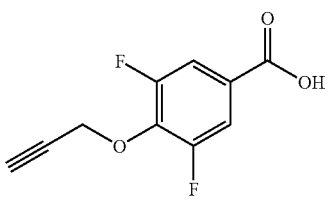

$^1$H-NMR (CDCl$_3$) δ: 2.54 (1H, t, J=2.2 Hz), 4.94 (2H, d, J=2.2 Hz), 7.65-7.72 (2H, m).

(b) To 50 ml of DMF were added 5.0 g of 3,4,5-trifluorobenzoic acid, 4.0 g of propargyl bromide and 4.7 g of potassium carbonate. The mixture was stirred at room temperature for 30 minutes, and then at 80° C. for 1 hour. Thereafter, ethyl acetate was added to the reaction mixture which had been allowed to cool to near room temperature, and this was filtered through Celite (registered trade mark). To the filtrate were added successively water and dilute hydrochloric acid, followed by extraction with ethyl acetate. The organic layer was dried over magnesium sulfate, and concentrated under reduced pressure, and 6.0 g of 2-propynyl 3,4,5-trifluorobenzoate was obtained.

2-Propynyl 3,4,5-trifluorobenzoate

[Chemical Formula 75]

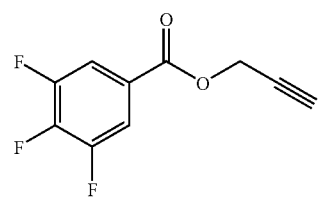

$^1$H-NMR (CDCl$_3$) δ: 2.55 (1H, t, J=2.4 Hz), 4.93 (2H, d, J=2.4 Hz), 7.68-7.76 (2H, m).

To a mixture obtained by adding 5.0 g of 2-propynyl 3,4,5-trifluorobenzoate and 1.7 g of propargyl alcohol to 20 ml of DMF was added 1.1 g of 60% sodium hydride (oily) at 0° C. The resulting mixture was stirred at 0° C. for 30 minutes, and then at room temperature for 1 hour. Thereafter, water was added to the reaction mixture, followed by extraction with ethyl acetate. The organic layer was dried over magnesium sulfate, and concentrated under reduced pressure. The residue was subjected to silica gel column chromatography, and 2.9 g of 2-propynyl 3,5-difluoro-4-(2-propynyloxy)benzoate was obtained.

2-Propynyl 3,5-difluoro-4-(2-propynyloxy)benzoate

[Chemical Formula 76]

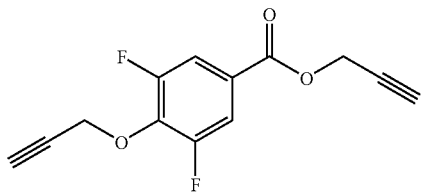

¹H-NMR (CDCl₃) δ: 2.52 (1H, t, J=2.4 Hz), 2.54 (1H, t, J=2.4 Hz), 4.91 (2H, d, J=2.7 Hz), 4.92 (2H, d, J=2.7 Hz), 7.62-7.68 (2H, m).

To 10 ml of ethanol were added 2.2 g of 2-propynyl 3,5-difluoro-4-(2-propynyloxy)benzoate and 6 ml of a 15% aqueous sodium hydroxide solution, and the resulting mixture was stirred at 50° C. for 1 hour. Thereafter, the reaction mixture which had been allowed to cool to near room temperature was concentrated under reduced pressure, and hydrochloric acid was added to the residue to make the mixture acidic. The precipitated crystals were collected by filtration, and dried, and 1.8 g of 3,5-difluoro-4-(2-propynyloxy)benzoic acid was obtained.

To 17 ml of toluene were added 1.8 g of 3,5-difluoro-4-(2-propynyloxy)benzoic acid, 1 ml of thionyl chloride and 10 mg of DMF, and the resulting mixture was heated to reflux for 4 hours. Thereafter, the reaction mixture which had been allowed to cool to near room temperature was concentrated under reduced pressure, and 1.9 g of 3,5-difluoro-4-(2-propynyloxy)benzoyl chloride was obtained.

3,5-Difluoro-4-(2-propynyloxy)benzoyl chloride

[Chemical Formula 77]

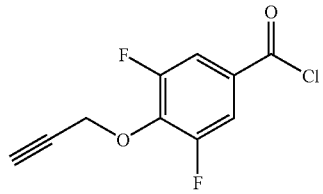

¹H-NMR (CDCl₃) δ: 2.55 (1H, t, J=2.4 Hz), 4.98 (2H, d, J=2.4 Hz), 7.69-7.76 (2H, m).

Reference Production Example 5

To 40 ml of acetonitrile were added 7.3 g of 3-fluoro-4-hydroxy-5-methoxybenzaldehyde, 8.8 g of benzyl bromide, 16.8 g of cesium carbonate and 10 ml of DMF, and the resulting mixture was heated under reflux for 10 hours. Thereafter, the reaction mixture which had been cool to near room temperature was concentrated under reduced pressure. Hydrochloric acid was added to the residue, followed by extraction with ethyl acetate. The organic layer was dried over magnesium sulfate, and concentrated under reduced pressure. The residue was subjected to silica gel column chromatography, and 7.5 g of 4-benzyloxy-3-fluoro-5-methoxybenzaldehyde was obtained.

4-Benzyloxy-3-fluoro-5-methoxybenzaldehyde

[Chemical Formula 78]

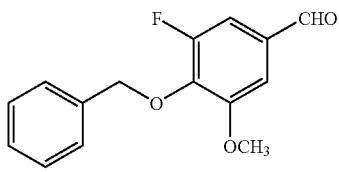

To a mixture of 200 ml of water and 6.8 g of potassium permanganate was added dropwise 7.5 g of 4-benzyloxy-3-fluoro-5-methoxybenzaldehyde dissolved in 200 ml of acetone at 15 to 20° C., and the resulting mixture was stirred at room temperature for 3 days. Thereafter, the reaction mixture was concentrated under reduced pressure to about half volume. To the concentrated solution were added an aqueous sodium hydrogen sulfite solution and dilute hydrochloric acid, followed by extraction with ethyl acetate. The organic layer was dried over magnesium sulfate, and concentrated under reduced pressure, and 4-benzyloxy-3-fluoro-5-methoxybenzoic acid was obtained.

To 4-benzyloxy-3-fluoro-5-methoxybenzoic acid were added 20 ml of methanol, 20 ml of ethyl acetate and 50 mg of 10% palladium-carbon, and the mixture was stirred at room temperature for 4 hours under the hydrogen atmosphere. Thereafter, the reaction mixture was filtered through Celite (registered trade mark). The filtrate was concentrated under reduced pressure, and 4.5 g of 3-fluoro-4-hydroxy-5-methoxybenzoic acid was obtained.

3-Fluoro-4-hydroxy-5-methoxybenzoic acid

[Chemical Formula 79]

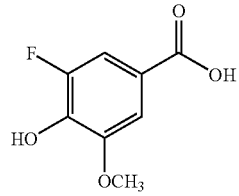

¹H-NMR (DMSO-d₆) δ: 3.87 (3H, s), 7.32-7.36 (2H, m).

To 80 ml of DMF were added 4.5 g of 3-fluoro-4-hydroxy-5-methoxybenzoic acid, 7.0 g of propargyl bromide, and 9.1 g of potassium carbonate, and the resulting mixture was stirred at room temperature for 2 days. Thereafter, hydrochloric acid was added to the reaction mixture, followed by extraction with ethyl acetate. The organic layer was dried over magnesium sulfate, and concentrated under reduced pressure. The residue was subjected to silica gel column chromatography, and 4.5 g of 2-propynyl 3-fluoro-5-methoxy-4-(2-propynyloxy)benzoate was obtained.

2-Propynyl 3-fluoro-5-methoxy-4-(2-propynyloxy)benzoate

[Chemical Formula 80]

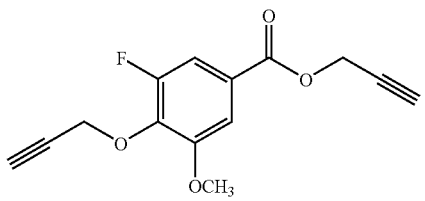

$^1$H-NMR (CDCl$_3$) δ: 2.49 (1H, t, J=2.4 Hz), 2.54 (1H, t, J=2.4 Hz), 3.94 (3H, s), 4.87 (2H, d, J=2.4 Hz), 4.91 (2H, d, J=2.4 Hz), 7.43 (1H, dd, J=1.8, 1.8 Hz), 7.48 (1H, dd, J=10.4, 1.8 Hz).

To 40 ml of methanol were added 4.5 g of 2-propynyl 3-fluoro-5-methoxy-4-(2-propynyloxy)benzoate and 20 ml of a 15% aqueous sodium hydroxide solution, and the resulting mixture was stirred at room temperature for 8 hours. Thereafter, the reaction mixture was concentrated under reduced pressure. To the residue was added hydrochloric acid to make the mixture acidic. The precipitated solids were collected by filtration, and dried, and 3.7 g of 3-fluoro-5-methoxy-4-(2-propynyloxy)benzoic acid was obtained.

3-Fluoro-5-methoxy-4-(2-propynyloxy)benzoic acid

[Chemical Formula 81]

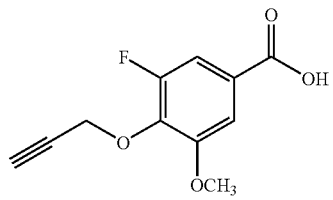

$^1$H-NMR (CDCl$_3$) δ: 2.50 (1H, t, J=2.4 Hz), 3.95 (3H, s), 4.89 (2H, d, J=2.4 Hz), 7.46-7.57 (2H, m).

Next, Formulation Examples will be shown. All the parts are by weight.

Formulation Example 1

Fifty (50) parts of each of the present compounds 1 to 43, and 3 parts of calcium lignin sulfonate, 2 parts of magnesium laurylsulfate and 45 parts of synthetic hydrated silicon oxide are thoroughly ground and mixed to obtain each wettable powder.

Formulation Example 2

Twenty (20) parts of each of the present compounds 1 to 43, and 1.5 parts of sorbitan trioleate are mixed with 28.5 parts of an aqueous solution containing 2 parts of polyvinyl alcohol, the mixture is finely-divided by a wet grinding process, then 40 parts of an aqueous solution containing 0.05 part of xanthan gum and 0.1 part of aluminum magnesium silicate is added thereto, 10 parts of propylene glycol is further added, and the mixture is stirred and mixed to obtain each flowable formulation.

Formulation Example 3

Two (2) parts of each of the present compounds 1 to 43, 88 parts of kaolin clay and 10 parts of talc are thoroughly ground and mixed to obtain each powder formulation.

Formulation Example 4

Five (5) parts of each of the present compounds 1 to 43, 14 parts of polyoxyethylene styryl phenyl ether, 6 parts of calcium dodecyl benzenesulfonate and 75 parts of xylene are thoroughly mixed to obtain each emulsifiable concentration.

Formulation Example 5

Two (2) parts of each of the present compounds 1 to 43, 1 part of synthetic hydrated silicon oxide, 2 parts of calcium lignin sulfonate, 30 parts of bentonite and 65 parts of kaolin clay are thoroughly ground and mixed, water is added, and the mixture is thoroughly kneaded, and granulated and dried to obtain each granule formulation.

Formulation Example 6

Ten (10) parts of each of the present compounds 1 to 43, 35 parts of white carbon containing 50 parts of polyoxyethylene alkyl ether sulfate ammonium salt, and 55 parts of water are mixed, and finely-divided by a wet grinding process to obtain each formulation.

The following Test Examples will show that the present compound is useful for controlling a plant disease.

The controlling effect was evaluated by visually observing the area of lesion spots on each of test plants at the time of investigation and comparing the area of lesion spots on a plant treated with the present compound with that on an untreated plant.

Test Example 1

Test of Preventive Effect on Wheat Powdery Mildew (*Erysiphe graminis* f. sp. *tritici*)

Each of plastic pots was filled with sandy loam and sown with wheat (cultivar: Shirogane), followed by growing in a greenhouse for 10 days. Each of the present compounds 1-19, 21-32, 34-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the wheat. After the foliage application, the plant was air-dried and then inoculated by sprinkling with spores of *Erysiphe graminis* f. sp. *tritici*. After the inoculation, the plant was held in a greenhouse at 23° C. for 7 days and the area of lesion spots was investigated. As a result, it was found that the area of lesion spots on the plant treated with each of the present compounds 1, 3, 21 and 36 was 30% or less of that on an untreated plant.

Test Example 2

Test of Preventive Effect on Wheat Glume Blotch (*Stagonospora nodorum*)

Each of plastic pots was filled with sandy loam and sown with wheat (cultivar: Shirogane), followed by growing in a greenhouse for 10 days. Each of the present compounds 1-19, 21-32, 34-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the wheat. After the foliage application, the plant was air-dried and then inoculated by spraying a water suspension of spores of *Stagonospora nodorum*. After the inoculation, the plant was held under darkness and high humidity conditions at 18° C. for 4 days and held under lighting conditions for 4 days, and then the area of lesion spots was investigated. As a result, it was found that the area of lesion spots on the plant treated with each of the present compounds 3, 7, 9, 11, 18, 19, 21, 22, 25, 31, 34, 36 and 37 was 30% or less of that on an untreated plant.

Test Example 3

Test of Preventive Effect on Wheat *Fusarium* Blight (*Fusarium culmorum*)

Each of plastic pots was filled with sandy loam and sown with wheat (cultivar: Shirogane), followed by growing in a greenhouse for 10 days. Each of the present compounds 1-19, 21-32, 34-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the wheat. After the foliage application, the plant was air-dried and then inoculated by spraying a water suspension of spores of *Fusarium culmorum*. After the inoculation, the plant was held under darkness and high humidity conditions at 23° C. for 4 days and held under lighting conditions for 3 days, and then the area of lesion spots was investigated. As a result, it was found that the area of lesion spots on the plant treated with each of the present compounds 1, 3, 21, 24, 34 and 36 was 30% or less of that on an untreated plant.

Test Example 4

Test of Preventive Effect on Cucumber Gray Mold (*Botrytis cinerea*)

Each of plastic pots was filled with sandy loam and sown with cucumber (cultivar: Sagamihanjiro), followed by growing in a greenhouse for 12 days. Each of the present compounds 1-19, 21-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the cucumber. After the foliage application, the plant was air-dried and a PDA medium containing spores of *Botrytis cinerea* was placed on the surfaces of the cucumber leaves. After the inoculation, the plant was grown at 12° C. and high humidity for 4 days. Then, the area of lesion spots was investigated. As a result, it was found that the area of lesion spots on the plant treated with each of the present compounds 18, 36 and 37 was 30% or less of that on an untreated plant.

Test Example 5

Test of Preventive Effect on Cucumber Stem Rot (*Sclerotinia sclerotiorum*)

Each of plastic pots was filled with sandy loam and sown with cucumber (cultivar: Sagamihanjiro), followed by growing in a greenhouse for 12 days. Each of the present compounds 1-14, 16-19, 21-29, 31-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the cucumber. After the foliage application, the plant was air-dried and a PDA medium containing mycelia of *Sclerotinia sclerotiorum* was placed on the surfaces of the cucumber leaves. After the inoculation, the plant was grown at 18° C. and high humidity for 4 days. Then, the area of lesion spots was investigated. As a result, it was found that the area of lesion spots on the plant treated with each of the present compounds 18, 21, 36 and 37 was 30% or less of that on an untreated plant.

Test Example 6

Test of Preventive Effect on Japanese Radish *Alternaria* Leaf Spot (*Alternaria brassicicola*)

Each of plastic pots was filled with sandy loam and sown with Japanese radish (cultivar: Wase 40-nichi), followed by growing in a greenhouse for 5 days. Each of the present compounds 1-19, 21-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the Japanese radish. After the foliage application, the plant was air-dried and then inoculated by spraying a water suspension of spores of *Alternaria brassicicola*. After the inoculation, the plant was held under high humidity conditions at 24° C. for 1 day and held in a greenhouse for 3 days, and then the area of lesion spots was investigated. As a result, it was found that the area of lesion spots on the plant treated with the present compound 18 was 30% or less of that on an untreated plant.

Test Example 7

Test of Curative Effect on Grape Downy Mildew (*Plasmopara viticola*)

Each of plastic pots was filled with sandy loam and sown with grape (cultivar: seedling of Berry-A), followed by growing in a greenhouse for 40 days. Each pot was inoculated by spraying a water suspension of zoosporangia of *Plasmopara viticola*, held under high humidity at 23° C. for 1 day and then air-dried to give a seedling infected with *Plasmopara viticola*. Each of the present compounds 1-14, 16-19, 21-33, 36-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the above grape seedling. After the foliage application, the plant was air-dried and then held in a greenhouse at 23° C. for 5 days and held under high humidity conditions at 23° C. for 1 day, and then the area of lesion spots was investigated. As a result, it was found that the area of lesion spots on the plant treated with each of the present compounds 1, 2, 24 and 36 was 30% or less of that on an untreated plant.

Test Example 8

Test of Preventive Effect on Tomato Late Blight (*Phytophthora infestans*)

Each of plastic pots was filled with sandy loam and sown with tomato (cultivar: Patio), followed by growing in a greenhouse for 20 days. Each of the present compounds 1-19, 21-40 and 41 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the tomato seedling. After the plant was air-dried so that the diluted solution on leaves was dried, a water suspension of zoosporangia of *Phytophthora infestans* was sprayed. After the inoculation, the plant was held under high humidity conditions at 23° C. for 1 day and held in a greenhouse for 4 days, and then the area of lesion spots was investigated. As a result, it was found that the area of lesion spots on the plant treated with each of the present compounds 6, 8, 9, 10, 11, 15, 17, 18, 19, 21, 31 and 34 was 30% or less of that an untreated plant.

INDUSTRIAL APPLICABILITY

As described above, the present compound has excellent plant disease controlling activity, and is useful in controlling plant diseases.

The invention claimed is:
1. An amide compound represented by the formula (1):

[Chemical Formula 1]

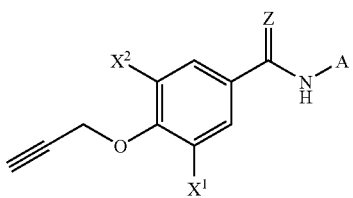

(1)

wherein
X$^1$ represents a fluorine atom or a methoxy group,
X$^2$ represents a hydrogen atom, a halogen atom, a C$_1$-C$_4$ alkyl group, a C$_2$-C$_4$ alkenyl group, a C$_2$-C$_4$ alkynyl group, a C$_1$-C$_4$ haloalkyl group, a C$_1$-C$_4$ alkoxy group, a C$_1$-C$_4$ alkylthio group, a hydroxy C$_1$-C$_4$ alkyl group, a nitro group, a cyano group, a formyl group, a NR$^1$R$^2$ group, a CO$_2$R$^3$ group, a CONR$^4$R$^5$ group, or a phenyl group optionally substituted with at least one group selected from the group consisting of a methyl group, a halogen atom, a cyano group and a nitro group,
Z represents an oxygen atom or a sulfur atom,
A represents a group represented by A$^1$-CR$^6$R$^7$R$^8$, A$^2$-Cy$^1$ or A$^3$-Cy$^2$,
A$^1$ represents a CH$_2$ group, a CH(CH$_3$) group, a C(CH$_3$)$_2$ group or a CH(CH$_2$CH$_3$) group,
A$^2$ represents a single bond, a CH$_2$ group, a CH(CH$_3$) group, a C(CH$_3$)$_2$ group or a CH(CH$_2$CH$_3$) group,
A$^3$ represents a methylene group substituted with at least one group selected from the group consisting of a C$_1$-C$_3$ haloalkyl group, a C$_2$-C$_4$ alkenyl group, a C$_2$-C$_4$ alkynyl group, a cyano group, a phenyl group and a C$_2$-C$_5$ alkoxycarbonyl group,
Cy$^1$ represents a C$_3$-C$_6$ cycloalkyl group substituted with at least one group selected from the following group [a-1], a C$_3$-C$_6$ cycloalkenyl group optionally substituted with at least one group selected from the following group [a-1], a C$_3$-C$_6$ cycloalkyl group optionally substituted with at least one group selected from the following group [a-1], and one of whose ring-forming methylenes is replaced with a carbonyl group, or a C$_3$-C$_6$ hydroxyiminocycloalkyl group optionally substituted with at least one group selected from the following group [a-1],
Cy$^2$ represents a C$_3$-C$_6$ cycloalkyl group optionally substituted with at least one group selected from the following group [a-2], a C$_3$-C$_6$ cycloalkenyl group optionally substituted with at least one group selected from the following group [a-2], a C$_3$-C$_6$ cycloalkyl group optionally substituted with at least one group selected from the following group [a-2], and one of whose ring-forming methylenes is replaced with a carbonyl group, or a C$_3$-C$_6$ hydroxyiminocycloalkyl group optionally substituted with at least one group selected from the following group [a-2],
R$^1$ and R$^2$ represent independently a hydrogen atom, a C$_1$-C$_4$ alkyl group, a C$_3$-C$_4$ alkenyl group, a C$_3$-C$_4$ alkynyl group, a C$_2$-C$_4$ haloalkyl group, a C$_2$-C$_5$ alkylcarbonyl group, a C$_2$-C$_5$ alkoxycarbonyl group or a C$_1$-C$_4$ alkylsulfonyl group,
R$^3$ represents a C$_1$-C$_4$ alkyl group, a C$_3$-C$_4$ alkenyl group or a C$_3$-C$_4$ alkynyl group,
R$^4$ represents a hydrogen atom, a C$_1$-C$_4$ alkyl group, a C$_3$-C$_4$ alkenyl group, a C$_3$-C$_4$ alkynyl group, a C$_2$-C$_4$ haloalkyl group, a C$_2$-C$_5$ alkylcarbonyl group, a C$_2$-C$_5$ alkoxycarbonyl group or a C$_1$-C$_4$ alkylsulfonyl group,
R$^5$ represents a hydrogen atom, a C$_1$-C$_4$ alkyl group, a C$_3$-C$_4$ alkenyl group, a C$_3$-C$_4$ alkynyl group or a C$_2$-C$_4$ haloalkyl group,
R$^6$ and R$^7$ represent independently a C$_1$-C$_4$ alkyl group,
R$^8$ represents a halogen atom, a hydroxyl group, a C$_1$-C$_6$ alkoxy group, a C$_3$-C$_6$ alkenyloxy group, a C$_1$-C$_6$ haloalkyl group, a C$_1$-C$_6$ haloalkoxy group, a phenyl group, a benzyl group, a C$_1$-C$_3$ alkylthio group, a hydroxy C$_1$-C$_6$ alkyl group, a C$_2$-C$_4$ alkylcarbonyloxy group, a (C$_1$-C$_3$ alkylamino)C$_1$-C$_6$ alkyl group, a (di(C$_1$-C$_3$ alkyl)amino) C$_1$-C$_6$ alkyl group, a mercapto group, a carbamoyl group, a formyl group, a C$_2$-C$_6$ cyanoalkyl group, a C$_1$-C$_3$ alkylsulfonyl group, a phenoxy group or an NR$^9$R$^{10}$ group (wherein R$^9$ and R$^{10}$ represent independently a hydrogen atom, a C$_1$-C$_4$ alkyl group, a C$_2$-C$_5$ alkylcarbonyl group, a C$_2$-C$_5$ alkoxycarbonyl group or a C$_1$-C$_4$ alkylsulfonyl group);
group [a-1]:
a C$_1$-C$_6$ alkoxy group, a C$_3$-C$_6$ alkenyloxy group, a C$_1$-C$_6$ haloalkyl group, a C$_1$-C$_6$ haloalkoxy group, a phenyl group, a benzyl group, a C$_1$-C$_3$ alkylthio group, a C$_1$-C$_3$ alkylidene group forming a double bond with the same ring-forming carbon atom, a hydroxy C$_1$-C$_6$ alkyl group, a C$_2$-C$_4$ alkylcarbonyloxy group, a (C$_1$-C$_3$ alkylamino) C$_1$-C$_6$ alkyl group, a (di(C$_1$-C$_3$ alkyl)amino) C$_1$-C$_6$ alkyl group, a mercapto group, a carbamoyl group, a formyl group, a C$_2$-C$_6$ cyanoalkyl group, a C$_1$-C$_3$ alkylsulfonyl group, a phenoxy group and an NR$^{11}$R$^{12}$ group (wherein R$^{11}$ and R$^{12}$ represent independently a hydrogen atom, a C$_1$-C$_4$ alkyl group, a C$_2$-C$_5$ alkylcarbonyl group; a C$_2$-C$_5$ alkoxycarbonyl group or a C$_1$-C$_4$ alkylsulfonyl group);

group [a-2]:
a halogen atom, a $C_1$-$C_4$ alkyl group, a $C_2$-$C_4$ alkenyl group, a $C_2$-$C_4$ alkynyl group, a hydroxyl group, a cyano group, a carboxyl group, a $C_2$-$C_5$ alkoxycarbonyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a ($C_1$-$C_3$ alkylamino)$C_1$-$C_6$ alkyl group, a (di($C_1$-$C_3$ alkyl)amino) $C_1$-$C_6$ alkyl group, a mercapto group, a carbamoyl group, a formyl group, a $C_2$-$C_6$ cyanoalkyl group, a $C_1$-$C_3$ alkylsulfonyl group, a phenoxy group and an $NR^{13}R^{14}$ group (wherein $R^{13}$ and $R^{14}$ represent independently a hydrogen atom, a $C_1$-$C_4$ alkyl group, a $C_2$-$C_5$ alkylcarbonyl group, a $C_2$-$C_5$ alkoxycarbonyl group or a $C_1$-$C_4$ alkylsulfonyl group).

2. The amide compound according to claim 1, wherein Z is an oxygen atom.

3. The amide compound according to claim 1, wherein $X^1$ is a fluorine atom, and $X^2$ is a hydrogen atom or a fluorine atom, or $X^1$ is a methoxy group and $X^2$ is a hydrogen atom or a methoxy group.

4. The amide compound according to claim 1, wherein $X^1$ and $X^2$ are a methoxy group.

5. The amide compound according to claim 1, wherein $X^1$ is a methoxy group, and $X^2$ is a hydrogen atom.

6. The amide compound according to claim 1, wherein $X^1$ and $X^2$ are a fluorine atom.

7. The amide compound according to claim 1, wherein $X^1$ is a fluorine atom, and $X^2$ is a hydrogen atom.

8. The amide compound according to claim 1, wherein A is $A^1$-$CR^6R^7R^8$, and $R^8$ is a fluorine atom, an amino group or a hydroxyl group.

9. The amide compound according to claim 1, wherein A is $A^2$-$Cy^1$, $A^2$ is a single bond, a $CH_2$ group or a $CH(CH_3)$ group, and $Cy^1$ is a $C_3$-$C_6$ cycloalkyl group substituted with at least one group selected from the group [a-1].

10. The amide compound according to claim 1, wherein A is $A^2$-$Cy^1$, $A^2$ is a single bond, a $CH_2$ group or a $CH(CH_3)$ group, and $Cy^1$ is a cyclohexyl group substituted with a group selected from the group consisting of a $C_1$-$C_6$ alkoxy group, a $C_1$-$C_6$ haloalkyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group and an $NR^{11}R^{12}$ group.

11. The amide compound according to claim 1, wherein A is $A^3$-$Cy^2$, $A^3$ is a methylene group substituted with a $C_1$-$C_3$ haloalkyl group, or a cyano group and $Cy^2$ is a $C_3$-$C_6$ cycloalkyl group substituted with at least one group selected from the group [a-2].

12. The amide compound according to claim 1, wherein A is $A^2$-$Cy^1$, $A^2$ is a single bond, a $CH_2$ group or a $CH(CH_3)$ group, and $Cy^1$ is a cyclohexyl group substituted with at least one group selected from the group consisting of a $C_1$-$C_6$ alkoxy group, a $C_1$-$C_6$ haloalkyl group, a hydroxy $C_1$-$C_6$ alkyl group and a $C_2$-$C_4$ alkylcarbonyloxy group.

13. The amide compound according to claim 1, wherein
A is a group represented by $A^1$-$CR^6R^7R^8$, $A^2$-$Cy^1$ or $A^3$-$Cy^2$,
$A^1$ is a $CH_2$ group, a $CH(CH_3)$ group, a $C(CH_3)_2$ group or a $CH(CH_2CH_3)$ group, $A^2$ is a single bond, a $CH_2$ group, a $CH(CH_3)$ group, a $C(CH_3)_2$ group or a $CH(CH_2CH_3)$ group, $A^3$ is a methylene group substituted with at least one group selected from the group consisting of a $C_1$-$C_3$ haloalkyl group, a $C_2$-$C_4$ alkenyl group, a $C_2$-$C_4$ alkynyl group, a cyano group and a phenyl group, $Cy^1$ is a $C_3$-$C_6$ cycloalkyl group substituted with at least one group selected from the following group [b-1], a $C_3$-$C_6$ cycloalkenyl group optionally substituted with at least one group selected from the following group [b-1], a $C_3$-$C_6$ cycloalkyl group optionally substituted with at least one group selected from the following group [b-1], and one of whose ring-forming methylenes is replaced with a carbonyl group, or a $C_3$-$C_6$ hydroxyiminocycloalkyl group optionally substituted with at least one group selected from the following group [b-1], $Cy^2$ is a $C_3$-$C_6$ cycloalkyl group optionally substituted with at least one group selected from the following group [b-2], a $C_3$-$C_6$ cycloalkenyl group optionally substituted with at least one group selected from the following group [b-2], a $C_3$-$C_6$ cycloalkyl group optionally substituted with at least one group selected from the following group [b-2], and one of whose ring-forming methylenes is replaced with a carbonyl group, or a $C_3$-$C_6$ hydroxyiminocycloalkyl group optionally substituted with at least one group selected from the following group [b-2], and $R^8$ is a halogen atom, a hydroxyl group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a carbamoyl group, a formyl group, a $C_2$-$C_6$ cyanoalkyl group, a $C_1$-$C_3$ alkylsulfonyl group or a phenoxy group;

group [b-1]: a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a carbamoyl group, a formyl group, a $C_2$-$C_6$ cyanoalkyl group, a $C_1$-$C_3$ alkylsulfonyl group and a phenoxy group;

group [b-2]:
a halogen atom, a $C_1$-$C_4$ alkyl group, a $C_2$-$C_4$ alkenyl group, a $C_2$-$C_4$ alkynyl group, a hydroxyl group, a cyano group, a $C_1$-$C_6$ alkoxy group, a $C_3$-$C_6$ alkenyloxy group, a $C_1$-$C_6$ haloalkyl group, a $C_1$-$C_6$ haloalkoxy group, a phenyl group, a benzyl group, a $C_1$-$C_3$ alkylthio group, a $C_1$-$C_3$ alkylidene group forming a double bond with the same ring-forming carbon atom, a hydroxy $C_1$-$C_6$ alkyl group, a $C_2$-$C_4$ alkylcarbonyloxy group, a (di($C_1$-$C_3$ alkyl)amino) $C_1$-$C_6$ alkyl group, a carbamoyl group, a formyl group, a $C_2$-$C_6$ cyanoalkyl group, a $C_1$-$C_3$ alkylsulfonyl group and a phenoxy group.

14. A plant disease controlling agent comprising the amide compound according to claim 1 as an active ingredient and an auxiliary agent for formulation.

15. A method of controlling a plant disease comprising treating a plant or a soil with an effective amount of the amide compound according to claim 1.

* * * * *